(12) United States Patent
Clarence-Smith et al.

(10) Patent No.: US 10,548,855 B2
(45) Date of Patent: Feb. 4, 2020

(54) MEMANTINE COMBINATIONS AND USE

(71) Applicant: CHASE PHARMACEUTICALS CORPORATION, Parsippany, NJ (US)

(72) Inventors: Kathleen E. Clarence-Smith, Washington, DC (US); Thomas N. Chase, Washington, DC (US)

(73) Assignee: Chase Pharmaceuticals Corporation, Parsippany, NJ (US)

( * ) Notice: Subject to any disclaimer, the term of this patent is extended or adjusted under 35 U.S.C. 154(b) by 110 days.

(21) Appl. No.: 15/795,990

(22) Filed: Oct. 27, 2017

(65) Prior Publication Data

US 2018/0116979 A1    May 3, 2018

Related U.S. Application Data

(60) Provisional application No. 62/423,999, filed on Nov. 18, 2016, provisional application No. 62/424,085, filed on Nov. 18, 2016, provisional application No. 62/414,359, filed on Oct. 28, 2016.

(51) Int. Cl.

| | | |
|---|---|---|
| *A61K 31/435* | (2006.01) | |
| *A61K 31/13* | (2006.01) | |
| *A61K 31/473* | (2006.01) | |
| *A61K 31/445* | (2006.01) | |
| *A61K 31/4725* | (2006.01) | |
| *A61K 31/496* | (2006.01) | |

(52) U.S. Cl.
CPC .......... *A61K 31/13* (2013.01); *A61K 31/445* (2013.01); *A61K 31/473* (2013.01); *A61K 31/4725* (2013.01); *A61K 31/496* (2013.01); *A61K 2300/00* (2013.01)

(58) Field of Classification Search
CPC .............................. A61K 31/435; A61K 31/13
USPC ................................................... 514/294, 662
See application file for complete search history.

(56) References Cited

U.S. PATENT DOCUMENTS

| 7,678,363 B2 | 3/2010 | Barlow et al. |
| 8,404,701 B2 | 3/2013 | Chase et al. |
| 2014/0200271 A1 | 7/2014 | Paterson et al. |
| 2016/0243112 A1 | 8/2016 | Wu et al. |

OTHER PUBLICATIONS

Kakkar et al., "Patent Cliff mitigation strategies: Giving new life to Blockbusters", Expert Opinion on Therapeutic Patent, 25(12):1354-3776 (2015).
Written Opinion for PCT/US2017/058677 dated Dec. 29, 2017.
International Search Report for PCT/US2017/058677 dated Dec. 29, 2017.
Chase et al, "High Dose Donepezil Treatment of Alzheimer's Disease—Preliminary Results from CPC-201 and CPC-212 Trials", http://www.chasepharmaceuticals.com/blog/high-dose-donepezil-treatment-of-alzheimers-disease-poster-presented-on-december-9-by-thomas-n.-chase-md (Dec. 2015).

*Primary Examiner* — Raymond J Henley, III
(74) *Attorney, Agent, or Firm* — Roy Issac

(57) ABSTRACT

A pharmaceutical combination of memantine and a non-anticholinergic antiemetic agent for the treatment of hypocholinergic disorders in further combination with high doses of donepezil and with solifenacin, and kits comprising said combination. A pharmaceutical combination of memantine and solifenacin for the treatment of hypocholinergic disorders, including Alzheimer type dementia, in further combination with high doses of donepezil, and kits comprising said combination.

8 Claims, No Drawings

MEMANTINE COMBINATIONS AND USE

CROSS-REFERENCE TO RELATED APPLICATIONS

This application claims priority benefit of United States Provisional Patent Application Ser. No. 62/414,359 filed Oct. 28, 2016, United States Provisional Patent Application Ser. No. 62/424,085 filed Nov. 18, 2016, and United States Provisional Patent Application Ser. No. 62/423,999 filed Nov. 18, 2016; the disclosures of which are herein incorporated by reference in their entirety.

FIELD OF THE INVENTION

This invention pertains to the field of the treatment of patients suffering from a hypocholinergic disorder in the brain such as Alzheimer disease, Lewy body disease, Parkinson's disease, and related disorders in humans. The invention provides a combination of memantine with a non-anticholinergic antiemetic agent (naAEA) to be safely administered to a patient suffering from a hypocholinergic disorder in further combination with donepezil high doses and solifenacin, thus inducing neuroprotection in said patient. The invention also provides a combination of memantine and solifenacin to be used in further combination with high donepezil doses for safely improving the symptoms of hypocholinergic disorders in a patient suffering from one or more of said hypocholinergic disorders and inducing neuroprotection in said patient, including dementia of the Alzheimer type and inducing neuroprotection in said Alzheimer type dementia patients.

Definitions

"NMDA": N-methyl-D-aspartate
"ChEI(s)": Choline Esterase Inhibitor(s).
"nsPAChA(s)": non-selective, peripheral AntiCholinergic Agent(s).
"Non-selective" referred to nsPAChAs, applies to anticholinergic agents exhibiting inhibitory activity broadly across the various subtypes of muscarinic M-receptors, namely the M1-M5 receptors, as currently identified.
"Peripheral": referred to nsPAChAs, applies to anticholinergics that are largely unable (have a limited ability) to enter the central nervous system following systemic administration and thus do not affect brain function to a clinically appreciable degree.
"naAEA(s)": non-anticholinergic Anti-Emetic Agent(s).
"Non-anticholinergic" refers to antiemetic medications not primarily regarded as anticholinergic agents; they are entirely devoid of anticholinergic activity or have an extremely low ability to prevent acetylcholine from acting at its cholinergic receptor sites.
"Anticholinergic therapy": the treatment with an anticholinergic agent of such medical conditions as gastro-intestinal cramping, nausea, retching, vomiting, fecal incontinence, bladder spasms, urinary incontinence, overactive bladder, asthma, motion sickness, muscular spasms, and smooth muscle contractive disorders; or the treatment, if any, with an anticholinergic agent of side effects caused by the ChEIs, including, but not limited to gastro-intestinal cramping, nausea, retching, vomiting, fecal incontinence, diarrhea bladder spasms, urinary incontinence, overactive bladder.
"Donepezil": the ChEI (±)-2,3-dihydro-5,6-dimethoxy-2-[[1-(phenylmethyl)-4-piperidinyl]methyl]-1H-inden-1-one.
"Memantine": the NMDA-antagonist 3,5-dimethyladamantan-1-amine.
"Solifenacin": the nsPAChA 1-azabicyclo[2.2.2]oct-3-yl (1R)-1-phenyl-3,4-dihydro-1H-isoquinoline-2-carboxylate.
"MTD": maximum (or maximal) tolerated dose, i.e. the highest dose of a drug or treatment that does not cause unacceptable side effects. The maximum tolerated dose is determined in clinical trials by testing increasing doses on different groups of people until the highest dose with acceptable side effects is found (NCI Drug Dictionary).
"IR": Immediate Release of the active ingredient from a composition.
"ER": Extended Release, including sustained release, modified release, controlled release and slow release of the active ingredient from a composition by any administration route, in particular, but not limited to oral and parenteral (including transcutaneous, transdermal, intramuscular, intravenous, and subcutaneous routes).
"comprising" means that the compositions and methods include the recited elements, but do not exclude others. "comprising" is inclusive of the terms "consisting of" and "consisting essentially of".
"consisting essentially of" means that the methods and compositions may include additional steps, components or ingredients, but only if the additional steps, components or ingredients do not materially alter the basic and novel characteristics of the claimed methods and compositions. In certain embodiments, "consisting essentially of" means that the subsequently named component(s) is necessarily included but that another unlisted ingredient (s) that does not materially affect the basic and novel properties can also be present. For example, when used to define compositions and methods, "consisting essentially of" means excluding other elements of any essential significance to the combination for the intended use. Thus, for example, a composition consisting essentially of the elements as defined herein would not exclude trace contaminants and pharmaceutically acceptable carriers.
"and/or" is used herein to mean both "and" as well as "or".
"pharmaceutically acceptable salt" means either a pharmaceutically acceptable acid addition salt or a pharmaceutically acceptable base addition salt of a currently disclosed compound that may be administered without any resultant substantial undesirable biological effect(s) or any resultant deleterious interaction(s) with any other component of a pharmaceutical composition in which it may be contained.
"combination therapy" means treating a patient with the combination of the ChEI, the NMDA-antagonist and the nsPAChA as a therapeutic platform in rotating, alternating and/or simultaneous treatment schedules. Combination therapy may include a temporal overlap of other therapeutic agents, depending on the clinical course of a given hypocholinergic disease in a subject.
"hypocholinergic disorder" as used herein means a clinical disorder reflecting a deficit of acetylcholine-mediated neurotransmission in the brain such as Alzheimer disease, dementias of the Alzheimer-type, Lewy body dementia, Parkinson's disease dementia, and related disorders in humans.

BACKGROUND OF THE INVENTION

The ability of memantine, a noncompetitive glutamatergic NMDA receptor antagonist of moderate affinity, to improve cognitive function in both animal models of human dementia and in patients with dementia of the AD type is well established. For example, in preclinical behavioral experiments using the water maze, this adamantane derivative (2 mg/kg) reverses scopolamine-induced learning deficits in mice (Dreyer B D, Anderson W G, Johnson H, O'Callaghan M, Seo S, Choi D Y, Riedel G, Platt B., "*Memantine acts as a cholinergic stimulant in the mouse hippocampus*", J Alzheimer's Dis. 2007 December; 12(4): 319-33. Similarly, controlled clinical trials have demonstrated the ability of memantine to benefit cognition in those suffering from moderate to severe forms of AD (Grossberg G T, Pejovic V, Miller M L, Graham S M, Dement "*Memantine therapy of behavioral symptoms in community-dwelling patients with moderate to severe Alzheimer's disease*". Geriatr Cogn Disord 2009; 27(2):164-172). These clinical trial results indicate that the antidementia efficacy and safety profile of memantine closely resemble those of donepezil and other approved ChEIs. Based on these findings in patients with moderate to severe AD, memantine has been approved for sale by regulatory authorities in the US and elsewhere for more than a decade.

More recently, memantine (usually 20 mg/day in an IR-unit form) has been reported to enhance the antidementia efficacy of ChEIs such as standard dose—usually 10 mg/day—donepezil (Tariot P N, Farlow M R, Grossberg G T, Graham S M, McDonald S, Gergel I—Memantine Study Group, "*Memantine treatment in patients with moderate to severe Alzheimer disease already receiving donepezil: a randomized controlled trial*", JAMA 2004 Jan. 21; 291(3): 317-324; Atri A, Molinuevo J L, Lemming O, Wirth Y, Pulte I, Wilkinson D, "*Memantine in patients with Alzheimer's disease receiving donepezil: new analyses of efficacy and safety for combination therapy*", Alzheimers Res Ther. 2013 Jan. 21; 5(1):6). However, results from some randomized controlled trials in patients with moderate to severe AD have failed to show that the combination of donepezil plus memantine confers significant efficacy advantages over donepezil alone, regardless of whether donepezil was given at the standard 10 mg/day or the 23 mg/day dose (Porsteinsson A P, Grossberg G T, Mintzer J, Olin J T; Memantine MEM-MD-12 Study Group, "Memantine treatment in patients with mild to moderate Alzheimer's disease already receiving a cholinesterase inhibitor: a randomized, double-blind, placebo-controlled trial", Curr Alzheimer Res. 2008 February; 5(1):83-9; Doody R S, Geldmacher D S, Farlow M R, Sun Y, Moline M, Mackell J, "Efficacy and safety of donepezil 23 mg versus donepezil 10 mg for moderate-to-severe Alzheimer's disease: a subgroup analysis in patients already taking or not taking memantine", Dement Geriatr Cogn Disord. 2012; 33(2-3):164-73; Howard R, McShane R, Lindesay J, Ritchie C, Baldwin A, Barber R, Burns A, Dening T, Findlay D, Holmes C, Hughes A, Jacoby R, Jones R, Jones R, McKeith I, Macharouthu A, O'Brien J, Passmore P, Sheehan B, Juszczak E, Katona C, Hills R, Knapp M, Ballard C, Brown R, Banerjee S, Onions C, Griffin M, Adams J, Gray R, Johnson T, Bentham P, Phillips P, "Donepezil and memantine for moderate to severe Alzheimer's disease", N Engl J Med. 2012 Mar. 8.; 366(10):893-903).

Moreover, there is no generally accepted rationale for any symptomatic benefit gained by combining these drugs. Indeed, early on memantine was considered to act as an anticholinergic and thus with the potential of exacerbating AD symptoms (Lipton S A, Nature Reviews Drug Diiscovery 2006; 5:160), while later its cognitive benefits were often linked to its well established ability to inhibit NMDA receptor mediated glutamatergic mechanisms (Johnson J W, Glasgow N G, Povysheva N V, "*Recent insights into the mode of action of memantine and ketamine*", Curr Opin Pharmacol 2015, February; 20:54-63).

Thus, to date, there is scant experimental support for this view and thus no basis to expect a synergistic or additive effect of memantine on cholinergic function. (Schmitt H P, "On the paradox of ion channel blockade and its benefits in the treatment of Alzheimer disease", Med Hypotheses. 2005; 65(2):259-65).

Conversely, it was established that the efficacy of the ChEI donepezil is improved by combining said donepezil with the nsPAChA solifenacin. In fact, for example, solifenacin is able to allow the increase up to 40 mg/day of donepezil daily dose in a human being, including a patients suffering from a dementia of Alzheimer type (Chase T N, Clarence-Smith K, "*High Dose Cholinesterase Inhibitor Treatment of Alzheimer's Disease*"—AAIC Poster Abstract #27291, 2015 [PI-290], Alzheimer's Association International Conference—2015, Jul. 24-28, Washington D.C.) In addition, said donepezil dose can also be further highly increased by increasing the dose of both solifenacin and donepezil, as illustrated in WO 2014/039627, the disclosure of which is incorporated herein in its entirety by reference.

The action of solifenacin high doses, i.e. of solifenacin doses that are at least as high as 10 mg, but also higher and even much higher, allow for an increase of the donepezil blood concentrations that are higher than those attained with donepezil alone and increase even further with increasing doses of solifenacin.

It is hereby specified that, in this disclosure and elsewhere in the scientific literature, donepezil, memantine and solifenacin are often cited as such, i.e. as the active molecules. In the pharmaceutical and medical field, these molecules are approved, sold, and used in form of a salt thereof, i.e. as donepezil hydrochloride, memantine hydrochloride and, respectively, solifenacin succinate (also designated "solifenacin compound with succinic acid 1:1" and the respective doses that are either administered in therapy or included in the respective commercial drugs are attributed to said salts.

SUMMARY OF THE INVENTION

In a clinical investigation according to the method disclosed in WO 2009/120227 (see also U.S. Pat. No. 8,404, 701), the disclosures of which are incorporated herein in their entirety by reference, donepezil and solifenacin were administered to patients suffering from Alzheimer type dementia. A number of said patients were under treatment with memantine and entered the trial by maintaining said treatment with memantine.

It has surprisingly been found that, by treating said patients under treatment with memantine with solifenacin and donepezil, instead of the expected, additive synergy as previously seen when memantine was added on to a moderately severe Alzheimer patient on a stable dose of donepezil, higher doses of donepezil were even more effective in patients also taking memantine, despite the fact that the memantine dose remained constant.

This "true" synergism appears more evident when a solifenacin dose at least as high as, but normally higher than the maximum unit form/daily solifenacin dose used in the anticholinergic therapy is administered to moderate/severe Alzheimer patients in a memantine/donepezil/solifenacin therapy.

Unexpectedly, it has also been found that a memantine/donepezil/solifenacin combination allows for clinically significant improvement of cognitive conditions of patients suffering from moderate/severe Alzheimer type dementia by using donepezil high doses.

In particular, it has been found that moderate/severe Alzheimer patients, who are concomitantly treated with a high dose of donepezil, the solifenacin-memantine combination induces greater improvement with said donepezil high-dose than those patients receiving said donepezil high-dose and solifenacin without concomitant memantine, where such greater improvement is significantly and unexpectedly greater than a mere additive effect of memantine.

Thus, the present invention provides a method for the treatment of hypocholinergic disorders, which comprises treating a patient in need of said treatment with a pharmaceutical combination comprising
(a) an effective amount of a N-methyl-D-aspartate receptor antagonist selected from the group consisting of memantine and pharmaceutical acceptable salts thereof [Component (a)]; and
(b) an effective amount of a non-selective peripheral anticholinergic agent selected from the group consisting of solifenacin and pharmaceutically acceptable salts thereof [Component (b)],
in further combination with a cholinesterase inhibitor selected from the group consisting of donepezil and pharmaceutically acceptable salts thereof [Component (c)], at a daily dose corresponding to from 10 mg to 92 mg, preferably from 20 mg to 92 mg, normally from 10 mg to 70 mg, preferably from 20 mg to 70 mg, of donepezil hydrochloride.

Advantageously, said amount of memantine or of a pharmaceutically acceptable salt thereof is provided in a daily dose that is equivalent to from 10 mg to 30 mg of memantine hydrochloride; and said amount of solifenacin or of a pharmaceutically acceptable salt thereof is provided in a daily dose that is equivalent to from 10 mg to 30 mg of solifenacin succinate.

The present invention also provides a pharmaceutical combination, which comprises
(a) an effective amount of a NMDA-antagonist selected from the group consisting of memantine and pharmaceutical acceptable salts thereof [Component (a)]; and
(b) an effective amount of a nsPAChA selected from the group consisting of solifenacin and pharmaceutically acceptable salts thereof [Component (b)],
for use for increasing the efficacy of a ChEI selected from the group consisting of donepezil and pharmaceutically acceptable salts thereof, in the treatment of hypocholinergic disorders. Said ChEI is administered at a daily dose that is advantageously equivalent to from 10 mg to 92 mg, preferably from 20 mg to 92 mg, normally from 10 mg to 70 mg, preferably from 20 mg to 70 mg, of donepezil hydrochloride.

In said combination, said effective amount of memantine or of a pharmaceutically acceptable salt thereof advantageously is a dose/unit form that is equivalent to from 5 mg to 30 mg of memantine hydrochloride; and said effective amount of solifenacin or of a pharmaceutically acceptable salt thereof is a dose/unit form that is equivalent to from 10 mg to 30 mg of solifenacin succinate.

Said effective amount of memantine or of a pharmaceutically acceptable salt thereof, equivalent to from 5 mg to 30 mg of memantine hydrochloride, is normally formulated in pharmaceutically compositions, preferably in dosage unit form, in admixture with a pharmaceutical carrier or vehicle.

Similarly, said effective amount of solifenacin or of a pharmaceutically acceptable salt thereof, equivalent to from 10 mg to 30 mg of solifenacin succinate, is normally formulated in pharmaceutically compositions, preferably in dosage unit form, in admixture with a pharmaceutical carrier or vehicle.

Moreover, the present invention provides a memantine/solifenacin fixed-dose combination consisting of a pharmaceutical composition, preferably in dosage unit form, comprising an effective amount of memantine or of a pharmaceutically acceptable salt thereof and an effective amount of solifenacin or of a pharmaceutically acceptable salt thereof, in admixture with a pharmaceutical carrier or vehicle.

Preferably, said effective amounts are equivalent to from 5 mg to 30 mg of memantine hydrochloride and, respectively, to from 10 mg to 30 mg of solifenacin succinate.

Furthermore, the present invention provides a memantine/solifenacin/donepezil fixed-dose combination consisting of a pharmaceutical composition, preferably in dosage unit form, comprising an effective amount of memantine or of a pharmaceutically acceptable salt thereof, an effective amount of solifenacin or of a pharmaceutically acceptable salt thereof, and an effective amount of donepezil or of a pharmaceutically acceptable salt thereof, in admixture with a pharmaceutical carrier or vehicle.

Advantageously, said effective amounts are, respectively, equivalent to from 5 mg to 30 mg, advantageously from 7 mg to 28 mg, of memantine hydrochloride; to from 10 mg to 30 mg, advantageously to from 15 mg to 25 mg of solifenacin succinate; and to from 10 mg to 92 mg, preferably from 20 mg to 92 mg, normally from 10 mg to 70 mg, preferably from 20 mg to 70 mg, of donepezil hydrochloride.

According to particular necessities, in particular for use in the titration phase of the therapy, the donepezil effective amount that is present in the above combinations, including the fixed-dose combinations, may be from 10 mg to 50 mg or from 40 mg to 70 mg, in particular of 10 mg, 15 mg, 20 mg, 25 mg, 30 mg, 35 mg, 40 mg, and 50 mg.

Thus, the present invention also provides a solifenacin/donepezil fixed-dose combination consisting of a pharmaceutical composition in dosage unit form, comprising from 10 mg to 30 mg, advantageously from 15 mg to 25 mg, preferably of 15 mg, of solifenacin succinate and from 10 mg to 92 mg, advantageously from 20 mg to 92 mg, normally from 10 mg to 70 mg, preferably from 20 mg to 70 mg, of donepezil hydrochloride, in admixture with a pharmaceutical carrier or vehicle+

Specific donepezil/solifenacin compositions comprise donepezil hydrochloride in an amount of from 10 mg to 50 mg, preferably of 10 mg, 15 mg, 20 mg, 25 mg, 30 mg 35 mg, 40 mg or 50 mg, of donepezil hydrochloride wherein said solifenacin succinate and donepezil hydrochloride do not interact each other.

Finally, the present invention provides kits for an easy and safe management of patients in need of a memantine/solifenacin/donepezil treatment.

It has also been found that, by treating a patient suffering from a hypocholinergic disorder, as hereinabove defined, with a donepezil/solifenacin combination, said patient concomitantly also taking memantine, the addition of an anticholinergic antiemetic agent to said memantine, especially as a memantine/naAEA fixed-dose combination, assures a safe treatment and allows for the increase of the donepezil doses without any appearance of cholinergic effects.

Thus, the present invention provides a method for the treatment of hypocholinergic disorders, which comprises treating a patient in need of said treatment with a pharmaceutical combination comprising
(a) an effective amount of a N-methyl-D-aspartate receptor antagonist selected from the group consisting of memantine and pharmaceutical acceptable salts thereof [Component (a)];
(b) a non anticholinergic antiemetic agent (naAEA) [Component (b)];
(c) a cholinesterase inhibitor selected from the group consisting of donepezil and pharmaceutically acceptable salts thereof [Component (c)], at a daily dose that is equivalent to from 10 mg to 92 mg, preferably from 20 mg to 92 mg, normally from 10 mg to 70 mg, preferably from 20 mg to 70 mg of donepezil hydrochloride; and
(d) an effective amount of a non-selective peripheral anticholinergic agent selected from the group consisting of solifenacin and pharmaceutically acceptable salts thereof [Component (d)];

Advantageously, said amount of memantine or of a pharmaceutically acceptable salt thereof is a daily dose that is equivalent to from 5 mg to 30 mg of memantine hydrochloride; and said amount of solifenacin or of a pharmaceutically acceptable salt thereof is a daily dose that is equivalent to from 10 mg to 30 mg, preferably from 15 mg to 25 mg, of solifenacin succinate.

Any naAEA that is an antiemetic medications commonly used to treat emesis, and not primarily regarded as anticholinergic agents, that is entirely devoid of anticholinergic activity or has an extremely low ability to prevent acetylcholine from acting at its cholinergic receptor sites in the brain may be used as Component (b) of the pharmaceutical combination of the present invention.

Preferably, said Component (b) is a non-anticholinergic antiemetic agent selected from the group consisting of (b1) 5HT3-antagonists, (b2) DA-antagonists, (b3) H1-antagonists, (b4) cannabinoids, and (b5) NK1-antagonists.

In said combination, said effective amount of memantine or of a pharmaceutically acceptable salt thereof advantageously is a dose/unit form that is equivalent to from 5 mg to 30 mg of memantine hydrochloride; and said effective amount of solifenacin or of a pharmaceutically acceptable salt thereof is a dose/unit form that is equivalent to from 10 mg to 30 mg, advantageously from 15 mg to 25 mg, of solifenacin succinate.

Said effective amount of memantine or of a pharmaceutically acceptable salt thereof, equivalent to from 5 mg to 30 mg of memantine hydrochloride, is normally formulated in pharmaceutically compositions, preferably in dosage unit form, in admixture with a pharmaceutical carrier or vehicle.

Similarly, said effective amount of solifenacin or of a pharmaceutically acceptable salt thereof, equivalent to from 10 mg to 30 mg, advantageously from 15 mg to 25 mg, of solifenacin succinate, is normally formulated in pharmaceutically compositions, preferably in dosage unit form, in admixture with a pharmaceutical carrier or vehicle.

Also donepezil or a pharmaceutical acceptable salt thereof Component (c) is normally formulated in pharmaceutically compositions, in an amount that is equivalent to from 10 mg to 92 mg, preferably from 20 mg to 92 mg of donepezil hydrochloride, in admixture with a pharmaceutical carrier or vehicle.

According to particular necessities, in particular for use in the titration phase of the therapy, the donepezil effective amount that is present in the above combinations, including the fixed-dose combinations, may be from 10 mg to 50 mg, in particular of 10 mg, 15 mg, 20 mg, 25 mg, 30 mg, 35 mg, 40 mg and 50 mg.

The present invention provides the above combination wherein said Component (a) and said Component (b) are formulated in the same unit form. Herein below, the novel (a)+(b) fixed-dose combination will also be designated as "Component (a/b)". This fixed-dose combination is particular advantageous because it allows a safe administration of high doses of both solifenacin and donepezil and the full expression of the synergy of solifenacin on both donepezil and memantine in patients treated with a memantine/donepezil combination or composition.

The present invention also provides the above combination wherein said Components (b) and (c) are formulated in the same unit form. Herein below, the (b)+(c) fixed-dose combination will also be designated as "Component (b/c)". The naAEA/donepezil fixed doses combinations are obtainable as described in WO 2011/034568 (see also U.S. Pat. Nos. 9,192,591 and 9,278,092), the contents of which are incorporated herein in their entirety by reference.

The present invention further provides the above combination, wherein said Components (a) and (c) are formulated in the same unit form. Herein below, the (a)+(c) fixed-dose combination will also be designated as "Component (a/c)". This fixed dose combination is also available as a brand preparation (Namzaric®) consisting of memantine hydrochloride extended-release/donepezil hydrochloride fixed-dose combination, when a 10-mg donepezil dose is required.

In addition, any one of the Components (a), (b) and (c) of the combination according to the present invention may be in a fixed-dose combination with solifenacin Component (d). Herein below, said fixed-dose combinations will be referred to as "Component (a/d)", "Component (b/d)" and, respectively, "Component (c/d)".

The (a)+(d) fixed-dose combination [Component (a/d)] is particular advantageous because it has been demonstrated that solifenacin Component (d) acts synergistically in the memantine Component (a)/donepezil Component (c) combination.

The naAEA/solifenacin fixed-dose combination Component (b/d) is exhaustively illustrated in WO 2014/039627 (see also US 2015/0231122), the contents of which are incorporated herein in their entirety by reference.

The donepezil/solifenacin fixed-dose combination Component (c/d) is cited in WO 2009/120277 (see also U.S. Pat. No. 8,404,701), the contents of which are incorporated herein in their entirety by reference.

However, as set forth above, in the case of particular necessities, especially for use in the titration phase of the therapy, the donepezil effective amount that is present in the above fixed-dose combinations (Component (c/d/), may be from 10 mg to 50 mg, in particular of 10 mg, 15 mg, 20 mg, 25 mg, 30 mg, 35 mg, 40 mg, and 50 mg.

Thus, the present invention also provides a solifenacin/donepezil (c/d) fixed-dose combination consisting of a pharmaceutical composition, preferably in dosage unit form, comprising from 10 mg to 30 mg, advantageously from 15 mg to 25 mg, preferably 15 mg, of solifenacin succinate and from 10 mg to 92 mg, advantageously from 20 mg to 92 mg, normally from 10 mg to 70 mg, preferably from 20 mg to 70 mg of donepezil hydrochloride, in admixture with a pharmaceutical carrier. Specific donepezil/solifenacin compositions comprise donepezil hydrochloride in an amount of from 10 mg to 50 mg, preferably of 10 mg, 15 mg, 20 mg, 25 mg, 30 mg 35 mg or 40 mg, of donepezil hydrochloride wherein said solifenacin succinate and donepezil hydrochloride do not interact each other.

Components (a), (b), (c) and (d) may also be combined in a triple fixed-dose combination, herein below designated as (b/c/d), (a/c/d), (a/b/d) and (a/b/c) fixed-dose combinations or in a (a/b/c/d) fixed-dose combination.

In fact, the present inventors found that, in order to assure safe treatment of Alzheimer type dementia and sure synergy with solifenacin Component (c), the non-anticholinergic antiemetic agent Component (b) must be administered concurrently with the memantine Component (a) and the donepezil Component (c) from the beginning of the therapeutic treatment of a patient submitted to this treatment for the first time. In order to assure said safe treatment, said naAEA Component (b) and said solifenacin Component (d) are preferably present in said combination as a fixed-dose combination consisting of a pharmaceutical composition wherein said naAEA and said solifenacin are formulated in a dosage unit form in admixture with a pharmaceutical carrier, as disclosed for example in WO 2014/039627 (see also U.S. Pat. No. 9,192,591).

Finally, the present invention provides kits for an easy and safe management of patients in need of a memantine/donepezil/solifenacin treatment, in particular a kit wherein the Components (a), (b), (c) and (d), each alone or in double or triple fixe-dose combination.

These kits, which contain donepezil or a pharmaceutically acceptable salt thereof, in a pharmaceutical composition in dosage unit form wherein said ChEI is in admixture with a pharmaceutical carrier, can simplify the administration of the above combination to patients suffering from hypocholinergic disorders of the CNS, who are often not sufficiently able to manage multiple packages.

Advantageously, the effective amounts are, respectively, equivalent to from 5 mg to 30 mg, preferably from 7 mg to 28 mg, of memantine hydrochloride; to from 10 mg to 30 mg, advantageously from 15 mg to 25 mg, preferably 15 mg, of solifenacin succinate; and from 10 mg to 92 mg, preferably from 20 mg to 92 mg, normally from 10 mg to 70 mg, preferably from 20 mg to 70 mg mg of donepezil hydrochloride.

As mentioned above, according to particular necessities, the donepezil effective amount that is present in the above combinations, including the fixed-dose combinations, may be of from 10 mg to 50 mg, in particular of 10 mg, 15 mg, 20 mg, 25 mg, 30 mg, 35 mg or 40 mg.

DETAILED DESCRIPTION

The present invention provides a new tool for the treatment of hypocholinergic disorders that is based on the fact that, by treating a patient suffering from said disorder with memantine and a naAEA, the addition of donepezil high doses and solifenacin to this therapy allows the induction by solifenacin of a full synergism towards both donepezil and memantine.

The addition of an antiemetic assures a safe expression of said synergy.

The present invention also provides a new tool for the treatment of hypocholinergic disorders that is based on the fact that, by allowing the safe increase of the donepezil dose, solifenacin allows a full synergism between donepezil and memantine.

A study in patients with AD-type dementia has shown a greater improvement in patients receiving memantine/solifenacin/donepezil than in those receiving donepezil/solifenacin and where such greater improvement is greater than a mere additive effect of memantine. In this study, improvement in cognition was judged versus baseline, at a time when patients were either on or off memantine and continued to receive the same dose of memantine for the duration of the trial. By contrast, the dose of donepezil was titrated up to Maximum Tolerated Dose. It was therefore expected that any further increase in efficacy would have been be attributable only to the higher doses of donepezil. There should therefore have been no difference in improvement between high dose donepezil with memantine or without memantine. Yet, patients who were concomitantly treated with memantine had greater improvement with high doses of donepezil than patients receiving high doses of donepezil without concomitant memantine, i.e, the effect of the high dose of donepezil itself was amplified by memantine, thus showing that the memantine/solifenacin combination is a new tool for the safe treatment of Alzheimer type dementia. This study is described in more detail in Example 1 below.

The present invention provides a combination of memantine or a pharmaceutically acceptable salt thereof (especially its hydrochloride), with solifenacin (especially its succinate) or a pharmaceutically acceptable salt thereof, donepezil or a pharmaceutically acceptable salt thereof (especially its hydrochloride), and a non-anticholinergic antiemetic agent that will provide improved treatment of hypocholinergic disorders such as Alzheimer type dementia.

The present invention provides a pharmaceutical combination comprising, as Components,
(a) memantine or a pharmaceutically acceptable salt thereof; and
(b) solifenacin or a pharmaceutically acceptable salt thereof.

The present invention also provides a combination of memantine or a pharmaceutically acceptable salt thereof (especially its hydrochloride) Component (a), with a non-anticholinergic antiemetic agent Component (b), to be used in further combination with donepezil or a pharmaceutically acceptable salt thereof (especially its hydrochloride) Component (c), and solifenacin or a pharmaceutically acceptable salt thereof (especially its succinate) Component (d), to provide improved treatment of hypocholinergic disorders such as Alzheimer type dementia.

These combinations include fixed-dose combinations, in particular a Component (a)/Component (b) fixed dose combination essentially consisting of a pharmaceutical composition in dosage unit form comprising
(a) memantine or a pharmaceutically acceptable salt thereof, in an amount that is equivalent to from 5 mg to 30 mg of memantine hydrochloride; and
(b) a non-anticholinergic antiemetic agent,
in admixture with a pharmaceutical carrier or vehicle.

This composition is useful because it compels the concurrent administration of a memantine/antiemetic combination assuring a safe treatment of said patient suffering from said hypocholinergic disorder with the donepezil Component (c), even at high and very high doses, and the solifenacin Component (d); and also because it renders said administration of a quadruple combination more comfortable.

Component (c) and Component (d) may also be in a fixed-dose combinations, that allows the administration of the two components together in a composition to be administered once per day, thus also contributing in rendering the treatment more comfortable for both the patient and the caregiver.

For the same purpose, the combination according to the present invention is packaged in kits.

The Memantine Component (a)

Memantine hydrochloride, which can be prepared for example as described in U.S. Pat. No. 3,391,142, the disclosure of which is incorporated herein in its entirety by reference, is a known NMDA-antagonist extensively used in the treatment of neurodegenerative disorders. Memantine and its pharmaceutically acceptable salts, such as the hydrochloride or the sulfate, alone or in combination with cholinesterase inhibitors, in particular with donepezil and pharmaceutically acceptable salts thereof, is disclosed for example in US 2014/0050784 and in US 2004/0087658, the disclosure of which is incorporated herein in its entirety by reference.

Memantine may be administered as a brand product, in particular, as its hydrochloride or sulfate salt, in tablets for oral immediate-release form or in capsules oral extended release form, or as oral disintegrable tablets, for example as described in EP 2905019, the disclosure of which is incorporated herein in its entirety by reference. Memantine can also be administered by a percutaneous system such as transdermal patch, as described in WO 2014/174564 and WO 2014/199455, the disclosures of which are incorporated herein in their entirety by reference, or by injection in a long-acting preparation containing its pamoate salt (N Mittapelly et al. "*Investigation of salt formation between memantine and pamoic acid*", Eur J Pharm Biopharm, 2016. April; 101, 62-71—see also U.S. Pat. No. 9,353,059 and US 2016/0310411, the disclosures of which are incorporated herein in their entirety by reference).

According to the present invention, memantine or pharmaceutically acceptable salts thereof is present in the combination in an amount of from 5 mg to 30 mg and is administered to a patient at a daily dose that is equivalent to from 10 mg to 30 mg.

A memantine/donepezil fixed-dose (a/c) combination, known as Namzaric®, may also be used according to the present invention.

According to the present invention, memantine or pharmaceutically acceptable salts thereof Component (a) is present in the combination in an amount of from 5 mg to 30 mg, preferably from 7 mg to 28 mg, and is administered to a patient at a daily dose that is equivalent to from 7 mg to 28 mg.

The naAEA Component (b)

Antiemetic medications commonly used to treat emesis, and not primarily regarded as anticholinergic agents, that are entirely devoid of anticholinergic activity or have an extremely low ability to prevent acetylcholine from acting at its cholinergic receptor sites in the brain may be used as Component (b) of the pharmaceutical combination of the present invention.

Preferably, said Component (b) is a non-anticholinergic antiemetic agent selected from the group consisting of (b1) 5HT3-antagonists, (b2) DA-antagonists, (b3) H1-antagonists, (b4) cannabinoids, and (b5) NK1-antagonists.

Typical non-anticholinergic antiemetic agents are

5-HT3 receptor antagonists (5HT3-antagonists), such as 9-methyl-3-[(2-methyl-1H-imidazol-1-yl)methyl]-1,2,3, 9-tetrahydrocarbazol-4-one (ondansetron) and pharmaceutically acceptable salts and solvates thereof, in particular its hydrochloride dihydrate, described in EP 191562, the disclosure of which is incorporated herein in its entirety by reference; 3S-ondansetron; 3R-onsdansetron; (3R)-10-oxo-8-azatricyclo[5.3.1.0 3,8]undec-5-yl 1H-indole-3-carboxylate (dolasetron) and pharmaceutically acceptable salts and solvates thereof, in particular its monomethanesulfonate (mesylate or mesilate) monohydrate, described in EP 266730; 1-methyl-N-(9-methyl-9-azabicyclo[3.3.1]non-3-yl)-indazole-3-carboxamide (granisetron) and pharmaceutically acceptable salts and solvates thereof, in particular its hydrochloride, described in EP 200444; [(1S,5S)-8-methyl-8-azabicyclo[3.2.1]oct-3-yl]1H-indole-3-carboxylate (tropisetron) and pharmaceutically acceptable salts and solvates thereof, in particular its monohydrochloride, described in U.S. Pat. No. 4,789,673, the disclosure of which is incorporated herein in its entirety by reference; 1-phenylmethyl-2-piperazinyl-1H-benzimidazole (lerisetron) and pharmaceutically acceptable salts and solvates thereof, in particular its hydrochloride, described in EP 512939, the disclosure of which is incorporated herein in its entirety by reference; (R)-5-[(1-methyl-3-indolyl)carbonyl]-4,5,6,7-tetrahydro-1H-benzimidazole (ramosetron) and pharmaceutically acceptable salts and solvates thereof, in particular its hydrochloride, described in U.S. Pat. No. 5,344,927, the disclosure of which is incorporated herein in its entirety by reference; (3aR)-2-[(3S)-1-azabicyclo[2.2.2]oct-3-yl]-2,3,3a,4,5,6-hexahydro-1H-benz[de]isoquinolin-1-one (palonosetron) and pharmaceutically acceptable salts and solvates thereof, in particular its hydrochloride, described in U.S. Pat. No. 5,202,333, the disclosure of which is incorporated herein in its entirety by reference; 2,3,4,5-tetrahydro-5-methyl-2-[(5-methyl-1H-imidazol-4-yl)methyl]-1H-pyrido[4,3-b]indol-1-one (alosetron) and pharmaceutically acceptable salts and solvates thereof, in particular its hydrochloride, described in U.S. Pat. No. 5,360,800, the disclosure of which is incorporated herein in its entirety by reference; and (±)-6-chloro-,3,4-dihydro-4-methyl-3-oxo-N-(quinuclidinyl)-2H-1,4-benzoxazine-8-carboxamide (azasetron) and pharmaceutically acceptable salts and solvates thereof, in particular its hydrochloride, described in U.S. Pat. No. 4,892,872, the disclosure of which is incorporated herein in its entirety by reference; which are known to be serotonin receptors blockers in the central nervous system and gastrointestinal tract and have been proposed for use to treat post-operative and cytotoxic drug nausea and vomiting;

dopamine antagonists ("DA-antagonists"), such as 5-chloro-1-(1-[3-(2-oxo-2,3-dihydro-1H-benzo[d]imidazol-1-yl)propyl]piperidin-4-yl)-1H-benzo[d]imidazol-2(3H)-one (domperidone) and pharmaceutically acceptable salts and solvates thereof, particularly its maleate; 1-[1-[4-(4-fluorophenyl)-4-oxo-butyl]-3,6-dihydro-2H-pyridin-4-yl]-3H-benzoimidazol-2-one (droperidol); 4-[4-(4-chlorophenyl)-4-hydroxy-1-piperidyl]-1-(4-fluorophenyl)-butan-1-one (haloperidol); 3-(2-chloro-10H-phenothiazin-10-yl)-N,N-dimethyl-propan-1-amine (chlorpromazine) and pharmaceutically acceptable salts and solvates thereof, particularly its hydrochloride; 2-chloro-10-[3-(4-methyl-1-piperazinyl)propyl]-10H-phenothiazine (prochlorperazine), and pharmaceutically acceptable salts and solvates thereof, particularly its dimaleate, dimesylate or 1,2-ethanedisulfonate (1:1) (edisilate); dimethyl[1-(10H-phenothiazin-10-yl)propan-2-yl]amine (promethazine) and pharmaceutically acceptable salts and solvates thereof, particularly its hydrochloride; 4-aminosalicylamide and benzamide derivatives like 4-amino-5-chloro-N-[2-(diethylamino)ethyl]-2-methoxy-benzamide (metoclopramide) and pharmaceutically acceptable salts and solvates thereof such as its monohydrochloride monohydrate; 4-amino-5-bromo-N-[2-(diethylamino)ethyl]-2-methoxybenzamide (bromopride) and pharmaceutically acceptable salts and solvates thereof, particularly its monohydrochloride and its dihydrochloride monohydrate; 4-amino-N-(1-benzylpiperidin-4-yl)-5-chloro-2-methoxybenzamide (clebopride) and pharmaceutically acceptable salts and solvates thereof, particularly its malate or its hydrochloride monohydrate; N-[(1-allylpyrrolidin-2-yl)methyl]-6-methoxy-1H-benzo

[d][1,2,3]triazole-5-carboxamide (alizapride) and pharmaceutically acceptable salts and solvates thereof, particularly its hydrochloride; (L)-2-methoxy-N-((1-propylpyrrolidin-2-yl)methyl)-5-sulfamoylbenzamide (levosulpiride); N-{[4-(2-dimethylaminoethoxy)phenyl]methyl}-3,4,5-trimethoxy-benzamide (trimethobenzamide) and pharmaceutically acceptable salts and solvates thereof, particularly its hydrochloride;

which act in the brain and especially at the chemoreceptor trigger zone and are known to be used to treat nausea and vomiting associated with neoplastic disease, radiation sickness, opioids, cytotoxic drugs and general anesthetics;

H1 histamine receptor antagonists ("H1-antagonists"), such as 1-[(4-chlorophenyl)-phenyl-methyl]-4-[(3-methylphenyl)methyl]piperazine (meclizine or meclozine) and pharmaceutically acceptable salts and solvates thereof, particularly its dihydrochloride monohydrate; dimethyl[1-(10H-phenothiazin-10-yl)propan-2-yl]amine (promethazine) and pharmaceutically acceptable salts and solvates thereof, particularly its hydrochloride; 3-(2-chloro-10H-phenothiazin-10-yl)-N,N-dimethyl-propan-1-amine (chlorpromazine) or a salt thereof, particularly its hydrochloride; 2-chloro-10-[3-(4-methyl-1-piperazinyl)propyl]-10H-phenothiazine (prochlorperazine) and pharmaceutically acceptable salts and solvates thereof, particularly its dimaleate, dimesylate or 1,2-ethanedisulfonate (1:1) (edisilate); and 2-(2-{4-[(4-chlorophenyl)(phenyl)methyl]piperazin-1-yl}ethoxy) ethanol (hydroxyzine) and pharmaceutically acceptable salts and solvates thereof such as its hydrochloride or 1,1'-methylene-bis(2-hydroxy-3-naphthalenecarboxylic acid salt (pamoate), which are known to be effective in many conditions, including motion sickness and severe morning sickness in pregnancy;

cannabinoid receptor agonists ("cannabinoids"), such as cannabis; (6aR-trans)-6a,7,8,10a-tetrahydro-6,6,9-trimethyl-3-pentyl-6H-dibenzo[b,d]pyran-1-ol (dronabinol); (6aR,10aR)-rel-3-(1,1-dimethylheptyl)-6,6a,7,8,10,10a-hexahydro-1-hydroxy,6,6-dimethyl-9H-dibenzo[b,d]pyran-9-one (nabilone); and (−)-cis-3-[2-hydroxy-4-(1,1-dimethylheptyl)-phenyl]-trans-4-(3-hydroxypropyl) cyclohexanol (CP 55,940);

which are known to be used in patients with cachexia and cytotoxic nausea and vomiting; and antagonists of the neurokinin 1 receptor (NK1-antagonists) such as 5-[[[(2R,3S)-2-[(1R)-1-[3,5-bis(trifluoromethyl)phenyl]ethoxy]-3-(4-fluorophenyl)-4-morpholinyl]methyl]-1,2-dihydro-3H-1,2,4-triazol-3-one (aprepitant); (2S,4S)-4-(4-Acetyl-1-piperazinyl)-N-[(1R)-1-[3,5-bis(trifluoromethyl)phenyl]ethyl]-2-(4-fluoro-2-methylphenyl)-N-methyl-1-piperidinecarboxamide (casopitant); 2-[3,5-bis(trifluoromethyl)phenyl]-N,2-dimethyl-N-[4-(2-methylphenyl)-6-(4-methyl-1-piperazinyl)-3-pyridinyl]propanamide (netupitant) described in U.S. Pat. Nos. 6,297,375, 6,719,996 and 6,593,47; the disclosures of which are incorporated herein in their entirety; and (5S,8S)-8-({(1R)-1-[3,5-bis(trifluoromethyl)phenyl]ethoxy}methyl)-8-phenyl-1,7-diazaspiro[4.5]decan-2-one (rolapitant), described in U.S. Pat. No. 7,049,320 and, for an injectable form thereof, in U.S. Pat. No. 9,101,615, the disclosures of which are incorporated herein in their entirety by reference; the disclosures of which are incorporated herein in their entirety; which are known to be neurokinine-1 receptors blockers in both the central and peripheral nervous system and have been proposed for use to treat cytotoxic drug nausea and vomiting.

Advantageous naAEAs are the compounds available in drugs for current antiemetic therapy, in particular, alosetron hydrochloride, available at the oral dose/unit form (in alosetron) of 0.5-1 mg;

azasetron hydrochloride or mesilate monohydrate, available at the oral or i.v. dose/unit form of 10 mg;

dolasetron mesylate monohydrate, available at the oral dose/unit form (in dolasetron) of 50-100 mg;

granisetron hydrochloride, available at the oral dose (in granisetron) of 1-2 mg or in a 52 cm$^2$ transdermal patch containing 34.3 mg of granisetron releasing 3.1 mg of granisetron per 24 hours (herein below indicated as 23.1 mg/24 h";

ondansetron hydrochloride dihydrate, available at the oral dose (in ondansetron) of 4-8 mg;

palonosetron hydrochloride, available at a the oral dose (in palonosetron) of 0.5 mg and i.v. dose (in palonosetron) of 0.25 mg;

tropisetron hydrochloride, available at the oral dose (in tropisetron) of 5 mg;

domperidone, available at the dose of 10 mg;

haloperidol, available at the oral dose of 1-10 mg;

chlorpromazine hydrochloride, available at the oral dose (in chlorpromazine) of 25-100 mg;

prochlorperazine dimaleate, available at the oral dose of 5 mg;

metoclopramide hydrochloride dihydrate, available at the oral dose (in metoclopramide) of 10 mg;

bromopride dihydrochloride monohydrate, available at the oral dose (in bromopride) of 10 mg;

clebopride malate (1:1), available at a oral dose (in clebopride) of 1 mg;

levosulpiride, at the oral dose of 25-100 mg;

alizapride hydrochloride, available at the oral dose (in alizapride) of 50 mg;

trimethobenzamide hydrochloride, available at the oral dose (in trimethobenzamide) of 100 mg meclizine (also called meclozine), available at the oral dose of 12.5-50 mg;

promethazine hydrochloride, available at the oral dose (in promethazine) of 25 mg;

dronabinol, available at the oral dose of 0.5-1 mg;

aprepitant, available at the oral dose of 40-125 mg;

netupitant, available at the oral dose of 300 mg; and casopitant, at the oral dose of 50 mg;

rolapitant, available at the oral dose of 60 mg;

the palonosetron-0.5 mg/netupitant-300 mg oral fixed-dose combination.

In the pharmaceutical combination to improve the treatment of human dementias of the Alzheimer type according to the present invention, the non-anticholinergic antiemetic agent Component (b) is formulated in a pharmaceutical composition in admixture with a pharmaceutical carrier to be administered in combination with the memantine Component (a), the nsPAChA component (d) and the donepezil Component (c).

The Component (b) is advantageously selected from the group consisting of alosetron and pharmaceutically acceptable salts and solvates thereof, especially its hydrochloride; azasetron and pharmaceutically acceptable salts and solvates thereof, especially its hydrochloride; ondansetron and pharmaceutically acceptable salts and solvates thereof, especially its monohydrochloride dihydrate; granisetron and pharmaceutically acceptable salts and solvates thereof, especially its hydrochloride; dolasetron and pharmaceutically acceptable salts and solvates thereof, especially its monomethanesulfonate monohydrate, ramosetron and pharmaceutically acceptable salts and solvates thereof, especially its hydrochloride; tropisetron and pharmaceutically acceptable salts and solvates thereof, especially its hydrochloride; palonosetron and pharmaceutically acceptable salts and solvates thereof, especially its hydrochloride; domperidone and pharmaceutically acceptable salts and solvates thereof, especially its maleate; chlorpromazine and pharmaceutically acceptable salts and solvates thereof, especially its hydrochloride; prochlorperazine and its salts and solvates, especially its dimaleate and dimesylate; promethazine and pharmaceutically acceptable salts and solvates thereof, especially its hydrochloride; metoclopramide and pharmaceutically acceptable salts and solvates thereof, especially its hydrochloride monohydrate; bromopride and pharmaceutically acceptable salts and solvates thereof, especially its monohydrochloride or the dihydrochloride monohydrate; alizapride and pharmaceutically acceptable salts and solvates thereof, especially its hydrochloride; clebopride and pharmaceutically acceptable salts and solvates thereof, especially its malate and the hydrochloride monohydrate; meclizine (meclozine) and pharmaceutically acceptable salts and solvates thereof, especially its hydrochloride monohydrate; promethazine and pharmaceutically acceptable salts and solvates thereof, especially its hydrochloride; chlorpromazine and pharmaceutically acceptable salts and solvates thereof, especially its hydrochloride; prochlorperazine and pharmaceutically acceptable salts and solvates thereof, especially its dimaleate, its dimesylate and its the 1,2-ethanedisulfonate (1:1) (edisilate); hydroxyzine and pharmaceutically acceptable salts and solvates thereof such as the dihydrochloride or the 1,1'-methylene bis(2-hydroxy-3-naphthalenecarboxylic acid (pamoate); dronabinol; nabilone; aprepitant; netupitant, rolapitant; and casopitant.

In the combination of the present invention, the non-anticholinergic antiemetic agent, Component (b) is present in an amount of from 50% to 600%, normally 50% to 300%, of the amount of the said non-anticholinergic antiemetic agent contained as a sole active ingredient in the currently used brand or generic drugs. Each of said typical non-anticholinergic antiemetic agents is present, in admixture with a pharmaceutical carrier or vehicle, in a pharmaceutical composition in dosage unit form, as Component (b), in an amount ranging from 50% of the minimum amount to 600%, and in some cases beyond 600%, advantageously from 50% to 300%, normally from 100% to 300%, of the maximum amount of said typical non-anticholinergic antiemetic agent contained in the corresponding, currently used generic or brand drug for its antiemetic indication in IR form. Advantageously, the currently used brand or generic drugs containing the maximum amount of said naAEA may be used as Component (b) of the combination of the present invention.

Advantageous naAEA in said Component (b) is selected from the group consisting of alosetron and pharmaceutically acceptable salts and solvates thereof, in particular the hydrochloride, in an amount (in alosetron) of from 0.25 mg to 6 mg; azasetron and pharmaceutically acceptable salts and solvates thereof, in particular the hydrochloride, in an amount (in azasetron) of from 5 mg to 60 mg; dolasetron and pharmaceutically acceptable salts and solvates thereof, in particular the mesylate, in an amount (in dolasetron) of from 25 mg to 600 mg; granisetron and pharmaceutically acceptable salts and solvates thereof, in particular the hydrochloride, in an amount (in granisetron) of from 0.5 mg to 6 mg; ondansetron and pharmaceutically acceptable salts and solvates thereof, in particular the hydrochloride dihydrate, in an amount (in ondansetron) of from 2 mg to 64 mg; palonosetron and pharmaceutically acceptable salts and solvated thereof, in particular its hydrochloride, in an amount (in palonosetron) of from 0.25 mg to 3 mg; ramosetron and pharmaceutically acceptable salts and solvates thereof, in particular its hydrochloride, in an amount (in ramosetron) of from 0.0125 mg to 0.3 mg; tropisetron and pharmaceutically acceptable salts and solvates thereof, in particular the hydrochloride, in an amount of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine and pharmaceutically acceptable salts and solvates thereof, in particular the hydrochloride, in an amount (in chlorpromazine) of from 12.5 mg to 600 mg; prochlorperazine and pharmaceutically acceptable salts and solvates thereof, in particular the dimaleate, in an amount (in prochlorperazine) of from 2.5 mg to 30 mg; metoclopramide and pharmaceutically acceptable salts and solvates thereof, in particular the monohydrochloride monohydrate, in an amount (in metoclopramide) of from 5 mg to 60 mg; bromopride and pharmaceutically acceptable salts and solvates, in particular the monohydrochloride and the dihydrochloride monohydrate, in an amount (in bromopride) of from 5 mg to 60 mg; clebopride and pharmaceutically acceptable salts and solvates thereof, in particular the hydrogen malate and the hydrochloride monohydrate, in an amount (in clebopride) of from 0.25 mg to 3 mg; levosulpiride, in an amount of from 12.5 mg to 600 mg; alizapride and pharmaceutically acceptable salts thereof, in particular the hydrochloride, in an amount (in alizapride) of from 25 mg to 300 mg; trimethobenzamide and pharmaceutically acceptable salts thereof such as the monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine and pharmaceutically acceptable salts and solvates thereof, in particular the hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg; in a pharmaceutical composition in admixture with a pharmaceutical carrier.

According to an embodiment, the non-anticholinergic antiemetic is present, in an IR unit form, in an amount ranging from 50% to 200% of the maximum amount of said antiemetic agent contained in the currently administered IR dosage unit forms for the treatment of the above-cited disorders or, in an ER unit form, in an amount ranging from 75% to 300% of the maximum amount of said antiemetic agent contained in the currently administered IR dosage unit forms for the treatment of the above-cited disorders.

For example, according to this embodiment, among the advantageous non-anticholinergic antiemetic agents used as Component (b), in said composition ondansetron or a pharmaceutically acceptable salt or solvate thereof, in particular its hydrochloride dihydrate, is present in an amount (in ondansetron) of from 4 mg to 16 mg per dosage unit in an IR unit form or in an amount of from 6 mg to 48 mg, preferably from 16 mg to 32 mg, in an ER unit form; alosetron or a pharmaceutically acceptable salt thereof, in particular its hydrochloride, is present in an amount (in alosetron) of from 0.5 mg to 2 mg per dosage unit in an IR unit form or in an amount of from 0.75 mg to 3 mg, in an ER unit form; azasetron or a pharmaceutically acceptable salt thereof, in particular its hydrochloride, is present in an amount of from 5 mg to 20 mg per dosage unit in an IR unit form or in an amount of from 7.5 mg to 30 mg, preferably from 10 mg to 30 mg, in an ER unit form; ramosetron or a pharmaceutically acceptable salts thereof, in particular its hydrochloride, is present in an amount (in ramosetron) of from 0.025 mg to 0.1 mg per dosage unit in an IR unit form or in an amount of from 0.0375 mg to 0.3 mg, preferably from 0.05 mg to 0.3 mg, in an ER unit form; tropisetron or a pharmaceutically acceptable salt thereof, in particular its hydrochloride, is present in an amount (in tropisetron) of from 2.5 mg to 10 mg per dosage unit in an IR unit form or in an amount of from 3.75 mg to 15 mg, preferably from 5 mg to 15 mg, in an ER unit form; granisetron or a pharmaceutically acceptable salt thereof, in particular its hydrochloride, is present in an amount (in granisetron) of from 1 mg to 4 mg per dosage unit in an IR unit form or in an amount of from 1.5 mg to 6 mg, in an ER unit form; dolasetron, or a pharmaceutically acceptable salt thereof, in particular its mesilate, is present in an amount (in dolasetron) of from 50 mg to 200 mg per dosage unit in an IR unit form or in an amount of from 75 mg to 300 mg, in an ER unit form; palonosetron, or a pharmaceutically acceptable salt thereof, in particular its hydrochloride, is present (a) in an amount (in palonosetron) of from 0.25 mg to 1 mg in an IR dosage unit form or from 0.375 mg to 1.5 mg in an ER dosage unit form, or (b) in an amount (in palonosetron) of from 0.25 mg to 12 mg, in a fixed-dose combination with netupitant, in an amount of from 200 mg to 600 mg, said fixed-dose combination being in an IR dosage unit form; rolapitant, in an amount of form 30 mg to 120 mg, in an IR dosage unit form or in an amount of from 45 mg to 180 mg in an ER dosage unit form; domperidone or a pharmaceutically acceptable salt thereof, in particular its maleate, is present in an amount (in domperidone) of from 5 mg to 20 mg per dosage unit in an IR unit form or in an amount of from 7.5 mg to 30 mg, preferably from 10 mg to 30 mg, in an ER unit form; metoclopramide or a pharmaceutically acceptable salt or solvate thereof, in particular its monohydrochloride monohydrate, is present in an amount (in metoclopramide) of from 5 mg to 20 mg per dosage unit in an IR unit form or in an amount of from 7.5 mg to 30 mg, preferably from 10 mg to 30 mg, in an ER unit form; alizapride or a pharmaceutically acceptable salt thereof, in particular its hydrochloride, is present in an amount (in alizapride) of from 25 mg to 100 mg per dosage unit in an IR unit form or in an amount of from 37.5 mg to 300 mg, preferably from 100 mg to 300 mg, in an ER unit form; meclizine or a pharmaceutically acceptable salt thereof, in particular its hydrochloride is present in an amount (in meclizine) of from 25 mg to 100 mg per dosage unit in an IR unit form or in an amount of from 37.5 mg to 150 mg, preferably from 50 mg to 150 mg, in an ER unit form; chlorpromazine or a pharmaceutically acceptable salt thereof, in particular its hydrochloride is present in an amount (in chlorpromazine) of from 50 mg to 200 mg per dosage unit in an IR unit form or in an amount of from 75 mg to 300 mg, preferably from 100 mg to 300 mg, in an ER unit form; prochlorperazine or a pharmaceutically acceptable salt thereof, in particular its maleate is present in an amount (in prochlorperazine) of from 2.5 mg to 10 mg per dosage unit in an IR unit form or in an amount of from 3.75 mg to 15 mg, preferably from 5 mg to 15 mg, in an ER unit form; dronabinol is present in an amount of from 5 mg to 20 mg per dosage unit in an IR unit form or in an amount of from 7.5 mg to 30 mg, preferably from 10 mg to 30 mg, in an ER unit form; nabilone is present in an amount of from 0.5 mg to 2 mg per dosage unit in an IR unit form or in an amount of from 0.75 mg to 3 mg per dosage unit in an ER unit form; aprepitant is present in an amount of from 62.5 mg to 250 mg per dosage unit in an IR unit form or in an amount of from 93.75 mg to 325 mg, preferably from 125 mg to 325 mg, in an ER unit form; netupitant is present in an amount of from 150 mg to 600 mg, in an IR unit form or in an amount of from 225 to 900 mg, preferably from 300 mg to 900 mg, in an ER unit form; rolapitant, in an amount of form 30 mg to 120 mg, in an IR unit form or in an amount of from 45 mg to 180 mg, preferably from 60 mg to 180 mg, in an ER unit form; and casopitant is present in an amount of from 25 mg to 100 mg per dosage unit in an IR unit form or in an amount of from 37.5 mg to 150, preferably from 50 mg to 150 mg, in an ER unit form, in admixture with a pharmaceutical composition in dosage unit form.

Preferred Component (b) is a pharmaceutical composition in dosage unit form comprising a non-anticholinergic antiemetic agent selected from the group consisting of ondansetron and pharmaceutically acceptable salts and solvates thereof, in an amount (in ondansetron) of from 8 mg to 24 mg; granisetron and pharmaceutically acceptable salts and solvates thereof, in an amount (in granisetron) of from 1 mg to 3 mg; domperidone and pharmaceutically acceptable salts and solvates thereof, in an amount (in domperidone) of from 10 mg to 30 mg; metoclopramide and pharmaceutically acceptable salts and solvates thereof, in an amount (in metoclopramide) of from 10 mg to 30 mg; dronabinol, in an amount of from 10 mg to 30 mg; nabilone, in an amount of from 1 mg to 3 mg; aprepitant, in an amount of from 125 mg to 375 mg; netupitant, in an amount of from 300 mg to 900 mg; rolapitant, in an amount of form 60 mg to 180 mg; and casopitant, in an amount of from 50 mg to 150 mg, in admixture with a pharmaceutical carrier.

Ondansetron may also be used as formulated in a patch, for example as described by Farsiya Fathima et al. in Research in J. Pharm. And Tech. 4,4(5), May 2011, 806-814: "Formulation and Evaluation of Matrix-Type Transdermal Delivery System of Ondansetron Hydrochloride Using Solvent Casting Technique", or by Cho, J., Van Duong, A., Nguyen, L. T. T. et al. in Journal of Pharmaceutical Investigation (2016). doi: 10.1007/s40005-016-0273-9, published online on 18 Aug. 2016: "Design of transdermal matrix patch containing ondansetron".

The Donepezil Component (c)

According to the present invention, donepezil or a pharmaceutically acceptable salts thereof Component (c) is present in the combination in an amount that is equivalent to 10 mg to 92 mg, preferably from 20 mg to 92 mg, normally from 10 mg to 70 mg, preferably from 20 mg to 70 mg of donepezil hydrochloride and is administered to a patient at a daily dose that is equivalent to 10 mg to 92 mg, preferably from 20 mg to 92 mg, normally from 10 mg to 70 mg, preferably from 20 mg to 70 mg of donepezil hydrochloride. Donepezil hydrochloride may be administered as a brand product, at multiple 5-mg. 10-mg, or 23 mg doses, but, in view of the high doses to be administered, it will be manufactured in new pharmaceutical compositions comprising the above donepezil amounts, in particular an amount of from 20 mg to 92 mg donepezil hydrochloride.

Donepezil hydrochloride may be also used as a brand product, by orally administering one or more ARICEPT® immediate-release 5 mg-10 mg-tablets or, where available, 23 mg-tablets. In particular, donepezil hydrochloride may be orally administered, in combination with the above-illustrated memantine/solifenacin/naAEA combination, at a daily dose of from 10 mg to 92 mg, preferably from 20 mg to 92 mg, normally from 10 mg to 70 mg, preferably from 20 mg to 70 mg.

According to particular necessities, in particular for use in the titration phase of the therapy, the donepezil effective amount that is present in the above combinations, including the fixed-dose combinations, may be from 10 mg to 50 mg, in particular of 10 mg, 15 mg, 20 mg, 25 mg, 30 mg, 35 mg, 40 mg, and 50 mg.

The Solifenacin Component (b) or (d)

Solifenacin and pharmaceutically acceptable salts and compounds thereof, including the quaternary ammonium salts thereof, and their preparation are described in U.S. Pat. No. 6,017,927, the disclosure of which is incorporated herein in its entirety by reference. Methods for the preparation and for the purification of solifenacin and its salts, in particular of solifenacin succinate, are described for example in WO 2007/076116, WO 2009/139002, WO 2011/003624 and WO 2012/001481, the disclosures of which are incorporated herein in their entirety by reference, the disclosures of which are incorporated herein for reference in their entirety.

According to the present invention, solifenacin or a pharmaceutically acceptable salts thereof Component (d) is present in the combination in an amount that is equivalent to from 10 mg to 30 mg, advantageously from 15 mg to 25 mg, preferably 15 mg of solifenacin succinate and is administered to a patient at a daily dose that is equivalent to from 10 mg to 30 mg, advantageously from 15 mg to 25 mg, preferably 15 mg, of solifenacin succinate. Solifenacin succinate may be administered as a brand product (VESIcare® 5-mg and 10.mg) in multiple 5-mg or 10-mg doses.

In particular:

memantine or a pharmaceutically acceptable salt thereof (Component (a)) is in a pharmaceutical composition in dosage unit form, in an amount that is equivalent to from 5 mg to 30 mg of memantine hydrochloride, in admixture with a pharmaceutical carrier; and solifenacin or pharmaceutically acceptable salt thereof (Component (b)) is in a pharmaceutical composition in dosage unit form, in an amount that is equivalent to from 10 mg to 30 mg of solifenacin succinate, in admixture with a pharmaceutical carrier.

The Combinations

As set forth above, by treating a patient suffering from a hypocholinergic disorder, as hereinabove defined, with a donepezil/solifenacin combination, said patient concomitantly also taking memantine, the addition of an anticholinergic antiemetic agent to said memantine, especially as a memantine/naAEA fixed-dose combination, assures a safe treatment and allows for the increase of the donepezil doses without any appearance of cholinergic effects.

Thus, in a first embodiment, the present invention provides a pharmaceutical combination comprising, as Components, (a) memantine or a pharmaceutically acceptable salt thereof; and (b) a non-anticholinergic antiemetic agent.

In said combination, said memantine or a pharmaceutically acceptable salt thereof Component (a) preferably is in a pharmaceutical composition in dosage unit form, in an amount that is equivalent to from 5 mg to 30 mg of memantine hydrochloride, in admixture with a pharmaceutical carrier; and said naAEA Component (b) also is in a pharmaceutical composition in dosage unit form, in admixture with a pharmaceutical carrier.

Any of the non-anticholinergic antiemetic agents illustrated in the above "The non-anticholinergic Antiemetic Agent Component (b)" section may be used according to the present invention. Normally, the naAEA is selected form the group consisting of (b1) 5HT3-antagonists, (b2) DA-antagonists, (b3) H1-antagonists, (b4) cannabinoids, and (b5) NK1-antagonists According to a first aspect of this first embodiment, said combination is a fixed-dose combination essentially consisting of a pharmaceutical composition in dosage unit form comprising (a) memantine or a pharmaceutically acceptable salt thereof, in an amount that is equivalent to from 5 mg to 30 mg, preferably from 7 mg to 28 mg, of memantine hydrochloride; and (b) a naAEA selected from the group consisting of alosetron and pharmaceutically acceptable salts and solvates thereof, in particular the hydrochloride, in an amount (in alosetron) of from 0.25 mg to 6 mg; azasetron and pharmaceutically acceptable salts and solvates thereof, in particular the hydrochloride, in an amount (in azasetron) of from 5 mg to 60 mg; dolasetron and pharmaceutically acceptable salts and solvates thereof, in particular the mesylate, in an amount (in dolasetron) of from 25 mg to 600 mg; granisetron and pharmaceutically acceptable salts and solvates thereof, in particular the hydrochloride, in an amount (in granisetron) of from 0.5 mg to 6 mg; ondansetron and pharmaceutically acceptable salts and solvates thereof, in particular the hydrochloride dihydrate, in an amount (in ondansetron) of from 2 mg to 64 mg; palonosetron and pharmaceutically acceptable salts and solvated thereof, in particular its hydrochloride, in an amount (in palonosetron) of from 0.25 mg to 3 mg; ramosetron and pharmaceutically acceptable salts and solvates thereof, in particular its hydrochloride, in an amount (in ramosetron) of from 0.0125 mg to 0.3 mg; tropisetron and pharmaceutically acceptable salts and solvates thereof, in particular the hydrochloride, in an amount of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine and pharmaceutically acceptable salts and solvates thereof, in particular the hydrochloride, in an amount (in chlorpromazine) of from 12.5 mg to 600 mg; prochlorperazine and pharmaceutically acceptable salts and solvates thereof, in particular the dimaleate, in an amount (in prochlorperazine) of from 2.5 mg to 30 mg; metoclopramide and pharmaceutically acceptable salts and solvates thereof, in particular the monohydrochloride monohydrate, in an amount (in metoclopramide) of from 5 mg to 60 mg; bromopride and pharmaceutically acceptable salts and solvates, in particular the monohydrochloride and the dihydrochloride monohydrate, in an amount (in bromopride) of from 5 mg to 60 mg; clebopride and pharmaceutically acceptable salts and solvates thereof, in particular the hydrogen malate and the hydrochloride monohydrate, in an amount (in clebopride) of from 0.25 mg to 3 mg; levosulpiride, in an amount of from 12.5 mg to 600 mg; alizapride and pharmaceutically acceptable salts thereof, in particular the hydrochloride, in an amount (in alizapride) of from 25 mg to 300 mg; trimethobenzamide and pharmaceutically acceptable salts thereof such as the monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine and pharmaceutically acceptable salts and solvates thereof, in particular the hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg, in admixture with a pharmaceutical carrier or vehicle.

An advantageous new memantine/ondansetron fixed-dose combination essentially consists of (a) memantine or a pharmaceutically acceptable salt thereof, in amount that is equivalent to from 5 mg to 30 mg of memantine hydrochloride; and (b) a naAEA selected from the group consisting of ondansetron and pharmaceutically acceptable salts and solvates thereof, in an amount (in ondansetron) of from 4 mg to 64 mg, in admixture with a pharmaceutical carrier or vehicle.

A specific new memantine/ondansetron fixed-dose combination according to this advantageous aspect of this first embodiment of the present invention essentially consists of (a) memantine or a pharmaceutically acceptable salt thereof, in amount that is equivalent to from 5 mg to 10 mg of memantine hydrochloride; and (b) a naAEA selected from the group consisting of ondansetron and pharmaceutically acceptable salts and solvates thereof, in an amount (in ondansetron) of from 4 mg to 32 mg, in admixture with a pharmaceutical carrier or vehicle in an IR-formulation.

Another specific new memantine/ondansetron fixed-dose combination according to this first embodiment of the present invention essentially consists of (a) memantine or a pharmaceutically acceptable salt thereof, in amount that is equivalent to from 7 mg to 28 mg of memantine hydrochloride; and (b) a naAEA selected from the group consisting of ondansetron and pharmaceutically acceptable salts and solvates thereof, in particular the hydrochloride dihydrate, in an amount (in ondansetron) of from 16 mg to 64 mg, in admixture with a pharmaceutical carrier or vehicle in an ER-formulation.

Components (a/b), (c) and (d) may be concurrently or sequentially administered once per day to said patient suffering from said hypocholinergic disorder. This treatment may improve the conditions of said patient and allows, in particular, an improvement of the cognitive function due to a neuroprotection induced by said treatment.

In a further first embodiment, the present invention provides a pharmaceutical combination comprising, as Components, (c) memantine or a pharmaceutically acceptable salt thereof; and (d) solifenacin or a pharmaceutically acceptable salt thereof.

According to the present invention, memantine or pharmaceutically acceptable salts thereof is present in the combination in an amount of from 5 mg to 30 mg, preferably from 7 mg to 28 mg, and is administered to a patient at a daily dose that is equivalent to from 7 mg to 28 mg of memantine hydrochloride.

Memantine may also be administered in its brand formulations, as 10-mg IR form (Namenda®), or 7 mg-28 mg ER-forms. (Namenda® RX)

According to this first embodiment of present invention, solifenacin or pharmaceutically acceptable salts thereof is present in the combination in an amount that is equivalent to from 10 mg to 30 mg, advantageously from 15 mg to 25 mg, preferably 15 mg, of solifenacin succinate and is administered to a patient at a daily dose that is equivalent to from 10 mg to 30 mg, advantageously from 15 mg to 25 mg, preferably 15 mg of solifenacin succinate. Solifenacin succinate may be administered as a brand product (VESIcare® 5-mg and 10.mg) in multiple 5-mg or single or multiple 10-mg doses.

Donepezil or a pharmaceutically acceptable salt may be present in the combination in an amount that is equivalent to from 10 mg to 92 mg, preferably from 20 mg to 92 mg, normally from 10 mg to 70 mg, preferably from 20 mg to 70 mg, as illustrated above. Donepezil hydrochloride may be administered as brand product (Aricept®) in multiple 5 mg-10 mg- and, where available, 23 mg-unit forms. A memantine/donepezil fixed-dose combination, known as Namzaric®, may also be used according to the present invention.

In particular:

memantine or a pharmaceutically acceptable salt thereof [Component (a)] is in a pharmaceutical composition in dosage unit form, in an amount that is equivalent to from 5 mg to 30 mg, advantageously from 15 mg to 25 mg, of memantine hydrochloride, in admixture with a pharmaceutical carrier; and solifenacin or pharmaceutically acceptable salt thereof [(Component (b)] is in a pharmaceutical composition in dosage unit form, in an amount that is equivalent to from 10 mg to 30 mg, advantageously from 15 mg to 25 mg, of solifenacin succinate, in admixture with a pharmaceutical carrier.

In the memantine/solifenacin combination of the present invention, solifenacin, as its succinate salt, may be administered in oral immediate-release form, by using a brand IR-unit form containing 10 mg of solifenacin succinate or multiple doses of its brand 5-mg or 10-mg IR-unit forms.

According to an advantageous aspect of this first embodiment, the memantine/solifenacin combination consists of:

a pharmaceutical composition comprising memantine hydrochloride, in an amount of from 7 mg to 28 mg in admixture with a pharmaceutical carrier in an ER-form, as Component (a); and a pharmaceutical composition comprising solifenacin succinate, in an amount of from 10 mg to 30 mg, advantageously from 15 mg to 25 mg, in admixture with a pharmaceutical carrier in an IR-unit form, as Component (b).

According to a preferred aspect of this first embodiment, the memantine/solifenacin combination is a fixed-dose combination essentially consisting of a pharmaceutical composition comprising (a) memantine or a pharmaceutically acceptable salt thereof, in an amount that is equivalent to from 5 mg to 30 mg of memantine hydrochloride; and (b) solifenacin or a pharmaceutical acceptable salt thereof, in an amount is equivalent to from 10 mg to 30 mg, advantageously from 15 mg to 25 mg, of solifenacin succinate, in admixture with a pharmaceutical carrier or vehicle.

All the aforementioned pharmaceutical compositions are preferably in dosage unit form wherein each of the active ingredients or both of them are formulated in admixture with a pharmaceutical carrier, and optimized, as is known in the art, for their pharmaceutical and therapeutic use.

In a preferred embodiment, the memantine/solifenacin combination consists of:

a pharmaceutical composition comprising memantine hydrochloride, in an amount of from 7 mg to 28 mg in admixture with a pharmaceutical carrier in an ER-form, as Component (a); and a pharmaceutical composition comprising solifenacin succinate, in an amount of from 10 mg to 30 mg, in admixture with a pharmaceutical carrier in an IR-unit form, as Component (b).

In particular, the invention provides a pharmaceutical composition in dosage unit form, which comprises (a) memantine hydrochloride, in an amount of from 5 mg to 30 mg; and (b) solifenacin succinate, in an amount of from 10 mg to 30 mg, advantageously from 15 mg to 25 mg, preferably 15 mg, in admixture with a pharmaceutical carrier or vehicle.

The pharmaceutical carrier or vehicles are those commonly used for the preparation of compositions for oral, buccal and parenteral, in particular transdermal, administration. Appropriate unit forms comprise the oral forms such as tablets, soft or hard gelatine capsules, powders or granulates in sachets and suitably measured oral solutions or suspensions as well as patches for transdermal administration.

In said unit form memantine, preferably memantine hydrochloride, and solifenacin, especially solifenacin succinate, are mixed, together or separately, according to known technologies, in admixture with a pharmaceutical carriers or vehicles, in pharmaceutical compositions.

Carrier or vehicles for IR tablets include for example starches, cellulose and derivatives thereof; lubricants such as talc, stearic acid or magnesium stearate; diluents such as talc, powdered cellulose, lactose, starches such as maize or corn starch, mannitol, sorbitol; disaggregating agents such as microcrystalline cellulose or crospovidone; lubricants such as polyethylene glycol or magnesium stearate; ligands such as methylcellulose, sodium carboxymethylcellulose, alginic acid, alginates; sweeteners, such as saccharose, dextrose, mannitol, saccharin; or flavoring agents such as natural or synthetic oils.

Carriers or vehicles for orally disintegrating tablets include for example lubricants, aggregating, sweetening, flavoring or disaggregating agents as well as agents improving the buccal mucosa absorption of Component (a) and/or Component (b) such as sorbitol, mannitol, lactose and cellulose.

Carriers or vehicles for liquid, normally aqueous, suspensions or solutions include for example antioxidants, such as sodium metabisulfite or sodium sulfite, thickening agents, such as microcrystalline cellulose, hydroxypropylcellulose, carboxymethylcellulose or polyvinylpyrrolidone, presevatives such as methyl paraben, ethyl paraben, tetra-sodium ethylenediaminotetracetate (sodium edentate), sodium benzoate or an alkaline salt of sorbic acid, as well as flavoring and sweetening agents.

The sweeteners contained in the orally disintegrating tablets and the liquid suspensions or solutions may be natural, optional reduced sugars such as sucrose, dextrose, xylitol, mannitol or sorbitol, or synthetic product such as sodium saccharine or aspartame.

The flavoring agents are pharmaceutically acceptable flavors and tastes of synthetic and natural oils, the latter extracted from plants, leaves, flowers, fruits and their combinations, such as cinnamon, peppermint, anise and citron leaves, bitter almond, citrus fruits, in particular orange and/or lemon, linden and grapefruit oils. Also chocolate, vanilla or eucalyptus flavor and essences of fruit, in particular apple, pear, peach, strawberry, cherry, apricot, orange, lemon and grapes may be advantageously used.

Component (a) and Component (b) are advantageously combined in a fixed dose combination for the simultaneous administration of the two Components. These fixed-dose combinations are in pharmaceutical unit forms wherein Component (a) and Component (b) are present, together or separately, in admixture with a pharmaceutical carrier or vehicle. In these unit forms, memantine or a pharmaceutically acceptable salt thereof, especially its hydrochloride, and solifenacin or a pharmaceutically acceptable salt thereof, especially its succinate, are present in an IR- or ER-formulation.

A pharmaceutical unit form comprising (a) memantine hydrochloride, in a pharmaceutical composition comprising said memantine hydrochloride in an amount of from 5 mg to 30 mg, in admixture with a pharmaceutical carrier in extended-release formulation; and (b) solifenacin succinate, in a pharmaceutical composition comprising said solifenacin succinate in an amount of from 10 mg to 30 mg, advantageously from 15 mg to 25 mg, in admixture with a pharmaceutical carrier or vehicle in an immediate release formulation, is particularly advantageous.

For oral use, Component (a) and Component (b) are in compositions in admixture with pharmaceutical excipients in known formulations wherein said Components are mixed together or separated, for example in two tablets introduced in a capsule, as described in as described in GB 1204580, the disclosure of which is incorporated herein for reference, or in a two-compartment capsule or in a multilayer (bilayer) tablet wherein the two components are both in IR form or wherein the memantine pharmaceutically acceptable salt, especially the hydrochloride, is in ER-form, and the solifenacin pharmaceutically acceptable salt, especially the succinate thereof, is in IR-form, according to the technologies disclosed in U.S. Pat. No. 7,303,761 or 8,802,143, the disclosures of which are incorporated herein in their entirety for reference.

Component (a) and Component (b) may also be present in form of one of their complexes with a cyclodextrin, for example α-cyclodextrin, β-cyclodextrin, γ-cyclodextrin, 2-hydroxypropyl-β-cyclodextrin or methyl-β-cyclodextrin.

Component (a) and Component (b) may also be formulated in the form of microcapsules, optionally with one or more carriers or vehicles or additives.

For oral administration, Component (a) and Component (b), together or separately, are formulated by mixing the active ingredient with conventional pharmaceutical acceptable carriers or vehicles enabling said active ingredients to be formulated in tablets, dragees, orally disintegrating tablets, capsules, liquid solutions or suspensions, syrups and the like.

The composition according to the present invention may be in form of a capsule containing two tablets as described herein above, one of them comprising Component (a) and the other comprising Component (b).

The composition of memantine/solifenacin may be formulated in tablets in which one or both of the two components is in controlled-release form, for example as a dispersion of said component in hydroxypropyl-methyl-cellulose or in a film-coated microgranule.

Advantageously, memantine, preferably memantine hydrochloride in an ER-formulation and in an amount of 7 mg to 28 mg, is in the core, and solifenacin, preferably solifenacin succinate, in IR-formulation and in an amount of from 10 mg to 30 mg, advantageously from 15 mg to 25 mg, is in the outer layer in a bilayer tablet in which, both the core and the outer layer may be coated with a film.

The memantine/solifenacin fixed-dose combination according to the present invention may be also formulated in a bi-layer tablet, the first layer containing memantine or a pharmaceutically acceptable salt thereof and the second one containing solifenacin or a pharmaceutically acceptable salt thereof. A third layer, free of active substances, could be inserted between said first and said second layer.

In said fixed dose combination, the retardant material of said first layer and the immediate release carrier second layer are two elements selected in order to allow respectively an extended (or sustained) release delivery of the memantine pharmaceutically acceptable salts, normally the hydrochloride, and to provide the solifenacin pharmaceutically acceptable salt, normally the succinate, in admixture with a pharmaceutical carrier for immediate release, for example according to the technologies described in U.S. Pat. No. 7,303,761 or in U.S. Pat. No. 8,802,143, the disclosures of which are incorporated herein in their entirety.

An advantageous composition according to this first embodiment consists of

Layer A, comprising from 7 mg to 28 mg of memantine hydrochloride Component (a) in admixture with a pharmaceutical carrier or vehicle in a ER formulation; and Layer B, comprising from 10 mg to 30 mg, advantageously from 15 mg to 25 mg, preferably 15 mg, of solifenacin succinate Component (b), in admixture with a pharmaceutical carrier or vehicle in an IR-formulation, said composition being destined to be administered once per day, in combination with a pharmaceutical composition comprising from 10 mg to 92 mg, advantageously from 20 mg to 92 mg, normally from 10 mg to 70 mg, preferably from 20 mg to 70 mg of donepezil hydrochloride, also destined to be administered once per day.

Carriers or vehicles and vehicles for ER tablets include retardant materials such as is acrylic and methacrylic acid polymers and copolymers; cellulose derivatives such as hydroxypropylmethylcellulose, hydroxyethylcellulose, hydroxypropylethylcellulose, hydroxypropylcelluloses, methylcellulose, ethylcellulose, or sodium carboxymethylcellulose; gums; waxes; glycerides or aliphatic alcohols or a mixture thereof. Thus, a second aspect of this first embodiment of the present invention provides the above-illustrated memantine/naAEA combinations for use for the treatment of a patient suffering from a hypocholinergic disorder in combination with (c) donepezil or a pharmaceutically acceptable salt thereof, at a daily dose that is equivalent to from 10 mg to 92 mg, preferably from 20 mg to 92 mg, normally from 10 mg to 70 mg, preferably from 20 mg to 70 mg mg of donepezil hydrochloride; and (d) solifenacin or a pharmaceutically acceptable salt thereof, at a daily dose, that is equivalent to from 10 mg to 30 mg, normally from 15 mg to 25 mg, preferably of 15 mg of solifenacin succinate.

For the intended use, donepezil or pharmaceutically acceptable salt Component (c) is formulated in a pharmaceutical composition comprising said Component (c) in an amount that is equivalent to from 10 mg to 92 mg, preferably from 20 mg to 92 mg, normally from 10 mg to 70 mg, preferably from 20 mg to 70 mg, of donepezil hydrochloride, in admixture with a pharmaceutical carrier of vehicle preferably in a IR formulation The pharmaceutical composition comprising Component (c) consisting of donepezil hydrochloride may be a generic or brand (for example Aricept®) formulation to be used in single or multiple 5-mg, 10-mg or, where available, 23-mg unit forms.

For the intended use, solifenacin or pharmaceutically acceptable salt Component (d) is formulated in a pharmaceutical composition comprising said Component (d) in an amount that is equivalent to from 10 mg to 30 mg of solifenacin succinate, in admixture with a pharmaceutical carrier of vehicle in a IR formulation.

The pharmaceutical composition comprising Component (d) consisting of solifenacin succinate may be a generic or brand (for example VESIcare®) formulation to be used in multiple 5-mg or single or multiple 10-mg unit forms. According to a third aspect of this first embodiment, the present invention provides a method for the treatment of a hypocholinergic disorder, which comprises treating a patient in need of said treatment with a combination comprising an effective amount of a N-methyl-D-aspartate receptor antagonist Component (a) selected from the group consisting of memantine and pharmaceutical acceptable salts thereof and an effective amount of a naAEA Component (b), in further combination with (c) donepezil or a pharmaceutically acceptable salt thereof, in an amount that is equivalent to from 10 mg to 92 mg of donepezil hydrochloride and;

(d) solifenacin or a pharmaceutically acceptable salt thereof, in an amount that is equivalent to from 10 mg to 30 mg of solifenacin succinate.

Said memantine or a pharmaceutically acceptable salt thereof Component (a), is administered at a daily dose that is equivalent to from 5 mg to 30 mg more particularly in an IR-formulation, at a daily dose that is equivalent to 20 mg of memantine hydrochloride or an ER-formulation, at a daily dose that is equivalent to from 7 mg to 28 mg of memantine hydrochloride.

Said memantine or a pharmaceutically acceptable salt thereof Component (a) is formulated in a pharmaceutical composition comprising said memantine or pharmaceutically acceptable salt thereof in an amount that is equivalent to from 5 mg to 30 mg, preferably from 7 mg to 28 mg of memantine hydrochloride, in admixture with a pharmaceutical carrier or vehicle. Said pharmaceutical composition comprising memantine hydrochloride may be the brand products known as Namenda® and Namenda®XR.

Said naAEA Component (b) is formulated in a pharmaceutical composition in dosage unit form comprising a naAEA selected from the group consisting of alosetron and pharmaceutically acceptable salts and solvates thereof, in particular the hydrochloride, in an amount (in alosetron) of from 0.25 mg to 6 mg; azasetron and pharmaceutically acceptable salts and solvates thereof, in particular the hydrochloride, in an amount (in azasetron) of from 5 mg to 60 mg; dolasetron and pharmaceutically acceptable salts and solvates thereof, in particular the mesylate, in an amount (in dolasetron) of from 25 mg to 600 mg; granisetron and pharmaceutically acceptable salts and solvates thereof, in particular the hydrochloride, in an amount (in granisetron) of from 0.5 mg to 6 mg; ondansetron and pharmaceutically acceptable salts and solvates thereof, in particular the hydrochloride dihydrate, in an amount (in ondansetron) of from 2 mg to 64 mg; palonosetron and pharmaceutically acceptable salts and solvated thereof, in particular its hydrochloride, in an amount (in palonosetron) of from 0.25 mg to 3 mg; ramosetron and pharmaceutically acceptable salts and solvates thereof, in particular its hydrochloride, in an amount (in ramosetron) of from 0.0125 mg to 0.3 mg; tropisetron and pharmaceutically acceptable salts and solvates thereof, in particular the hydrochloride, in an amount of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine and pharmaceutically acceptable salts and solvates thereof, in particular the hydrochloride, in an amount (in chlorpromazine) of from 12.5 mg to 600 mg; prochlorperazine and pharmaceutically acceptable salts and solvates thereof, in particular the dimaleate, in an amount (in prochlorperazine) of from 2.5 mg to 30 mg; metoclopramide and pharmaceutically acceptable salts and solvates thereof, in particular the monohydrochloride monohydrate, in an amount (in metoclopramide) of from 5 mg to 60 mg; bromopride and pharmaceutically acceptable salts and solvates, in particular the monohydrochloride and the dihydrochloride monohydrate, in an amount (in bromopride) of from 5 mg to 60 mg; clebopride and pharmaceutically acceptable salts and solvates thereof, in particular the hydrogen malate and the hydrochloride monohydrate, in an amount (in clebopride) of from 0.25 mg to 3 mg; levosulpiride, in an amount of from 12.5 mg to 600 mg; alizapride and pharmaceutically acceptable salts thereof, in particular the hydrochloride, in an amount (in alizapride) of from 25 mg to 300 mg; trimethobenzamide and pharmaceutically acceptable salts thereof such as the monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine and pharmaceutically acceptable salts and solvates thereof, in particular the hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg, in admixture with a pharmaceutical carrier or vehicle.

Preferably, in said pharmaceutical composition, said naAEA is selected from the group consisting of alosetron hydrochloride, in an amount (in alosetron) of from 0.25 mg to 6 mg; azasetron hydrochloride, in an amount (in azasetron) of from 5 mg to 60 mg; dolasetron mesylate, in an amount (in dolasetron) of from 25 mg to 600 mg; granisetron hydrochloride, in an amount (in granisetron) of from 0.5 mg to 6 mg; ondansetron hydrochloride dihydrate, in an amount (in ondansetron) of from 2 mg to 64 mg; hydrochloride, in an amount (in palonosetron) of from 0.25 mg to 3 mg; ramosetron hydrochloride, in an amount (in ramosetron) of from 0.0125 mg to 0.3 mg; tropisetron hydrochloride, in an amount of from 2.5 mg to 30 mg; domperidone, in an amount (in domperidone) of from 5 mg to 60 mg; haloperidol, in an amount of from 0.5 mg to 60 mg; chlorpromazine hydrochloride, in an amount (in chlorpromazine) of from 12.5 mg to 600 mg; prochlorperazine dimaleate, in an amount (in prochlorperazine) of from 2.5 mg to 30 mg; metoclopramide monohydrochloride monohydrate, in an amount (in metoclopramide) of from 5 mg to 60 mg; bromopride monohydrochloride or dihydrochloride monohydrate, in an amount (in bromopride) of from 5 mg to 60 mg; clebopride hydrogen malate or hydrochloride monohydrate, in an amount (in clebopride) of from 0.25 mg to 3 mg; levosulpiride, in an amount of from 12.5 mg to 600 mg; alizapride hydrochloride, in an amount (in alizapride) of from 25 mg to 300 mg; trimethobenzamide monohydrochloride, in an amount (in trimethobenzamide) of from 50 mg to 600 mg; meclizine, in an amount of from 6.25 mg to 300 mg; promethazine hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg, in admixture with a pharmaceutical carrier or vehicle. Any of these naAEAs preferably is in a generic or brand product, preferably in the maximum amount contained in said generic or brand product.

Another advantageous pharmaceutical composition comprising a naAEA Component (b) may be the brand product consisting of a pharmaceutical composition comprising palonosetron hydrochloride, in an amount, in palonosetron, of 0.5 mg and netupitant, in an amount of 300 mg, in admixture with a pharmaceutical carrier, known under as Akynzeo®.

In the present method, the donepezil or pharmaceutically acceptable salt Component (c) is formulated in a pharmaceutical composition comprising said Component (c) in an amount that is equivalent to from 10 mg to 92 mg, preferably from 20 mg to 92 mg, normally from 10 mg to 70 mg, preferably from 20 mg to 70 mg, of donepezil hydrochloride, in admixture with a pharmaceutical carrier of vehicle preferably in a IR formulation The pharmaceutical composition comprising Component (c) consisting of donepezil hydrochloride may be a generic or brand (for example Aricept®) formulation to be used in single or multiple 5-mg, 10-mg or, where available, 23-mg unit forms.

In the present method, the solifenacin or pharmaceutically acceptable salt Component (d) is formulated in a pharmaceutical composition comprising said Component (d) in an amount that is equivalent to from 10 mg to 30 mg of solifenacin succinate, in admixture with a pharmaceutical carrier of vehicle in a IR formulation.

The pharmaceutical composition comprising Component (d) consisting of solifenacin succinate may be a generic or brand (for example VESIcare®) formulation to be used in multiple 5-mg or single or multiple 10-mg unit forms.

According to a fourth aspect of this first embodiment, the invention provides a method for the treatment of a hypocholinergic disorder, which comprises treating a patient in need of said treatment with a fixed-dose combination essentially consisting of (a/b) a pharmaceutical composition in dosage unit form comprising
  (a) memantine or pharmaceutically acceptable salt thereof in an amount that is equivalent to from 5 mg to 30 mg, preferably from 7 mg to 28 mg of memantine hydrochloride; and
  (b) a naAEA selected from the group consisting of alosetron and pharmaceutically acceptable salts and solvates thereof, in particular the hydrochloride, in an amount (in alosetron) of from 0.25 mg to 6 mg; azasetron and pharmaceutically acceptable salts and solvates thereof, in particular the hydrochloride, in an amount (in azasetron) of from 5 mg to 60 mg; dolasetron and pharmaceutically acceptable salts and solvates thereof, in particular the mesylate, in an amount (in dolasetron) of from 25 mg to 600 mg; granisetron and pharmaceutically acceptable salts and solvates thereof, in particular the hydrochloride, in an amount (in granisetron) of from 0.5 mg to 6 mg; ondansetron and pharmaceutically acceptable salts and solvates thereof, in particular the hydrochloride dihydrate, in an amount (in ondansetron) of from 2 mg to 64 mg; palonosetron and pharmaceutically acceptable salts and solvated thereof, in particular its hydrochloride, in an amount (in palonosetron) of from 0.25 mg to 3 mg; ramosetron and pharmaceutically acceptable salts and solvates thereof, in particular its hydrochloride, in an amount (in ramosetron) of from 0.0125 mg to 0.3 mg; tropisetron and pharmaceutically acceptable salts and solvates thereof, in particular the hydrochloride, in an amount of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine and pharmaceutically acceptable salts and solvates thereof, in particular the hydrochloride, in an amount (in chlorpromazine) of from 12.5 mg to 600 mg; prochlorperazine and pharmaceutically acceptable salts and solvates thereof, in particular the dimaleate, in an amount (in prochlorperazine) of from 2.5 mg to 30 mg; metoclopramide and pharmaceutically acceptable salts and solvates thereof, in particular the monohydrochloride monohydrate, in an amount (in metoclopramide) of from 5 mg to 60 mg; bromopride and pharmaceutically acceptable salts and solvates, in particular the monohydrochloride and the dihydrochloride monohydrate, in an amount (in bromopride) of from 5 mg to 60 mg; clebopride and pharmaceutically acceptable salts and solvates thereof, in particular the hydrogen malate and the hydrochloride monohydrate, in an amount (in clebopride) of from 0.25 mg to 3 mg; levosulpiride, in an amount of from 12.5 mg to 600 mg; alizapride and pharmaceutically acceptable salts thereof, in particular the hydrochloride, in an amount (in alizapride) of from 25 mg to 300 mg; trimethobenzamide and pharmaceutically acceptable salts thereof such as the monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine and pharmaceutically acceptable salts and solvates thereof, in particular the hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in admixture with a pharmaceutical carrier or vehicle;

(c) a pharmaceutical composition in dosage unit form comprising donepezil or a pharmaceutically acceptable salt thereof, in an amount that is equivalent to from 10 mg to 92 mg of donepezil hydrochloride, in admixture with a pharmaceutical carrier or vehicle and;

(d) a pharmaceutical composition in dosage unit form comprising solifenacin or a pharmaceutically acceptable salt thereof, in an amount that is equivalent to from 10 mg to 30 mg of solifenacin succinate, in admixture with a pharmaceutical carrier or vehicle.

Said Component (c) is donepezil or a pharmaceutically acceptable salt thereof, in a pharmaceutical composition comprising said donepezil or pharmaceutically acceptable salt thereof in an amount that is equivalent to from 10 mg to 92 mg, preferably from 20 mg to 92 mg, normally from 10 mg to 70 mg, preferably from 20 mg to 70 mg of donepezil hydrochloride. Donepezil hydrochloride Component (c) may be also used as a brand product, by orally administering one or more ARICEPT® immediate-release 5 mg-10 mg-tablets or, where available, 23 mg-tablets.

Said Component (d) is solifenacin or a pharmaceutically acceptable salt thereof, in a pharmaceutical composition comprising said solifenacin or pharmaceutically acceptable salt thereof in an amount that is equivalent to from 10 mg to 30 mg, advantageously from 15 mg to 25 mg, preferably of 15 mg, of solifenacin succinate. Solifenacin succinate Component (d) may be administered as a brand product (VESIcare® 5-mg and 10.mg) in multiple 5-mg or 10-mg doses.

According to a preferred, fifth aspect of this first embodiment, the invention provides the combination of the above second aspect of this first embodiment, wherein donepezil Component (c) and solifenacin/Component (d) are formulated in a fixed-dose combination, as illustrated above, essentially consisting of a pharmaceutical composition in dosage unit form comprising (c) donepezil or a pharmaceutically acceptable salt thereof, in an amount that is equivalent to from 10 mg to 92 mg of donepezil hydrochloride; and (d) solifenacin or a pharmaceutically acceptable salt thereof, in an amount that is equivalent to from 10 mg to 30 mg of solifenacin succinate, in admixture with a pharmaceutical carrier or vehicle, preferably in an IR-formulation.

Specifically this fifth aspect of this first embodiment, the present invention provides a pharmaceutical combination essentially consisting of (a/b) a pharmaceutical composition in dosage unit form comprising
  (a) memantine hydrochloride, in an amount of from 5 mg to 30 mg, preferably from 7 mg to 28 mg; and
  (b) a naAEA selected from the group consisting of alosetron and pharmaceutically acceptable salts and solvates thereof, in particular the hydrochloride, in an amount (in alosetron) of from 0.25 mg to 6 mg; azasetron and pharmaceutically acceptable salts and solvates thereof, in particular the hydrochloride, in an amount (in azasetron) of from 5 mg to 60 mg; dolasetron and pharmaceutically acceptable salts and solvates thereof, in particular the mesylate, in an amount (in dolasetron) of from 25 mg to 600 mg; granisetron and pharmaceutically acceptable salts and solvates thereof, in particular the hydrochloride, in an amount (in granisetron) of from 0.5 mg to 6 mg; ondansetron and pharmaceutically acceptable salts and solvates thereof, in particular the hydrochloride dihydrate, in an amount (in ondansetron) of from 2 mg to 64 mg; palonosetron and pharmaceutically acceptable salts and solvated thereof, in particular its hydrochloride, in an amount (in palonosetron) of from 0.25 mg to 3 mg; ramosetron and pharmaceutically acceptable salts and solvates thereof, in particular its hydrochloride, in an amount (in ramosetron) of from 0.0125 mg to 0.3 mg; tropisetron and pharmaceutically acceptable salts and solvates thereof, in particular the hydrochloride, in an amount of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine and pharmaceutically acceptable salts and solvates thereof, in particular the hydrochloride, in an amount (in chlorpromazine) of from 12.5 mg to 600 mg; prochlorperazine and pharmaceutically acceptable salts and solvates thereof, in particular the dimaleate, in an amount (in prochlorperazine) of from 2.5 mg to 30 mg; metoclopramide and pharmaceutically acceptable salts and solvates thereof, in particular the monohydrochloride monohydrate, in an amount (in metoclopramide) of from 5 mg to 60 mg; bromopride and pharmaceutically acceptable salts and solvates, in particular the monohydrochloride and the dihydrochloride monohydrate, in an amount (in bromopride) of from 5 mg to 60 mg; clebopride and pharmaceutically acceptable salts and solvates thereof, in particular the hydrogen malate and the hydrochloride monohydrate, in an amount (in clebopride) of from 0.25 mg to 3 mg; levosulpiride, in an amount of from 12.5 mg to 600 mg; alizapride and pharmaceutically acceptable salts thereof, in particular the hydrochloride, in an amount (in alizapride) of from 25 mg to 300 mg; trimethobenzamide and pharmaceutically acceptable salts thereof such as the monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine and pharmaceutically acceptable salts and solvates thereof, in particular the hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in admixture with a pharmaceutical carrier or vehicle; and (c/d) a pharmaceutical composition in dosage unit form comprising
  (c) donepezil hydrochloride, in an amount of from 10 mg to 92 mg, preferably from 20 mg to 92 mg, normally from 10 mg to 70 mg, preferably from 20 mg to 70 mg; and
  (d) solifenacin succinate, in an amount of from 10 mg to 30, advantageously from 15 mg to 25 mg, preferably of 15 mg,
in admixture with a pharmaceutical carrier or vehicle.

As set forth above, in the case of particular necessities, especially for use in the titration phase of the therapy, the donepezil hydrochloride effective amount that is present in the above fixed-dose combinations Component (c/d), may be from 10 mg to 50 mg, in particular of 10 mg, 15 mg, 20 mg, 25 mg, 30 mg, 35 mg, 40 mg.

According to a second embodiment, the present invention provides the combination of a NMDA-antagonist Component (a) selected from the group consisting of memantine and pharmaceutically acceptable salts thereof, any naAEA Component (b) as illustrated herein above in the "The naAEA Component (b)" section; a ChEI Component (c) selected from the group consisting of donepezil and pharmaceutically acceptable salts thereof, and a nsPAChA Component (d) selected from the group consisting of solifenacin and pharmaceutically acceptable salts thereof, each formulated in pharmaceutical composition in admixture with a pharmaceutical carrier.

In particular, the combination of the present invention may be a combination comprising or consisting essentially of
(a) memantine or a pharmaceutically acceptable salts and solvates thereof, in a pharmaceutical composition in admixture with a pharmaceutical carrier or vehicle;
(b) any naAEA described herein above, each in a pharmaceutical composition in admixture with a pharmaceutical carrier or vehicle, said naAEA being preferably selected from the group consisting of alosetron and pharmaceutically acceptable salts and solvates thereof; dolasetron and pharmaceutically acceptable salts and solvates thereof; granisetron and pharmaceutically acceptable salts and solvates thereof; ondansetron and pharmaceutically acceptable salts and solvates thereof; palonosetron and pharmaceutically acceptable salts and solvates thereof; domperidone and pharmaceutically acceptable salts and solvates thereof; tropisetron and pharmaceutically acceptable salts and solvates thereof; domperidone and pharmaceutically acceptable salts and solvates thereof; haloperidol; chlorpromazine and pharmaceutically acceptable salts and solvates thereof; prochlorperazine and pharmaceutically acceptable salts and solvates thereof; metoclopramide and pharmaceutically acceptable salts and solvates thereof; bromopride and pharmaceutically acceptable salts and solvates thereof; clebopride and pharmaceutically acceptable salts and solvates thereof; levosulpiride; alizapride and pharmaceutically acceptable salts thereof; trimethobenzamide and pharmaceutically acceptable salts thereof; meclizine (also called meclozine) and pharmaceutically acceptable salts and solvates thereof; promethazine and pharmaceutically acceptable salts and solvates thereof; dronabinol; nabilone; aprepitant; netupitant; rolapitant; casopitant;
(c) donepezil or a pharmaceutically acceptable salt thereof, in a pharmaceutical composition in admixture with a pharmaceutical carrier or vehicle; and
(d) solifenacin or a pharmaceutically acceptable salt thereof, in a pharmaceutical composition in admixture with a pharmaceutical carrier or vehicle.

In the above combination, each of the Components (a), (b), (c) and (d) are in pharmaceutical composition in dosage unit form wherein each of said components is in admixture with a pharmaceutical carrier in IR- or ER formulation.

In particular the present invention provides, according to a second embodiment, a pharmaceutical combination comprising or consisting essentially of, as Components:
(a) a NMDA-antagonist selected from the group consisting of memantine and pharmaceutically acceptable salts thereof, in a pharmaceutical composition in admixture with a pharmaceutical carrier or vehicle;
(b) a naAEA selected from the group consisting of (b1) 5HT3-antagonists, (b2) DA-antagonists, (b3) H1-antagonists, (b4) cannabinoids, (b5) NK1-antagonists, and the netupitant-palonosetron fixed-dose combination, in a pharmaceutical composition in admixture with a pharmaceutical carrier or vehicle;
(c) a ChEI selected from the group consisting of donepezil and pharmaceutically acceptable salts thereof, in a pharmaceutical composition in admixture with a pharmaceutical carrier or vehicle; and
(d) a nsPAChA selected from the group consisting of solifenacin and pharmaceutically acceptable salts thereof, in a pharmaceutical composition in admixture with a pharmaceutical carrier or vehicle.

A first advantageous aspect of this second embodiment provides a pharmaceutical combination comprising or consisting essentially of, as Components:
(a) a NMDA-antagonist selected from the group consisting of memantine and pharmaceutically acceptable salts thereof, in a pharmaceutical composition in admixture with a pharmaceutical carrier or vehicle;
(b) a naAEA consisting of a 5HT3-antagonist selected from the group consisting of alosetron and pharmaceutically acceptable salts and solvates thereof, in particular the hydrochloride, in an amount (in alosetron) of from 0.25 mg to 6 mg; azasetron and pharmaceutically acceptable salts and solvates thereof, in particular the hydrochloride, in an amount (in azasetron) of from 5 mg to 60 mg; dolasetron and pharmaceutically acceptable salts and solvates thereof, in particular the mesylate, in an amount (in dolasetron) of from 25 mg to 600 mg; granisetron and pharmaceutically acceptable salts and solvates thereof, in particular the hydrochloride, in an amount (in granisetron) of from 0.5 mg to 6 mg; ondansetron and pharmaceutically acceptable salts and solvates thereof, in particular the hydrochloride dihydrate, in an amount (in ondansetron) of from 2 mg to 64 mg; palonosetron and pharmaceutically acceptable salts thereof, in particular the hydrochloride, in an amount (in palonosetron) of from 0.25 mg to 3 mg; ramosetron and pharmaceutically acceptable salts thereof, in particular its hydrochloride, in an amount (in ramosetron) of from 0.0125 mg to 0.3 mg, tropisetron and pharmaceutically acceptable salts and solvates thereof, in particular the hydrochloride, in an amount of from 2.5 mg to 30 mg, in a pharmaceutical composition in admixture with a pharmaceutical carrier or vehicle;
(c) a ChEI selected from the group consisting of donepezil and pharmaceutically acceptable salts thereof, in a pharmaceutical composition in admixture with a pharmaceutical carrier or vehicle; and
(d) a nsPAChA selected from the group consisting of solifenacin and pharmaceutically acceptable salts thereof, in a pharmaceutical composition in admixture with a pharmaceutical carrier or vehicle.

A second advantageous aspect of this second embodiment provides a pharmaceutical combination comprising or consisting essentially of, as Components:
(a) a NMDA-antagonist selected from the group consisting of memantine and pharmaceutically acceptable salts thereof, in a pharmaceutical composition in admixture with a pharmaceutical carrier or vehicle;
(b) a naAEA consisting of a fixed-dose combination comprising palonosetron, in an amount of from 0.25 mg to 3 mg of palonosetron or a pharmaceutically acceptable salt thereof such as its hydrochloride and from 150 mg to 600 mg of netupitant, in admixture with a pharmaceutical carrier or vehicle in an oral IR formulation;
(c) a ChEI selected from the group consisting of donepezil and pharmaceutically acceptable salts thereof, in a pharmaceutical composition in admixture with a pharmaceutical carrier or vehicle; and
(d) a nsPAChA selected from the group consisting of solifenacin and pharmaceutically acceptable salts thereof, in a pharmaceutical composition in admixture with a pharmaceutical carrier or vehicle.

According to this second embodiment, a third advantageous aspect is a combination comprising or consisting essentially of, as Components:
(a) a NMDA-antagonist selected from the group consisting of memantine and pharmaceutically acceptable salts thereof, in a pharmaceutical composition in admixture with a pharmaceutical carrier or vehicle;
(b) a naAEA consisting of a DA-antagonist consisting of domperidone and pharmaceutically acceptable salts and solvates thereof such as the maleate; chlorpromazine and pharmaceutically acceptable salts and solvates thereof such as the hydrochloride; prochlorperazine and its salts and solvates, particularly the dimaleate and the dimesylate; promethazine and pharmaceutically acceptable salts and solvates thereof such as the hydrochloride; and 4-aminosalicylamide derivatives such as metoclopramide and pharmaceutically acceptable salts and solvates thereof such as the hydrochloride monohydrate, bromopride and pharmaceutically acceptable salts and solvates thereof such as the monohydrochloride or the dihydrochloride monohydrate, alizapride and pharmaceutically acceptable salts and solvates thereof such as the hydrochloride, and clebopride and pharmaceutically acceptable salts and solvates thereof such as the malate and the hydrochloride monohydrate; in a pharmaceutical composition in admixture with a pharmaceutical carrier or vehicle a nsPAChA selected from the group consisting of solifenacin and pharmaceutically acceptable salts thereof, in a pharmaceutical composition in admixture with a pharmaceutical carrier or vehicle;
(c) a ChEI selected from the group consisting of donepezil and pharmaceutically acceptable salts thereof, in a pharmaceutical composition in admixture with a pharmaceutical carrier or vehicle; and
(d) a nsPAChA selected from the group consisting of solifenacin and pharmaceutically acceptable salts thereof, in a pharmaceutical composition in admixture with a pharmaceutical carrier or vehicle.

Preferably, said naAEA Component (b) is a DA-antagonist consisting of domperidone or a pharmaceutically acceptable salt thereof, in particular its maleate, in an amount (in domperidone) of from 5 mg to 20 mg per dosage unit in an IR unit form or in an amount of from 7.5 mg to 60 mg, preferably from 10 mg to 60 mg, in an ER unit form; metoclopramide or a pharmaceutically acceptable salt or solvate thereof, in particular its monohydrochloride monohydrate, in an amount (in metoclopramide) of from 5 mg to 20 mg per dosage unit in an IR unit form or in an amount of from 7.5 mg to 30 mg, preferably from 10 mg to 30 mg, in an ER unit form; alizapride or a pharmaceutically acceptable salt thereof, in particular its hydrochloride, in an amount (in alizapride) of from 25 mg to 100 mg per dosage unit in an IR unit form or in an amount of from 37.5 mg to 300 mg, preferably from 100 mg to 300 mg, in an ER unit form; in a pharmaceutical composition in admixture with a pharmaceutical carrier or vehicle.

A fourth advantageous aspect of this second embodiment, is a combination comprising or consisting essentially of the following Components
(a) a NMDA-antagonist selected from the group consisting of memantine and pharmaceutically acceptable salts thereof, in a pharmaceutical composition in admixture with a pharmaceutical carrier or vehicle;
(b) a naAEA consisting of a histamine H1 receptor antagonists selected from the group consisting of meclizine (meclozine) and pharmaceutically acceptable salts and solvates thereof such as the hydrochloride monohydrate; promethazine and pharmaceutically acceptable salts and solvates thereof such as the hydrochloride; chlorpromazine and pharmaceutically acceptable salts and solvates thereof such as the hydrochloride, prochlorperazine and pharmaceutically acceptable salts and solvates thereof such as the dimaleate, the dimesylate or the 1,2-ethanedisulfonate (1:1) (edisilate); hydroxyzine and pharmaceutically acceptable salts and solvates thereof such as the dihydrochloride or the 1,1'-methylene bis(2-hydroxy-3-naphthalenecarboxylic acid (pamoate) salt; in a pharmaceutical composition in admixture with a pharmaceutical carrier or vehicle;
(c) a ChEI selected from the group consisting of donepezil and pharmaceutically acceptable salts thereof, in a pharmaceutical composition in admixture with a pharmaceutical carrier or vehicle; and (d) a nsPAChA selected from the group consisting of solifenacin and pharmaceutically acceptable salts thereof, in a pharmaceutical composition in admixture with a pharmaceutical carrier or vehicle.

Preferably, said naAEA Component (b) is a histamine H1 receptor antagonists selected from the group consisting of meclizine or a pharmaceutically acceptable salt thereof, in particular its hydrochloride, in an amount (in meclizine) of from 25 mg to 100 mg per dosage unit in an IR unit form or in an amount of from 37.5 mg to 150 mg, preferably from 50 mg to 150 mg, in an ER unit form; chlorpromazine or a pharmaceutically acceptable salt thereof, in particular its hydrochloride, in an amount (in chlorpromazine) of from 50 mg to 200 mg per dosage unit in an IR unit form or in an amount of from 75 mg to 300 mg, preferably from 100 mg to 300 mg, in an ER unit form; prochlorperazine or a pharmaceutically acceptable salt thereof, in particular its maleate, in an amount (in prochlorperazine) of from 2.5 mg to 10 mg per dosage unit in an IR unit form or in an amount of from 3.75 mg to 15 mg, preferably from 5 mg to 15 mg, in an ER unit form; in a pharmaceutical composition in admixture with a pharmaceutical carrier or vehicle.

A fifth advantageous combination according to this second embodiment, is a combination comprising or consisting essentially of the following Components
(a) a NMDA-antagonist selected from the group consisting of memantine and pharmaceutically acceptable salts thereof, in a pharmaceutical composition in admixture with a pharmaceutical carrier or vehicle;
(b) a naAEA consisting of a NK1-antagonist selected from the group consisting of aprepitant, casopitant, netupitant and rolapitant, in a pharmaceutical composition in admixture with a pharmaceutical carrier or vehicle;
(c) a ChEI selected from the group consisting of donepezil and pharmaceutically acceptable salts thereof, in a pharmaceutical composition in admixture with a pharmaceutical carrier or vehicle; and
(d) a nsPAChA selected from the group consisting of solifenacin and pharmaceutically acceptable salts thereof, in a pharmaceutical composition in admixture with a pharmaceutical carrier or vehicle.

A sixth, preferred combination according to this second embodiment is a combination comprising or consisting essentially of the following Components:
(a) a NMDA-antagonist selected from the group consisting of memantine and pharmaceutically acceptable salts thereof, in a pharmaceutical composition in admixture with a pharmaceutical carrier or vehicle;
(b) a naAEA selected from the group consisting of alosetron and pharmaceutically acceptable salts and solvates thereof, in particular the hydrochloride, in an amount (in alosetron) of from 0.25 mg to 6 mg; azasetron and pharmaceutically acceptable salts and solvates thereof, in particular the hydrochloride, in an amount (in azasetron) of from 5 mg to 60 mg; dolasetron and pharmaceutically acceptable salts and solvates thereof, in particular the mesylate, in an amount (in dolasetron) of from 25 mg to 600 mg; granisetron and pharmaceutically acceptable salts and solvates thereof, in particular the hydrochloride, in an amount (in granisetron) of from 0.5 mg to 6 mg; ondansetron and pharmaceutically acceptable salts and solvates thereof, in particular the hydrochloride dihydrate, in an amount (in ondansetron) of from 2 mg to 64 mg; palonosetron and pharmaceutically acceptable salts and solvated thereof, in particular its hydrochloride, in an amount (in palonosetron) of from 0.25 mg to 3 mg; ramosetron and pharmaceutically acceptable salts and solvates thereof, in particular its hydrochloride, in an amount (in ramosetron) of from 0.0125 mg to 0.3 mg; tropisetron and pharmaceutically acceptable salts and solvates thereof, in particular the hydrochloride, in an amount of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine and pharmaceutically acceptable salts and solvates thereof, in particular the hydrochloride, in an amount (in chlorpromazine) of from 12.5 mg to 600 mg; prochlorperazine and pharmaceutically acceptable salts and solvates thereof, in particular the dimaleate, in an amount (in prochlorperazine) of from 2.5 mg to 30 mg; metoclopramide and pharmaceutically acceptable salts and solvates thereof, in particular the monohydrochloride monohydrate, in an amount (in metoclopramide) of from 5 mg to 60 mg; bromopride and pharmaceutically acceptable salts and solvates, in particular the monohydrochloride and the dihydrochloride monohydrate, in an amount (in bromopride) of from 5 mg to 60 mg; clebopride and pharmaceutically acceptable salts and solvates thereof, in particular the hydrogen malate and the hydrochloride monohydrate, in an amount (in clebopride) of from 0.25 mg to 3 mg; levosulpiride, in an amount of from 12.5 mg to 600 mg; alizapride and pharmaceutically acceptable salts thereof, in particular the hydrochloride, in an amount (in alizapride) of from 25 mg to 300 mg; trimethobenzamide and pharmaceutically acceptable salts thereof such as the monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine and pharmaceutically acceptable salts and solvates thereof, in particular the hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant; in a pharmaceutical composition in admixture with a pharmaceutical carrier or vehicle;
(c) a ChEI selected from the group consisting of donepezil and pharmaceutically acceptable salts thereof, in a pharmaceutical composition in admixture with a pharmaceutical carrier or vehicle; and
(d) a nsPAChA selected from the group consisting of solifenacin and pharmaceutically acceptable salts thereof, in a pharmaceutical composition in admixture with a pharmaceutical carrier or vehicle.

A seventh, particularly advantageous combination according to this second embodiment essentially consists of
(a) a NMDA-antagonist selected from the group consisting of memantine or a pharmaceutically acceptable salt thereof, in an amount of from 5 mg to 30 mg, in admixture with a pharmaceutical carrier or vehicle;
(b) a naAEA selected from the group consisting of ondansetron hydrochloride dihydrate, in an amount (in ondansetron) of from 4 mg to 64 mg, domperidone, in an amount, in domperidone of 5 mg to 30 mg; and metoclopramide monohydrochloride monohydrate in an amount (in metoclopramide) of from 5 mg to 30 mg; in a pharmaceutical composition in admixture with a pharmaceutical carrier or vehicle;
(c) a ChEI selected from the group consisting of donepezil and pharmaceutically acceptable salts thereof, in an amount of from 10 mg to 92 mg, preferably from 20 mg to 92 mg, normally from 10 mg to 70 mg, preferably from 20 mg to 70 mg, in admixture with a pharmaceutical carrier or vehicle; and (d) a nsPAChA selected from the group consisting of solifenacin and pharmaceutically acceptable salts thereof, in an amount of from 10 mg to 30 mg, advantageously from 15 mg to 25 mg, preferably of 15 mg, in admixture with a pharmaceutical carrier or vehicle.

An eight advantageous combination according to this second embodiment essentially consists of (a) a NMDA-antagonist selected from the group consisting of memantine or a pharmaceutically acceptable salt thereof, in an amount of from 5 mg to 30 mg, in admixture with a pharmaceutical carrier or vehicle;

(b) a naAEA selected from the group consisting of a netupitant/palonosetron fixed-dose combination comprising netupitant, in an amount of 300 mg and palonosetron hydrochloride, in an amount (in palonosetron) of 0.5, in admixture with a pharmaceutical carrier or vehicle;

(c) a ChEI selected from the group consisting of donepezil and pharmaceutically acceptable salts thereof, in an amount of from 20 mg to 92 mg, in admixture with a pharmaceutical carrier or vehicle; and (d) a nsPAChA selected from the group consisting of solifenacin and pharmaceutically acceptable salts thereof, in an amount of from 10 mg to 30 mg, advantageously from 15 mg to 25 mg, preferably of 15 mg, in admixture with a pharmaceutical carrier or vehicle.

In the combination according to this eight aspect of this second embodiment, Component (b) may be used as the palonosetron/netupitant brand preparation Akynzeo®, Preferably, according to these six aspects of this first embodiment, memantine Component (a), as hydrochloride, is present in an amount of from 5 mg to 10 mg in an IR formulation, or in an amount of from 7 mg to 28 mg in an ER-formulation. In particular, it may be used as its brand preparation Namenda®.

According to a further second embodiment, the invention provides the herein above illustrated memantine/solifenacin combination comprising (a) memantine or a pharmaceutically acceptable salt thereof; and (b) solifenacin or a pharmaceutically acceptable salt thereof, for use for treating hypocholinergic disorders in further combination with donepezil or a pharmaceutically acceptable salt thereof in an amount that is equivalent to from 20 mg to 92 mg of donepezil hydrochloride, as a single dose.

Thanks to the solifenacin/memantine synergism, said donepezil amount may be of from 10 mg to 92 mg, advantageously from 20 mg to 92 mg, normally from 10 mg to 70 mg, preferably from 20 mg to 70 mg or from 40 mg to 70 mg, as a single dose, with substantially improved therapeutic response.

For the intended use, each of the Components (a) and (b) are formulated in a pharmaceutical composition. Thus, in the above combination, memantine or a pharmaceutically acceptable salt is in a pharmaceutical composition, preferably in dosage unit form, comprising said memantine or pharmaceutically acceptable salt thereof, in an amount that is equivalent to from 5 mg to 30 mg, preferably from 7 mg to 28 mg, of memantine hydrochloride, in admixture with a pharmaceutical carrier or vehicle; and said solifenacin or pharmaceutically acceptable salt thereof is in a pharmaceutical composition, preferably in dosage unit form, comprising said solifenacin or pharmaceutically acceptable salt thereof, in an amount that is equivalent to from 10 mg to 30 mg, advantageously from 15 mg to 25 mg, preferably of 15 mg, of solifenacin succinate.

In a further second embodiment, the invention provides a combination comprising (a) a pharmaceutical composition comprising memantine or a pharmaceutically acceptable salt thereof, in an amount that is equivalent to from 5 mg to 30 mg, preferably from 7 mg to 28 mg, of memantine hydrochloride, in admixture with a pharmaceutical carrier or vehicle; and (b) a pharmaceutical composition comprising solifenacin or a pharmaceutically acceptable salt thereof, in an amount that is equivalent to from 10 mg to 30 mg, advantageously from 15 mg to 25 mg, preferably 15 mg, of solifenacin succinate, in admixture with a pharmaceutical carrier or vehicle, for use for treating Alzheimer type dementia in further combination with a pharmaceutical composition comprising donepezil or a pharmaceutically acceptable salt thereof.

Said donepezil or pharmaceutically acceptable salt thereof is administered at a daily dose that is equivalent to from 10 mg to 92 mg, preferably from 20 mg to 92 mg, normally from 10 mg to 70 mg, preferably from 20 mg to 70 mg of donepezil hydrochloride.

Preferably, this memantine/solifenacin combination is a memantine hydrochloride/solifenacin succinate combination for use in combination with a pharmaceutical composition comprising donepezil hydrochloride, in an amount of from 10 mg to 92 mg, preferably from 20 mg to 92 mg, normally from 10 mg to 70 mg, preferably from 20 mg to 70 mg, in admixture with a pharmaceutical carrier or vehicle, administered once per day.

Thanks to the solifenacin/memantine synergism, said donepezil hydrochloride amount may be of from 10 mg to 92 mg, advantageously from 20 mg to 70 mg, or from 40 mg to 70 mg, as a single daily dose, with substantially improved therapeutic response.

According to a this preferred embodiment, memantine or a pharmaceutically acceptable salt thereof and solifenacin or a pharmaceutically acceptable salt thereof are in a fixed-dose combination as illustrated herein above, Said fixed-dose combination essentially consists of a pharmaceutical composition, preferably in dosage unit form, comprising said memantine or pharmaceutically acceptable salt thereof, in an amount that is equivalent to from 5 mg to 30 mg; and said solifenacin or pharmaceutically acceptable salt thereof, in an amount that is equivalent to from 10 to 30 mg, advantageously from 15 mg to 25 mg, preferably of 15 mg, in admixture with a pharmaceutical carrier or vehicle.

The memantine/solifenacin fixed-dose combination according to this preferred embodiment is useful for an easy and safe treatment of hypocholinergic disorders in combination with a pharmaceutical composition comprising donepezil or a pharmaceutically acceptable salt thereof, in an amount that is equivalent to from 10 mg to 92 mg, preferably from 20 mg to 92 mg, normally from 10 mg to 70 mg, preferably from 20 mg to 70 mg mg or from 40 mg to 70 mg of donepezil hydrochloride.

Thus, the present invention also provides a method for the treatment of a hypocholinergic disorder such as Alzheimer type dementia, for example from Alzheimer's dementia, Parkinson's disease, Lewy body disease dementia and related disorders, which comprises treating a patient in need of said treatment with an effective amount of a N-methyl-D-aspartate receptor antagonist selected from the group consisting of memantine and pharmaceutical acceptable salts thereof [(Component (a)], and with an effective amount of a non-selective peripheral anticholinergic agent selected from the group consisting of solifenacin and pharmaceutically acceptable salts thereof [Component (b)], in combination with a cholinesterase inhibitor selected from the group consisting of donepezil and pharmaceutically acceptable salts thereof [Component (c)], at a daily dose that is equivalent to from 20 mg to 92 mg of donepezil hydrochloride.

According to a particular advantageous aspect of the above method, said component (a) and said Component (b) are in a fixed-dose combination essentially consisting of a pharmaceutical composition comprising (a) memantine or a pharmaceutically acceptable salt thereof, in an amount that is equivalent to from 5 mg to 30 mg, preferably from 7 mg to 28 g, of memantine hydrochloride; and (b) solifenacin or a pharmaceutical acceptable salt thereof, in an amount that is equivalent to from 10 mg to 30 mg, advantageously from 15 mg to 25 mg, preferably 15 mg, of solifenacin succinate, in admixture with a pharmaceutical carrier or vehicle.

This pharmaceutical combinations according to this second embodiment of the present invention is useful for the treatment of a hypocholinergic disorder as herein above defined, and even high doses of a donepezil Component (c), as illustrated above, may be present to improve symptoms without adverse effects to a greater extent.

Thus, the present invention provides a method for treating Alzheimer type dementia, which comprises administering to a patient in need of said treatment the combinations described herein above. In such a treatment, Component (a), Component (b), Component (c) and Component (d) of the combination may be administered simultaneously or sequentially to said patient, Component (a) being indifferently administered before or after Component (b), Component (c) and Component (d). Components (a), Component (b), Component (c), and Component (d) may also be administered by the same or a different administration route.

According to a third embodiment, an advantageous NMDA-antagonist/naAEA/ChEI/nsPAChA combination may be a combination comprising or consisting essentially of (a) a NMDA-antagonist selected from the group consisting of memantine and pharmaceutically acceptable salts thereof, in a pharmaceutical composition in admixture with a pharmaceutical carrier or vehicle;

(b/d) a fixed-dose combination comprising
  (b) a naAEA; and
  (d) a nsPAChA selected from the group consisting of solifenacin and pharmaceutically acceptable salts thereof,
in admixture with a pharmaceutical carrier or vehicle; and (c) a ChEI selected from the group consisting of donepezil and pharmaceutically acceptable salts thereof, in a pharmaceutical composition in admixture with a pharmaceutical carrier or vehicle.

In the fixed dose combination (b/d), the naAEA may be any one of those disclosed in the above "The naAEA Component (b)" section. Advantageous Component (b/d) may be a naAEA/solifenacin fixed-dose combination consisting of any one of the pharmaceutical compositions described in WO 2014/039627 (see also US 2015/0231122), the disclosures of which are incorporated herein in their entirety for reference.

According to an aspect of this third embodiment, the invention provides a combination comprising or consisting essentially of (a) a NMDA-antagonist selected from the group consisting of memantine and pharmaceutically acceptable salts thereof in an amount that is equivalent to from 5 mg to 30 mg of memantine hydrochloride, in a pharmaceutical composition in admixture with a pharmaceutical carrier or vehicle;

(b/d) a fixed-dose combination essentially consisting of a pharmaceutical composition in dosage unit form comprising (b) a naAEA selected from the group consisting of alosetron and pharmaceutically acceptable salts and solvates thereof, in particular the hydrochloride, in an amount (in alosetron) of from 0.25 mg to 6 mg; azasetron and pharmaceutically acceptable salts and solvates thereof, in particular the hydrochloride, in an amount (in azasetron) of from 5 mg to 60 mg; dolasetron and pharmaceutically acceptable salts and solvates thereof, in particular the mesylate, in an amount (in dolasetron) of from 25 mg to 600 mg; granisetron and pharmaceutically acceptable salts and solvates thereof, in particular the hydrochloride, in an amount (in granisetron) of from 0.5 mg to 6 mg; ondansetron and pharmaceutically acceptable salts and solvates thereof, in particular the hydrochloride dihydrate, in an amount (in ondansetron) of from 2 mg to 64 mg; palonosetron and pharmaceutically acceptable salts and solvated thereof, in particular its hydrochloride, in an amount (in palonosetron) of from 0.25 mg to 3 mg; ramosetron and pharmaceutically acceptable salts and solvates thereof, in particular its hydrochloride, in an amount (in ramosetron) of from 0.0125 mg to 0.3 mg; tropisetron and pharmaceutically acceptable salts and solvates thereof, in particular the hydrochloride, in an amount of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine and pharmaceutically acceptable salts and solvates thereof, in particular the hydrochloride, in an amount (in chlorpromazine) of from 12.5 mg to 600 mg; prochlorperazine and pharmaceutically acceptable salts and solvates thereof, in particular the dimaleate, in an amount (in prochlorperazine) of from 2.5 mg to 30 mg; metoclopramide and pharmaceutically acceptable salts and solvates thereof, in particular the monohydrochloride monohydrate, in an amount (in metoclopramide) of from 5 mg to 60 mg; bromopride and pharmaceutically acceptable salts and solvates, in particular the monohydrochloride and the dihydrochloride monohydrate, in an amount (in bromopride) of from 5 mg to 60 mg; clebopride and pharmaceutically acceptable salts and solvates thereof, in particular the hydrogen malate and the hydrochloride monohydrate, in an amount (in clebopride) of from 0.25 mg to 3 mg; levosulpiride, in an amount of from 12.5 mg to 600 mg; alizapride and pharmaceutically acceptable salts thereof, in particular the hydrochloride, in an amount (in alizapride) of from 25 mg to 300 mg; trimethobenzamide and pharmaceutically acceptable salts thereof such as the monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine and pharmaceutically acceptable salts and solvates thereof, in particular the hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant; and (d) a nsPAChA selected from the group consisting of solifenacin and pharmaceutically acceptable salts thereof, in an amount that is equivalent to from 10 mg to 30 mg, advantageously from 15 mg to 25 mg, preferably of 15 mg of solifenacin succinate, in admixture with a pharmaceutical carrier or vehicle; and (e) a ChEI selected from the group consisting of donepezil and pharmaceutically acceptable salts thereof, in an amount that is equivalent to from 20 mg to 92 mg, in a pharmaceutical composition in admixture with a pharmaceutical carrier or vehicle.

Preferably, the naAEA selected from the group consisting of alosetron hydrochloride, in an amount (in alosetron) of from 0.25 mg to 6 mg; azasetron hydrochloride, in an amount (in azasetron) of from 5 mg to 60 mg; dolasetron mesylate, in an amount (in dolasetron) of from 25 mg to 600 mg; granisetron hydrochloride, in an amount (in granisetron) of from 0.5 mg to 6 mg; ondansetron hydrochloride dihydrate, in an amount (in ondansetron) of from 2 mg to 64 mg; palonosetron hydrochloride, in an amount (in palonosetron) of from 0.25 mg to 3 mg; ramosetron hydrochloride, in an amount (in ramosetron) of from 0.0125 mg to 0.3 mg, tropisetron hydrochloride, in an amount (in tropisetron) of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine hydrochloride, in an amount (in chlorpromazine) of from 12.5 mg to 600 mg; prochlorperazine dimaleate, in an amount (in prochlorperazine) of from 2.5 mg to 30 mg; metoclopramide monohydrochloride monohydrate, in an amount (in metoclopramide) of from 5 mg to 60 mg; bromopride monohydrochloride or dihydrochloride monohydrate, in an amount (in bromopride) of from 5 mg to 60 mg; clebopride hydrogen malate or hydrochloride monohydrate, in an amount (in clebopride) of from 0.25 mg to 3 mg; levosulpiride, in an amount of from 12.5 mg to 600 mg; alizapride hydrochloride, in an amount (in alizapride) of from 25 mg to 300 mg; trimethobenzamide monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg.

In a further third embodiment, the present invention provides a memantine/solifenacin/donepezil combination comprising (a) a pharmaceutical composition in dosage unit form comprising or consisting essentially of memantine or a pharmaceutically acceptable salt thereof, preferably its hydrochloride, in admixture with a pharmaceutical carrier or vehicle in an IR or ER form; and (b/c) a fixed-dose combination that is a pharmaceutical composition comprising or consisting essentially of (b) solifenacin or a pharmaceutically acceptable salt, preferably its succinate; and (c) donepezil or a pharmaceutically acceptable salt, preferably its hydrochloride, in admixture with a pharmaceutical carrier or vehicle, in IR-form.

This combination has the advantage of allowing an improvement in the treatment of a patient suffering from Alzheimer type dementia. In fact, in the case of the prescription of IR-memantine that must be taken two times/day, the Component (b/c) of this third embodiment of the invention allows the administration of a composition (b/c) comprising solifenacin and donepezil that are administered once a day, thus rendering the treatment easier for the patient or for the caregiver.

For example, a combination according to this third embodiment may comprise:

(a) a pharmaceutical composition in dosage unit form comprising or consisting essentially of a memantine pharmaceutically acceptable salt, preferably the hydrochloride in an amount of from 7 mg to 28 mg in admixture with a pharmaceutical carrier or vehicle in an IR or ER form, in admixture with a pharmaceutical carrier or vehicle; and (b/c) a fixed-dose combination that is a pharmaceutical composition comprising or consisting essentially of (b) a solifenacin pharmaceutically acceptable salt, preferably the succinate thereof in an amount of from 10 mg to 30 mg, advantageously from 15 mg to 25 mg; and (c) a donepezil pharmaceutically acceptable salt, preferably the hydrochloride thereof in an amount of from 10 mg to 92 mg, preferably from 20 mg to 92 mg, normally from 10 mg to 70 mg, preferably from 20 mg to 70 mg;

in admixture with a pharmaceutical carrier or vehicle in an IR form.

An advantageous combination of this third embodiment comprises:

(a) a pharmaceutical composition in dosage unit form comprising or consisting essentially of memantine hydrochloride, in an amount of from 7 mg to 28 mg in admixture with a pharmaceutical carrier or vehicle in ER form in admixture with a pharmaceutical carrier; and (b/c) a fixed-dose combination that is a pharmaceutical composition comprising or consisting essentially of (b) solifenacin succinate, in an amount of 15 mg; and (c) donepezil hydrochloride, in an amount of from 10 mg to 50 mg, normally from 10 mg to 40 mg, in admixture with a pharmaceutical carrier or vehicle, in IR-form.

As set forth above, this composition is particularly useful in the titration phase of the treatment of a patient suffering from a hypocholinergic disorder and also during the treatment of said disorders, for donepezil doses up to 50 mg single or daily dose.

According to an advantageous aspect of this third embodiment, the invention provides the above pharmaceutical composition in dosage unit form in a novel formulation wherein the pharmaceutical carrier allows that said solifenacin succinate and donepezil hydrochloride do not interact each other.

In particular, donepezil hydrochloride and solifenacin succinate are present in specific percent amount and the pharmaceutical carrier comprises a diluent such as talc, powdered cellulose, lactose; a disaggregating agents such as microcrystalline cellulose, crospovidone or a starch, for example maize or corn starch; a lubricant such as magnesium or calcium stearate; and a binder, such as methyl cellulose, ethyl cellulose or hydroxypropyl methyl cellulose, each in specific percent amounts.

Specifically, the pharmaceutical carrier comprises lactose as a diluent; corn starch as a disaggregating agent; magnesium stearate as a lubricant; and hydroxypropyl methyl cellulose as a binder.

Preferably, the pharmaceutical unit form comprising the preferred composition according to this third embodiment of the present invention is a coated tablet containing donepezil hydrochloride, in an amount of from 10 mg to 50 mg and solifenacin succinate, in an amount of 15 mg, as active ingredients, in the core, in admixture with a pharmaceutical carrier as defined above.

In particular, in the solifenacin/donepezil fixed dose combination essentially consists in a pharmaceutical composition in a dosage unit form consisting of a coated tablet comprising solifenacin succinate, in an amount of from 5.5% to 6.5%, donepezil hydrochloride, in an amount of from 4% to 20%; a diluent, in a amount of from 60% to 82%, a disaggregating agent, in a amount of from 6.8% to 7.5%; and a binder, in an amount of from 1.9% to 2.5% the total weight of the core. The coating is a non-enteric, fast-dissolving layer that covers the core according to known technologies. Normally, it is constituted by a cellulose derivative such as methyl hydroxyethyl cellulose or hydroxypropyl methyl cellulose, a glycerol ester such as diacetin or triacetin and a pigment such as titanium dioxide. Normally, the coating is Opadry®, especially the White 03K18533 type.

A fourth embodiment of the present invention provides a combination essentially consists of (a/c) a fixed-dose combination consisting of a pharmaceutical composition in dosage unit form comprising
  (a) memantine or a pharmaceutically acceptable salt thereof, in amount that is equivalent to from 5 mg to 30 mg of memantine hydrochloride; and
  (c) donepezil or a pharmaceutically acceptable salts thereof, in an amount that is equivalent to from 10 mg to 92 mg, preferably from 20 mg to 92 mg, normally from 10 mg to 70 mg, preferably from 20 mg to 70 mg of donepezil hydrochloride, in a pharmaceutical composition in admixture with a pharmaceutical carrier or vehicle;

(b) a pharmaceutical composition comprising a naAEA selected from the group consisting of) is selected from the group consisting of alosetron and pharmaceutically acceptable salts and solvates thereof, in particular the hydrochloride, in an amount (in alosetron) of from 0.25 mg to 6 mg; azasetron and pharmaceutically acceptable salts and solvates thereof, in particular the hydrochloride, in an amount (in azasetron) of from 5 mg to 60 mg; dolasetron and pharmaceutically acceptable salts and solvates thereof, in particular the mesylate, in an amount (in dolasetron) of from 25 mg to 600 mg; granisetron and pharmaceutically acceptable salts and solvates thereof, in particular the hydrochloride, in an amount (in granisetron) of from 0.5 mg to 6 mg; ondansetron and pharmaceutically acceptable salts and solvates thereof, in particular the hydrochloride dihydrate, in an amount (in ondansetron) of from 2 mg to 64 mg; palonosetron and pharmaceutically acceptable salts and solvated thereof, in particular its hydrochloride, in an amount (in palonosetron) of from 0.25 mg to 3 mg; ramosetron and pharmaceutically acceptable salts and solvates thereof, in particular its hydrochloride, in an amount (in ramosetron) of from 0.0125 mg to 0.3 mg; tropisetron and pharmaceutically acceptable salts and solvates thereof, in particular the hydrochloride, in an amount of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine and pharmaceutically acceptable salts and solvates thereof, in particular the hydrochloride, in an amount (in chlorpromazine) of from 12.5 mg to 600 mg; prochlorperazine and pharmaceutically acceptable salts and solvates thereof, in particular the dimaleate, in an amount (in prochlorperazine) of from 2.5 mg to 30 mg; metoclopramide and pharmaceutically acceptable salts and solvates thereof, in particular the monohydrochloride monohydrate, in an amount (in metoclopramide) of from 5 mg to 60 mg; bromopride and pharmaceutically acceptable salts and solvates, in particular the monohydrochloride and the dihydrochloride monohydrate, in an amount (in bromopride) of from 5 mg to 60 mg; clebopride and pharmaceutically acceptable salts and solvates thereof, in particular the hydrogen malate and the hydrochloride monohydrate, in an amount (in clebopride) of from 0.25 mg to 3 mg; levosulpiride, in an amount of from 12.5 mg to 600 mg; alizapride and pharmaceutically acceptable salts thereof, in particular the hydrochloride, in an amount (in alizapride) of from 25 mg to 300 mg; trimethobenzamide and pharmaceutically acceptable salts thereof such as the monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine and pharmaceutically acceptable salts and solvates thereof, in particular the hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant; and (d) a pharmaceutical composition comprising a nsPAChA selected from the group consisting of solifenacin and pharmaceutically acceptable salts thereof, in an amount that is equivalent to from 10 mg to 30 mg of solifenacin succinate, in admixture with a pharmaceutical carrier or vehicle, in admixture with a pharmaceutical carrier or vehicle.

Preferably, the naAEA is selected from the group consisting of alosetron hydrochloride, in an amount (in alosetron) of from 0.25 mg to 6 mg; azasetron hydrochloride, in an amount (in azasetron) of from 5 mg to 60 mg; dolasetron mesylate, in an amount (in dolasetron) of from 25 mg to 600 mg; granisetron hydrochloride, in an amount (in granisetron) of from 0.5 mg to 6 mg; ondansetron hydrochloride dihydrate, in an amount (in ondansetron) of from 2 mg to 64 mg; palonosetron hydrochloride, in an amount (in palonosetron) of from 0.25 mg to 3 mg; ramosetron hydrochloride, in an amount (in ramosetron) of from 0.0125 mg to 0.3 mg, tropisetron hydrochloride, in an amount (in tropisetron) of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine hydrochloride, in an amount (in chlorpromazine) of from 12.5 mg to 600 mg; prochlorperazine dimaleate, in an amount (in prochlorperazine) of from 2.5 mg to 30 mg; metoclopramide monohydrochloride monohydrate, in an amount (in metoclopramide) of from 5 mg to 60 mg; bromopride monohydrochloride or dihydrochloride monohydrate, in an amount (in bromopride) of from 5 mg to 60 mg; clebopride hydrogen malate or hydrochloride monohydrate, in an amount (in clebopride) of from 0.25 mg to 3 mg; levosulpiride, in an amount of from 12.5 mg to 600 mg; alizapride hydrochloride, in an amount (in alizapride) of from 25 mg to 300 mg; trimethobenzamide monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant in an amount of from 25 mg to 300 mg.

The Component (a/c) may be the brand memantine/donepezil fixed-dose combination, as its brand preparation Namzaric®, in its 7 mg-memantine/10 mg-donepezil presentation that may be used in multiple unit forms per each administration, when a 30 mg or 40 mg of donepezil hydrochloride dose is required.

Component (b) may be the brand palonosetron/netupitant (Akynzeo®) consisting of a capsule containing netupitant in an amount of 300 mg and palonosetron hydrochloride in an amount (in palonosetron) of 0.5 mg.

In a further fourth embodiment, the invention provides a pharmaceutical combination comprising
(a/c) a fixed-dose combination that is a pharmaceutical composition comprising or consisting essentially of
  (a) memantine or a pharmaceutically acceptable salt thereof; and
  (c) donepezil or a pharmaceutically acceptable salt thereof,
in admixture with a pharmaceutical carrier or vehicle; and
(b) a pharmaceutical composition in dosage unit form comprising or consisting essentially of solifenacin or a pharmaceutically acceptable salt thereof in admixture with a pharmaceutical carrier.

According to an advantageous aspect of this fourth embodiment, the invention provides a combination comprising:
(a/c) a fixed-dose combination that is a pharmaceutical composition comprising or consisting essentially of
  (a) a memantine or a pharmaceutically acceptable salt thereof, preferably the hydrochloride thereof in an amount of from 5 mg to 30 mg; and
  (c) donepezil or a pharmaceutically acceptable salt thereof, preferably the hydrochloride thereof in an amount of from 10 mg to 92 mg,
in admixture with a pharmaceutical carrier or vehicle; and
(b) a pharmaceutical composition in dosage unit form comprising or consisting essentially of solifenacin or a pharmaceutically acceptable salt thereof, preferably the succinate thereof in an amount of from 10 mg to 30 mg,
in admixture with a pharmaceutical carrier or vehicle.

In a preferred combination according to this fourth embodiment, the Component (a/c) comprises memantine hydrochloride, in an amount of from 7 mg to 28 mg; and donepezil hydrochloride, in an amount of from 10 mg to 70 mg, normally from 20 mg to 70 mg; and the Component (b) is solifenacin succinate, in an amount of from 15 mg to 25 mg.

This memantine/donepezil fixed dose combination is also available as a brand preparation (Namzaric®), consisting of memantine hydrochloride extended-release/donepezil hydrochloride fixed-dose combination, when a 10-mg donepezil dose is required.

Said donepezil or pharmaceutically acceptable salt thereof is administered at a daily dose that is equivalent to from 20 mg to 92 mg donepezil hydrochloride.

Preferably, this memantine/solifenacin combination is a memantine hydrochloride/solifenacin succinate combination for use in combination with a pharmaceutical composition comprising donepezil hydrochloride, in an amount of from 20 mg to 92 mg, in admixture with a pharmaceutical carrier or vehicle, administered once per day.

An advantageous composition according to this embodiment consists of
Layer A, comprising from 7 mg to 28 mg of memantine hydrochloride Component (a) in admixture with a pharmaceutical carrier or vehicle in a ER formulation; and
Layer B, comprising from 10 mg to 30 mg of solifenacin succinate Component (b), in admixture with a pharmaceutical carrier or vehicle in an IR-formulation, said composition being destined to be administered once per day, in combination with a pharmaceutical composition comprising from 20 mg to 92 mg, advantageously from 40 mg to 92 mg, normally from 40 mg to 70 mg, of donepezil hydrochloride, also destined to be administered once per day.

Carriers or vehicles and vehicles for ER tablets include retardant materials such as is acrylic and methacrylic acid polymers and copolymers; cellulose derivatives such as hydroxypropylmethylcellulose, hydroxyethylcellulose, hydroxypropylethylcellulose, hydroxypropylcelluloses, methylcellulose, ethylcellulose, or sodium carboxymethylcellulose; gums; waxes; glycerides or aliphatic alcohols or a mixture thereof.

According to another embodiment, the invention provides the herein above illustrated memantine/solifenacin combination comprising
(c) memantine or a pharmaceutically acceptable salt thereof; and
(d) solifenacin or a pharmaceutically acceptable salt thereof, for use for treating hypocholinergic disorders in further combination with donepezil or a pharmaceutically acceptable salt thereof in an amount that is equivalent to from 20 mg to 92 mg of donepezil hydrochloride, as a single dose.

Thanks to the solifenacin/memantine synergism, said donepezil hydrochloride amount may advantageously be of from 40 mg to 92 mg or from 40 mg to 70 mg, as a single daily dose, with substantially improved therapeutic response.

For the intended use, each of the Components (a) and (b) are formulated in a pharmaceutical composition. Thus, in the above combination, memantine or a pharmaceutically acceptable salt is in a pharmaceutical composition, preferably in dosage unit form, comprising said memantine or pharmaceutically acceptable salt thereof, in an amount that is equivalent to from 5 mg to 30 mg of memantine hydrochloride, in admixture with a pharmaceutical carrier or vehicle; and said solifenacin or pharmaceutically acceptable salt thereof is in a pharmaceutical composition, preferably in dosage unit form, comprising said solifenacin or pharmaceutically acceptable salt thereof, in an amount that is equivalent to from 10 mg to 30 mg of solifenacin succinate.

Component (a) and Component (b) are advantageously combined in a fixed dose combination for the simultaneous administration of the two Components. These fixed-dose combinations are in pharmaceutical unit forms wherein Component (a) and Component (b) are present, together or separately, in admixture with a pharmaceutical carrier or vehicle. In these unit forms, memantine or a pharmaceutically acceptable salt thereof, especially its hydrochloride, and solifenacin or a pharmaceutically acceptable salt thereof, especially its succinate, are present in an IR- or ER-formulation.

According to a preferred embodiment, the invention provides a combination comprising
(a) a pharmaceutical composition comprising memantine or a pharmaceutically acceptable salt thereof, in an amount that is equivalent to from 5 mg to 30 mg of memantine hydrochloride, in admixture with a pharmaceutical carrier or vehicle; and
(b) a pharmaceutical composition comprising solifenacin or a pharmaceutically acceptable salt thereof, in an amount that is equivalent to from 10 mg to 30 mg of solifenacin succinate, in admixture with a pharmaceutical carrier or vehicle, for use for treating Alzheimer type dementia in further combination with a pharmaceutical composition comprising donepezil or a pharmaceutically acceptable salt thereof.

Said donepezil or pharmaceutically acceptable salt thereof is administered at a daily dose that is equivalent to from 20 mg to 92 mg donepezil hydrochloride.

Preferably, this memantine/solifenacin combination is a memantine hydrochloride/solifenacin succinate combination for use in combination with a pharmaceutical composition comprising donepezil hydrochloride, in an amount of from 20 mg to 92 mg, in admixture with a pharmaceutical carrier or vehicle, administered once per day.

Thanks to the solifenacin/memantine synergism, said donepezil hydrochloride amount may advantageously be of from 40 mg to 92 mg or from 40 mg to 70 mg, as a single daily dose, with substantially improved therapeutic response.

According to a this preferred embodiment, memantine or a pharmaceutically acceptable salt thereof and solifenacin or a pharmaceutically acceptable salt thereof are in a fixed-dose combination as illustrated herein above, Said fixed-dose combination essentially consists of a pharmaceutical composition, preferably in dosage unit form, comprising said memantine or pharmaceutically acceptable salt thereof, in an amount that is equivalent to from 5 mg to 30 mg; and said solifenacin or pharmaceutically acceptable salt thereof, in an amount that is equivalent to from 10 to 30 mg, in admixture with a pharmaceutical carrier or vehicle.

The memantine/solifenacin fixed-dose combination according to this preferred embodiment is useful for an easy and safe treatment of hypocholinergic disorders in combination with a pharmaceutical composition comprising donepezil or a pharmaceutically acceptable salt thereof, in an amount that is equivalent to from 20 mg to 92 mg, preferably from 40 mg to 92 mg, normally from 40 mg to 70 mg of donepezil hydrochloride.

According to another embodiment, the present invention provides a fixed-dose combination essentially consisting of a pharmaceutical composition comprising, as Components,
(a) memantine or a pharmaceutically acceptable salt thereof, in an amount that is equivalent to from 5 mg to 30 mg of memantine hydrochloride;
(b) solifenacin or a pharmaceutical acceptable salt thereof, in an amount that is equivalent to from 10 mg to 30 mg of solifenacin succinate; and
(c) donepezil or a pharmaceutically acceptable salt thereof, in an amount that is equivalent to from 20 mg to 92 mg of donepezil hydrochloride,
in admixture with a pharmaceutical carrier or vehicle.

According to an advantageous aspect of this embodiment, the pharmaceutical composition comprises memantine hydrochloride, in an amount of from 5 mg to 30 mg, solifenacin succinate, in an amount of from 10 mg to 30 mg and donepezil hydrochloride, in an amount of from 40 kg to 92 mg, normally from 40 mg to 70 mg.

A pharmaceutical unit form comprising (a) memantine hydrochloride, in a pharmaceutical composition comprising said memantine hydrochloride in an amount of from 5 mg to 30 mg, in admixture with a pharmaceutical carrier in extended-release formulation; and (b) solifenacin succinate, in a pharmaceutical composition comprising said solifenacin succinate in an amount of from 10 mg to 30 mg, in admixture with a pharmaceutical carrier or vehicle in an immediate release formulation, is particularly advantageous.

For oral use, Component (a) and Component (b) are in compositions in admixture with pharmaceutical excipients in known formulations wherein said Components are mixed together or separated, for example in two tablets introduced in a capsule, as described in as described in GB 1204580, the disclosure of which is incorporated herein for reference, or in a two-compartment capsule or in a multilayer (bilayer) tablet wherein the two components are both in IR form or wherein the memantine pharmaceutically acceptable salt, especially the hydrochloride, is in ER-form, and the solifenacin pharmaceutically acceptable salt, especially the succinate thereof, is in IR-form, according to the technologies disclosed in U.S. Pat. No. 7,303,761 or 8,802,143, the disclosures of which are incorporated herein in their entirety for reference.

Component (a) and Component (b) may also be present in form of one of their complexes with a cyclodextrin, for example α-cyclodextrin, β-cyclodextrin, γ-cyclodextrin, 2-hydroxypropyl-β-cyclodextrin or methyl-β-cyclodextrin.

Component (a) and Component (b) may also be formulated in the form of microcapsules, optionally with one or more carriers or vehicles or additives.

For oral administration, Component (a) and Component (b), together or separately, are formulated by mixing the active ingredient with conventional pharmaceutical acceptable carriers or vehicles enabling said active ingredients to be formulated in tablets, dragees, orally disintegrating tablets, capsules, liquid solutions or suspensions, syrups and the like.

The composition according to the present invention may be in form of a capsule containing two tablets as described herein above, one of them comprising Component (a) and the other comprising Component (b).

The composition of memantine/solifenacin may be formulated in tablets in which one or both of the two components is in controlled-release form, for example as a dispersion of said component in hydroxypropyl-methyl-cellulose or in a film-coated microgranule.

Advantageously, memantine, preferably memantine hydrochloride in an ER-formulation and in an amount of 7 mg to 28 mg, is in the core, and solifenacin, preferably solifenacin succinate, in IR-formulation and in an amount of from 10 mg to 30 mg, is in the outer layer in a bilayer tablet in which, both the core and the outer layer may be coated with a film.

The memantine/solifenacin fixed-dose combination according to the present invention may be also formulated in a bi-layer tablet, the first layer containing memantine or a pharmaceutically acceptable salt thereof and the second one containing solifenacin or a pharmaceutically acceptable salt thereof. A third layer, free of active substances, could be inserted between said first and said second layer.

In said fixed dose combination, the retardant material of said first layer and the immediate release carrier second layer are two elements selected in order to allow respectively an extended (or sustained) release delivery of the memantine pharmaceutically acceptable salts, normally the hydrochloride, and to provide the solifenacin pharmaceutically acceptable salt, normally the succinate, in admixture with a pharmaceutical carrier for immediate release, for example according to the technologies described in U.S. Pat. No. 7,303,761 or in U.S. Pat. No. 8,802,143, the disclosures of which are incorporated herein in their entirety.

According to a fifth embodiment, the invention provides a pharmaceutical combination essentially consisting of
(a/d) a fixed-dose combination essentially consisting of a pharmaceutical composition in dosage unit form comprising
(a) memantine or a pharmaceutically acceptable salt thereof, in amount that is equivalent to from 5 mg to 30 mg of memantine hydrochloride; and
(d) a nsPAChA selected from the group consisting of solifenacin and pharmaceutically acceptable salts thereof, in an amount that is equivalent to from 10 mg to 30 mg of solifenacin succinate;
in admixture with a pharmaceutical carrier or vehicle;
(b) a pharmaceutical composition in dosage unit form comprising a naAEA; and
(c) a pharmaceutical composition in dosage unit form comprising a ChEI selected from the group consisting of donepezil and pharmaceutically acceptable salts thereof, in an amount that is equivalent to from 20 mg to 92 mg of donepezil hydrochloride, in admixture with a pharmaceutical carrier or vehicle.

An advantageous aspect of this fifth embodiment provides a combination essentially consisting of
(a/d) a fixed-dose combination essentially consisting of a pharmaceutical composition in dosage unit form comprising
(a) memantine or a pharmaceutically acceptable salt thereof, in amount that is equivalent to from 7 mg to 28 mg of memantine hydrochloride; and
(d) solifenacin or a pharmaceutically acceptable salt thereof, in an amount that is equivalent to from 10 mg to 30 mg of solifenacin succinate,
in admixture with a pharmaceutical carrier or vehicle; and
(b) a pharmaceutical composition in dosage unit form comprising a naAEA selected from the group consisting of alosetron and pharmaceutically acceptable salts and solvates thereof, in particular the hydrochloride, in an amount (in alosetron) of from 0.25 mg to 6 mg; azasetron and pharmaceutically acceptable salts and solvates thereof, in particular the hydrochloride, in an amount (in azasetron) of from 5 mg to 60 mg; dolasetron and pharmaceutically acceptable salts and solvates thereof, in particular the mesylate, in an amount (in dolasetron) of from 25 mg to 600 mg; granisetron and pharmaceutically acceptable salts and solvates thereof, in particular the hydrochloride, in an amount (in granisetron) of from 0.5 mg to 6 mg; ondansetron and pharmaceutically acceptable salts and solvates thereof, in particular the hydrochloride dihydrate, in an amount (in ondansetron) of from 2 mg to 64 mg; palonosetron and pharmaceutically acceptable salts and solvated thereof, in particular its hydrochloride, in an amount (in palonosetron) of from 0.25 mg to 3 mg; ramosetron and pharmaceutically acceptable salts and solvates thereof, in particular its hydrochloride, in an amount (in ramosetron) of from 0.0125 mg to 0.3 mg; tropisetron and pharmaceutically acceptable salts and solvates thereof, in particular the hydrochloride, in an amount of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine and pharmaceutically acceptable salts and solvates thereof, in particular the hydrochloride, in an amount (in chlorpromazine) of from 12.5 mg to 600 mg; prochlorperazine and pharmaceutically acceptable salts and solvates thereof, in particular the dimaleate, in an amount (in prochlorperazine) of from 2.5 mg to 30 mg; metoclopramide and pharmaceutically acceptable salts and solvates thereof, in particular the monohydrochloride monohydrate, in an amount (in metoclopramide) of from 5 mg to 60 mg; bromopride and pharmaceutically acceptable salts and solvates, in particular the monohydrochloride and the dihydrochloride monohydrate, in an amount (in bromopride) of from 5 mg to 60 mg; clebopride and pharmaceutically acceptable salts and solvates thereof, in particular the hydrogen malate and the hydrochloride monohydrate, in an amount (in clebopride) of from 0.25 mg to 3 mg; levosulpiride, in an amount of from 12.5 mg to 600 mg; alizapride and pharmaceutically acceptable salts thereof, in particular the hydrochloride, in an amount (in alizapride) of from 25 mg to 300 mg; trimethobenzamide and pharmaceutically acceptable salts thereof such as the monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine and pharmaceutically acceptable salts and solvates thereof, in particular the hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg, in admixture with a pharmaceutical carrier or vehicle; and
(c) donepezil or a pharmaceutically acceptable salts thereof, in an amount that is equivalent to from 25 mg to 92 mg or from 40 mg to 70 mg of donepezil hydrochloride, in a pharmaceutical composition in admixture with a pharmaceutical carrier or vehicle.

Preferably, the naAEA Component (b) in the (b/c) fixed-dose combination is selected from the group consisting of alosetron hydrochloride, in an amount (in alosetron) of from 0.25 mg to 6 mg; azasetron hydrochloride, in an amount (in azasetron) of from 5 mg to 60 mg; dolasetron mesylate, in an amount (in dolasetron) of from 25 mg to 600 mg; granisetron hydrochloride, in an amount (in granisetron) of from 0.5 mg to 6 mg; ondansetron hydrochloride dihydrate, in an amount (in ondansetron) of from 2 mg to 64 mg; palonosetron hydrochloride, in an amount (in palonosetron) of from 0.25 mg to 3 mg; ramosetron hydrochloride, in an amount (in ramosetron) of from 0.0125 mg to 0.3 mg, tropisetron hydrochloride, in an amount (in tropisetron) of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine hydrochloride, in an amount (in chlorpromazine) of from 12.5 mg to 600 mg; prochlorperazine dimaleate, in an amount (in prochlorperazine) of from 2.5 mg to 30 mg; metoclopramide monohydrochloride monohydrate, in an amount (in metoclopramide) of from 5 mg to 60 mg; bromopride monohydrochloride or dihydrochloride monohydrate, in an amount (in bromopride) of from 5 mg to 60 mg; clebopride hydrogen malate or hydrochloride monohydrate, in an amount (in clebopride) of from 0.25 mg to 3 mg; levosulpiride, in an amount of from 12.5 mg to 600 mg; alizapride hydrochloride, in an amount (in alizapride) of from 25 mg to 300 mg; trimethobenzamide monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg.

In a further fifth embodiment, the present invention provides a fixed-dose combination essentially consisting of a pharmaceutical composition comprising, as Components,
(d) memantine or a pharmaceutically acceptable salt thereof, in an amount that is equivalent to from 5 mg to 30 mg of memantine hydrochloride;
(e) solifenacin or a pharmaceutical acceptable salt thereof, in an amount that is equivalent to from 10 mg to 30 mg of solifenacin succinate, advantageously from 15 mg to 25 mg, preferably of 15 mg; and
(f) donepezil or a pharmaceutically acceptable salt thereof, in an amount that is equivalent to from 10 mg to 92 mg, preferably from 20 mg to 92 mg, normally from 10 mg to 70 mg, preferably from 20 mg to 70 mg, of donepezil hydrochloride,
in admixture with a pharmaceutical carrier or vehicle.

According to an advantageous aspect of this embodiment, the pharmaceutical composition comprises memantine hydrochloride, in an amount of from 5 mg to 30 mg, solifenacin succinate, in an amount of from 10 mg to 30 mg, advantageously from 15 mg to 25 mg, and donepezil hydrochloride, in an amount of from 10 mg to 92 mg, preferably from 20 mg to 92 mg, normally from 10 mg to 70 mg, preferably from 20 mg to 70 mg or from 40 mg to 70 mg.

A sixth embodiment of the present invention provides a combination essentially consisting of
(a) a pharmaceutical composition in dosage unit form comprising memantine or a pharmaceutically acceptable salt thereof, in amount that is equivalent to from 5 mg to 30 mg of memantine hydrochloride;
(b/c) a fixed dose combination consisting of a pharmaceutical composition in dosage unit form comprising
(a) a naAEA; and
(b) donepezil or a pharmaceutically acceptable salts thereof, in an amount that is equivalent to from 20 mg to 92 mg of donepezil hydrochloride,
in admixture with a pharmaceutical carrier or vehicle; and
(c) a pharmaceutical composition comprising a nsPAChA selected from the group consisting of solifenacin and pharmaceutically acceptable salts thereof, in an amount that is equivalent to from 10 mg to 30 mg of solifenacin succinate, in admixture with a pharmaceutical carrier or vehicle.

Normally, the naAEA component (b) is selected from the group consisting of (b1) 5HT3-antagonists; (b2) DA-antagonists; (b3) H1-antagonists; (b4) cannabinoids; (b5) NK1-antagonists.

Among the above (b1)-(b5) naAEA, a naAEA selected from the group consisting of alosetron and pharmaceutically acceptable salts and solvates thereof, in particular the hydrochloride, in an amount (in alosetron) of from 0.25 mg to 6 mg; azasetron and pharmaceutically acceptable salts and solvates thereof, in particular the hydrochloride, in an amount (in azasetron) of from 5 mg to 60 mg; dolasetron and pharmaceutically acceptable salts and solvates thereof, in particular the mesylate, in an amount (in dolasetron) of from 25 mg to 600 mg; granisetron and pharmaceutically acceptable salts and solvates thereof, in particular the hydrochloride, in an amount (in granisetron) of from 0.5 mg to 6 mg; ondansetron and pharmaceutically acceptable salts and solvates thereof, in particular the hydrochloride dihydrate, in an amount (in ondansetron) of from 2 mg to 64 mg; palonosetron and pharmaceutically acceptable salts and solvated thereof, in particular its hydrochloride, in an amount (in palonosetron) of from 0.25 mg to 3 mg; ramosetron and pharmaceutically acceptable salts and solvates thereof, in particular its hydrochloride, in an amount (in ramosetron) of from 0.0125 mg to 0.3 mg; tropisetron and pharmaceutically acceptable salts and solvates thereof, in particular the hydrochloride, in an amount of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine and pharmaceutically acceptable salts and solvates thereof, in particular the hydrochloride, in an amount (in chlorpromazine) of from 12.5 mg to 600 mg; prochlorperazine and pharmaceutically acceptable salts and solvates thereof, in particular the dimaleate, in an amount (in prochlorperazine) of from 2.5 mg to 30 mg; metoclopramide and pharmaceutically acceptable salts and solvates thereof, in particular the monohydrochloride monohydrate, in an amount (in metoclopramide) of from 5 mg to 60 mg; bromopride and pharmaceutically acceptable salts and solvates, in particular the monohydrochloride and the dihydrochloride monohydrate, in an amount (in bromopride) of from 5 mg to 60 mg; clebopride and pharmaceutically acceptable salts and solvates thereof, in particular the hydrogen malate and the hydrochloride monohydrate, in an amount (in clebopride) of from 0.25 mg to 3 mg; levosulpiride, in an amount of from 12.5 mg to 600 mg; alizapride and pharmaceutically acceptable salts thereof, in particular the hydrochloride, in an amount (in alizapride) of from 25 mg to 300 mg; trimethobenzamide and pharmaceutically acceptable salts thereof such as the monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine and pharmaceutically acceptable salts and solvates thereof, in particular the hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg, is particularly advantageous.

Preferably, in the pharmaceutical composition Component (b), the naAEA is selected from the group consisting of alosetron hydrochloride, in an amount (in alosetron) of from 0.25 mg to 6 mg; azasetron hydrochloride, in an amount (in azasetron) of from 5 mg to 60 mg; dolasetron mesylate, in an amount (in dolasetron) of from 25 mg to 600 mg; granisetron hydrochloride, in an amount (in granisetron) of from 0.5 mg to 6 mg; ondansetron hydrochloride dihydrate, in an amount (in ondansetron) of from 2 mg to 64 mg; palonosetron hydrochloride, in an amount (in palonosetron) of from 0.25 mg to 3 mg; ramosetron hydrochloride, in an amount (in ramosetron) of from 0.0125 mg to 0.3 mg; tropisetron hydrochloride, in an amount (in tropisetron) of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine hydrochloride, in an amount (in chlorpromazine) of from 12.5 mg to 600 mg; prochlorperazine dimaleate, in an amount (in prochlorperazine) of from 2.5 mg to 30 mg; metoclopramide monohydrochloride monohydrate, in an amount (in metoclopramide) of from 5 mg to 60 mg; bromopride monohydrochloride or dihydrochloride monohydrate, in an amount (in bromopride) of from 5 mg to 60 mg; clebopride hydrogen malate or hydrochloride monohydrate, in an amount (in clebopride) of from 0.25 mg to 3 mg; levosulpiride, in an amount of from 12.5 mg to 600 mg; alizapride hydrochloride, in an amount (in alizapride) of from 25 mg to 300 mg; trimethobenzamide monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg.

The ChEI/nsPAChA Component (c/d) of this sixth embodiment is illustrated in WO 2009/120227 (see also U.S. Pat. No. 9,044,472) and in WO 14/039627 (see also US 2015/0231122), the disclosures of which are incorporated herein in their entirety by reference.

Component (b) may be the brand palonosetron/netupitant (Akynzeo®) consisting of a capsule containing netupitant in an amount of 300 mg and palonosetron hydrochloride in an amount (in palonosetron) of 0.5 mg.

A seventh embodiment of the present invention provides a combination essentially consists of
(a) memantine or a pharmaceutically acceptable salt thereof, in amount that is equivalent to from 5 mg to 30 mg of memantine hydrochloride, in a pharmaceutical composition in dosage unit form, in admixture with a pharmaceutical carrier or vehicle;
(b) a naAEA selected from the group consisting of alosetron and pharmaceutically acceptable salts and solvates thereof, in particular the hydrochloride, in an amount (in alosetron) of from 0.25 mg to 6 mg; azasetron and pharmaceutically acceptable salts and solvates thereof, in particular the hydrochloride, in an amount (in azasetron) of from 5 mg to 60 mg; dolasetron and pharmaceutically acceptable salts and solvates thereof, in particular the mesylate, in an amount (in dolasetron) of from 25 mg to 600 mg; granisetron and pharmaceutically acceptable salts and solvates thereof, in particular the hydrochloride, in an amount (in granisetron) of from 0.5 mg to 6 mg; ondansetron and pharmaceutically acceptable salts and solvates thereof, in particular the hydrochloride dihydrate, in an amount (in ondansetron) of from 2 mg to 64 mg; palonosetron and pharmaceutically acceptable salts and solvated thereof, in particular its hydrochloride, in an amount (in palonosetron) of from 0.25 mg to 3 mg; ramosetron and pharmaceutically acceptable salts and solvates thereof, in particular its hydrochloride, in an amount (in ramosetron) of from 0.0125 mg to 0.3 mg; tropisetron and pharmaceutically acceptable salts and solvates thereof, in particular the hydrochloride, in an amount of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine and pharmaceutically acceptable salts and solvates thereof, in particular the hydrochloride, in an amount (in chlorpromazine) of from 12.5 mg to 600 mg; prochlorperazine and pharmaceutically acceptable salts and solvates thereof, in particular the dimaleate, in an amount (in prochlorperazine) of from 2.5 mg to 30 mg; metoclopramide and pharmaceutically acceptable salts and solvates thereof, in particular the monohydrochloride monohydrate, in an amount (in metoclopramide) of from 5 mg to 60 mg; bromopride and pharmaceutically acceptable salts and solvates, in particular the monohydrochloride and the dihydrochloride monohydrate, in an amount (in bromopride) of from 5 mg to 60 mg; clebopride and pharmaceutically acceptable salts and solvates thereof, in particular the hydrogen malate and the hydrochloride monohydrate, in an amount (in clebopride) of from 0.25 mg to 3 mg; levosulpiride, in an amount of from 12.5 mg to 600 mg; alizapride and pharmaceutically acceptable salts thereof, in particular the hydrochloride, in an amount (in alizapride) of from 25 mg to 300 mg; trimethobenzamide and pharmaceutically acceptable salts thereof such as the monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine and pharmaceutically acceptable salts and solvates thereof, in particular the hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg and
(c/d) a fixed-dose combination consisting of a pharmaceutical composition in dosage unit form comprising
(c) a ChEI selected from the group consisting of donepezil or a pharmaceutically acceptable salts thereof, in an amount that is equivalent to from 10 mg to 92 mg, preferably from 20 mg to 92 mg, normally from 10 mg to 70 mg, preferably from 20 mg to 70 mg of donepezil hydrochloride; and
(d) nsPAChA selected from the group consisting of solifenacin and pharmaceutically acceptable salts thereof, in an amount that is equivalent to from 10 mg to 30 mg, advantageously from 15 mg to 25 mg, preferably of 25 mg, of solifenacin succinate, in admixture with a pharmaceutical carrier or vehicle,
in admixture with a pharmaceutical carrier or vehicle.

Preferably, in the above (c/d) fixed-dose combination, the ChEI Component (c) is donepezil hydrochloride, in an amount of from 20 mg to 92 mg, advantageously from 20 mg to 70 mg and the nsPAChA is solifenacin succinate, in an amount of from 10 mg to 30 mg, preferably from 15 mg to 25 mg. As set forth above, in the case of particular necessities, especially for use in the titration phase of the therapy, the donepezil hydrochloride effective amount that is present in the above fixed-dose combinations Component (c/d), may be from 10 mg to 50 mg, in particular of 10 mg, 15 mg, 20 mg, 25 mg, 30 mg, 35 mg, 40 mg.

An advantageous aspect of this seventh embodiment comprises:
(a) a pharmaceutical composition in dosage unit form comprising or consisting essentially of memantine hydrochloride, in an amount of from 7 mg to 28 mg in admixture with a pharmaceutical carrier or vehicle in ER form
in admixture with a pharmaceutical carrier;
(b) a pharmaceutical composition comprising a naAEA selected from the group consisting of alosetron hydrochloride, in an amount (in alosetron) of from 0.25 mg to 6 mg; azasetron hydrochloride, in an amount (in azasetron) of from 5 mg to 60 mg; dolasetron mesylate, in an amount (in dolasetron) of from 25 mg to 600 mg; granisetron hydrochloride, in an amount (in granisetron) of from 0.5 mg to 6 mg; ondansetron hydrochloride dihydrate, in an amount (in ondansetron) of from 2 mg to 64 mg; palonosetron hydrochloride, in an amount (in palonosetron) of from 0.25 mg to 3 mg; ramosetron hydrochloride, in an amount (in ramosetron) of from 0.0125 mg to 0.3 mg, tropisetron hydrochloride, in an amount (in tropisetron) of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine hydrochloride, in an amount (in chlorpromazine) of from 12.5 mg to 600 mg; prochlorperazine dimaleate, in an amount (in prochlorperazine) of from 2.5 mg to 30 mg; metoclopramide monohydrochloride monohydrate, in an amount (in metoclopramide) of from 5 mg to 60 mg; bromopride monohydrochloride or dihydrochloride monohydrate, in an amount (in bromopride) of from 5 mg to 60 mg; clebopride hydrogen malate or hydrochloride monohydrate, in an amount (in clebopride) of from 0.25 mg to 3 mg; levosulpiride, in an amount of from 12.5 mg to 600 mg; alizapride hydrochloride, in an amount (in alizapride) of from 25 mg to 300 mg; trimethobenzamide monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg,
in admixture with a pharmaceutical carrier or vehicle; and
(c/d) a fixed-dose combination that is a pharmaceutical composition comprising or consisting essentially of
(c) solifenacin succinate, in an amount of 15 mg; and
(d) donepezil hydrochloride, in an amount of from 10 mg to 50 mg, normally from 10 mg to 40 mg,
in admixture with a pharmaceutical carrier or vehicle, in IR-form.

As set forth above, this composition is particularly useful in the titration phase of the treatment of a patient suffering from a hypocholinergic disorder and also during the treatment of said disorders, for donepezil doses up to 50 mg single or/daily dose.

According to an advantageous aspect of this seventh embodiment, the invention provides the above Component (c/d) as a pharmaceutical composition in dosage unit form in a novel formulation wherein the pharmaceutical carrier allows that said solifenacin succinate and donepezil hydrochloride do not interact each other.

In particular, donepezil hydrochloride and solifenacin succinate are present in specific percent amount and the pharmaceutical carrier comprises a diluent such as talc, powdered cellulose, lactose; a disaggregating agents such as microcrystalline cellulose, crospovidone or a starch, for example maize or corn starch; a lubricant such as magnesium or calcium stearate; and a binder, such as methyl cellulose, ethyl cellulose or hydroxypropyl methyl cellulose, each in specific percent amounts.

Specifically, the pharmaceutical carrier comprises lactose as a diluent; corn starch as a disaggregating agent; magnesium stearate as a lubricant and hydroxypropyl methyl cellulose as a binder.

Preferably, the pharmaceutical unit form comprising the preferred composition according to this third embodiment of the present invention is a coated tablet containing donepezil hydrochloride, in an amount of from 10 mg to 50 mg and solifenacin succinate, in an amount of 15 mg, as active ingredients, in the core, in admixture with a pharmaceutical carrier as defined above.

In particular, in the donepezil/solifenacin fixed-dose combination Component (c/d) essentially consists in a pharmaceutical composition in a dosage unit form consisting of a coated tablet comprising solifenacin succinate, in an amount of from 5.5% to 6.5%, donepezil hydrochloride, in an amount of from 4% to 20%; a diluent, in a amount of from 60% to 80%, a disaggregating agent, in a amount of from 6.8% to 7.5%; and a binder, in an amount of from 1.9% to 2.5% the total weight of the core. The coating is a nonenteric, fast-dissolving layer that covers the core according to known technologies. Normally, it is constituted by a cellulose derivative such as methyl hydroxyethyl cellulose or hydroxypropyl methyl cellulose, a glycerol ester such as diacetin or triacetin and a pigment such as titanium dioxide. Normally, the coating is Opadry®, especially the White 03K18533 type.

A eight embodiment of the present invention provides a pharmaceutical combination comprising
(a/b) a fixed-dose combination consisting of a pharmaceutical composition in dosage unit form comprising
(a) memantine or a pharmaceutically acceptable salt thereof, in amount that is equivalent to from 5 mg to 30 mg of memantine hydrochloride; and
(b) a naAEA selected from the group consisting of alosetron and pharmaceutically acceptable salts and solvates thereof, in particular the hydrochloride, in an amount (in alosetron) of from 0.25 mg to 6 mg; azasetron and pharmaceutically acceptable salts and solvates thereof, in particular the hydrochloride, in an amount (in azasetron) of from 5 mg to 60 mg; dolasetron and pharmaceutically acceptable salts and solvates thereof, in particular the mesylate, in an amount (in dolasetron) of from 25 mg to 600 mg; granisetron and pharmaceutically acceptable salts and solvates thereof, in particular the hydrochloride, in an amount (in granisetron) of from 0.5 mg to 6 mg; ondansetron and pharmaceutically acceptable salts and solvates thereof, in particular the hydrochloride dihydrate, in an amount (in ondansetron) of from 2 mg to 64 mg; palonosetron and pharmaceutically acceptable salts and solvated thereof, in particular its hydrochloride, in an amount (in palonosetron) of from 0.25 mg to 3 mg; ramosetron and pharmaceutically acceptable salts and solvates thereof, in particular its hydrochloride, in an amount (in ramosetron) of from 0.0125 mg to 0.3 mg; tropisetron and pharmaceutically acceptable salts and solvates thereof, in particular the hydrochloride, in an amount of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine and pharmaceutically acceptable salts and solvates thereof, in particular the hydrochloride, in an amount (in chlorpromazine) of from 12.5 mg to 600 mg; prochlorperazine and pharmaceutically acceptable salts and solvates thereof, in particular the dimaleate, in an amount (in prochlorperazine) of from 2.5 mg to 30 mg; metoclopramide and pharmaceutically acceptable salts and solvates thereof, in particular the monohydrochloride monohydrate, in an amount (in metoclopramide) of from 5 mg to 60 mg; bromopride and pharmaceutically acceptable salts and solvates, in particular the monohydrochloride and the dihydrochloride monohydrate, in an amount (in bromopride) of from 5 mg to 60 mg; clebopride and pharmaceutically acceptable salts and solvates thereof, in particular the hydrogen malate and the hydrochloride monohydrate, in an amount (in clebopride) of from 0.25 mg to 3 mg; levosulpiride, in an amount of from 12.5 mg to 600 mg; alizapride and pharmaceutically acceptable salts thereof, in particular the hydrochloride, in an amount (in alizapride) of from 25 mg to 300 mg; trimethobenzamide and pharmaceutically acceptable salts thereof such as the monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine and pharmaceutically acceptable salts and solvates thereof, in particular the hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg, in admixture with a pharmaceutical carrier or vehicle; and (c/d) a fixed-dose combination consisting of a pharmaceutical composition in dosage unit form comprising (c) donepezil or a pharmaceutically acceptable salts thereof, in an amount that is equivalent to from 10 mg to 92 mg, preferably from 20 mg to 92 mg, normally from 10 mg to 70 mg, preferably from 20 mg to 70 mg of donepezil hydrochloride; and (d) a nsPAChA selected from the group consisting of solifenacin and pharmaceutically acceptable salts thereof, in an amount that is equivalent to from 10 mg to 30 mg, advantageously from 15 mg to 25 mg, preferably of 15 mg of solifenacin succinate, in admixture with a pharmaceutical carrier or vehicle.

According to an advantageous aspect of this eight embodiment, the Component (a/b) is a pharmaceutical composition comprising (a) memantine hydrochloride, in an amount of from 5 mg to 30 mg, preferably from 7 mg to 28 mg; and (b); a naAEA selected from the group consisting of granisetron hydrochloride in an amount (in granisetron) of from 1 mg to 3 mg; domperidone in an amount of from 10 mg to 30 mg; metoclopramide monohydrochloride monohydrate in an amount (in metoclopramide) of from 10 mg to 30 mg; aprepitant, in an amount of from 40 mg to 375 mg, in admixture with a pharmaceutical carrier or vehicle.

According to a second advantageous aspect of this eight embodiment of the present invention the component (a/b) essentially consists of (a) memantine or a pharmaceutically acceptable salt thereof, in amount that is equivalent to from 5 mg to 30 mg of memantine hydrochloride; and (b) a naAEA selected from the group consisting of ondansetron and pharmaceutically acceptable salts and solvates thereof, in an amount (in ondansetron) of from 4 mg to 64 mg, in admixture with a pharmaceutical carrier or vehicle.

A specific component (a/b) according to this second advantageous aspect of this eight embodiment of the present invention essentially consists of (a) memantine or a pharmaceutically acceptable salt thereof, in amount that is equivalent to from 5 mg to 10 mg of memantine hydrochloride; and (b) a naAEA selected from the group consisting of ondansetron and pharmaceutically acceptable salts and solvates thereof, in an amount (in ondansetron) of from 4 mg to 32 mg, in admixture with a pharmaceutical carrier or vehicle in an IR-formulation.

A particularly preferred, specific Component (a/b) according to this second advantageous aspect of this eight embodiment of the present invention essentially consists of (a) memantine or a pharmaceutically acceptable salt thereof, in amount that is equivalent to from 7 mg to 28 mg of memantine hydrochloride; and (d) a naAEA selected from the group consisting of ondansetron and pharmaceutically acceptable salts and solvates thereof, in particular the hydrochloride dihydrate, in an amount (in ondansetron) of from 16 mg to 64 mg, in admixture with a pharmaceutical carrier or vehicle in an ER-formulation.

According to a ninth embodiment, the invention provides a combination essentially consists of (a/c) a fixed-dose combination consisting of a pharmaceutical composition in dosage unit form comprising (a) memantine or a pharmaceutically acceptable salt thereof, in amount that is equivalent to from 5 mg to 30 mg of memantine hydrochloride; and (c) donepezil or a pharmaceutically acceptable salts thereof, in an amount that is equivalent to from 10 mg to 92 mg, preferably from 20 mg to 92 mg, normally from 10 mg to 70 mg, preferably from 20 mg to 70 mg of donepezil hydrochloride, in a pharmaceutical composition in admixture with a pharmaceutical carrier or vehicle; and (b/d) a fixed-dose combination comprising (b) a naAEA selected from the group consisting of alosetron and pharmaceutically acceptable salts and solvates thereof, in particular the hydrochloride, in an amount (in alosetron) of from 0.25 mg to 6 mg; azasetron and pharmaceutically acceptable salts and solvates thereof, in particular the hydrochloride, in an amount (in azasetron) of from 5 mg to 60 mg; dolasetron and pharmaceutically acceptable salts and solvates thereof, in particular the mesylate, in an amount (in dolasetron) of from 25 mg to 600 mg; granisetron and pharmaceutically acceptable salts and solvates thereof, in particular the hydrochloride, in an amount (in granisetron) of from 0.5 mg to 6 mg; ondansetron and pharmaceutically acceptable salts and solvates thereof, in particular the hydrochloride dihydrate, in an amount (in ondansetron) of from 2 mg to 64 mg; palonosetron and pharmaceutically acceptable salts and solvated thereof, in particular its hydrochloride, in an amount (in palonosetron) of from 0.25 mg to 3 mg; ramosetron and pharmaceutically acceptable salts and solvates thereof, in particular its hydrochloride, in an amount (in ramosetron) of from 0.0125 mg to 0.3 mg; tropisetron and pharmaceutically acceptable salts and solvates thereof, in particular the hydrochloride, in an amount of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine and pharmaceutically acceptable salts and solvates thereof, in particular the hydrochloride, in an amount (in chlorpromazine) of from 12.5 mg to 600 mg; prochlorperazine and pharmaceutically acceptable salts and solvates thereof, in particular the dimaleate, in an amount (in prochlorperazine) of from 2.5 mg to 30 mg; metoclopramide and pharmaceutically acceptable salts and solvates thereof, in particular the monohydrochloride monohydrate, in an amount (in metoclopramide) of from 5 mg to 60 mg; bromopride and pharmaceutically acceptable salts and solvates, in particular the monohydrochloride and the dihydrochloride monohydrate, in an amount (in bromopride) of from 5 mg to 60 mg; clebopride and pharmaceutically acceptable salts and solvates thereof, in particular the hydrogen malate and the hydrochloride monohydrate, in an amount (in clebopride) of from 0.25 mg to 3 mg; levosulpiride, in an amount of from 12.5 mg to 600 mg; alizapride and pharmaceutically acceptable salts thereof, in particular the hydrochloride, in an amount (in alizapride) of from 25 mg to 300 mg; trimethobenzamide and pharmaceutically acceptable salts thereof such as the monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine and pharmaceutically acceptable salts and solvates thereof, in particular the hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg; and (d) a nsPAChA selected from the group consisting of solifenacin and pharmaceutically acceptable salts thereof, in an amount that is equivalent to from 10 mg to 30, advantageously from 15 mg to 25 mg, preferably of 15 mg of solifenacin succinate, in admixture with a pharmaceutical carrier or vehicle.

In said (b/d) fixed dose combination, the naAEA Component (b) is preferably selected from the group consisting of alosetron hydrochloride, in an amount (in alosetron) of from 0.25 mg to 6 mg; azasetron hydrochloride, in an amount (in azasetron) of from 5 mg to 60 mg; dolasetron mesylate, in an amount (in dolasetron) of from 25 mg to 600 mg; granisetron hydrochloride, in an amount (in granisetron) of from 0.5 mg to 6 mg; ondansetron hydrochloride dihydrate, in an amount (in ondansetron) of from 2 mg to 64 mg; palonosetron hydrochloride, in an amount (in palonosetron) of from 0.25 mg to 3 mg; ramosetron hydrochloride, in an amount (in ramosetron) of from 0.0125 mg to 0.3 mg, tropisetron hydrochloride, in an amount (in tropisetron) of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine hydrochloride, in an amount (in chlorpromazine) of from 12.5 mg to 600 mg; prochlorperazine dimaleate, in an amount (in prochlorperazine) of from 2.5 mg to 30 mg; metoclopramide monohydrochloride monohydrate, in an amount (in metoclopramide) of from 5 mg to 60 mg; bromopride monohydrochloride or dihydrochloride monohydrate, in an amount (in bromopride) of from 5 mg to 60 mg; clebopride hydrogen malate or hydrochloride monohydrate, in an amount (in clebopride) of from 0.25 mg to 3 mg; levosulpiride, in an amount of from 12.5 mg to 600 mg; alizapride hydrochloride, in an amount (in alizapride) of from 25 mg to 300 mg; trimethobenzamide monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg.

The Component (a/c) of the combination according to this ninth embodiment may be the brand memantine/donepezil fixed-dose combination comprising 7 mg-memantine/10 mg-donepezil (Namzaric® 7 mg/10 mg), which may be used in multiple unit forms per each administration, when 20 mg, 30 mg or 40 mg of donepezil are required.

The Component (b/d) of this ninth embodiment is exhaustively illustrated in WO 2014/039627 (see also US 2015/0231122), the disclosures of which are incorporated herein in their entirety by reference, the disclosure of which is incorporated herein in its entirety for reference.

According to a preferred aspect of this ninth embodiment, the Component (b/d) is a pharmaceutical composition comprising (b) a naAEA selected from the group consisting of granisetron hydrochloride in an amount (in granisetron) of from 1 mg to 3 mg, ondansetron hydrochloride dihydrate in an amount (in ondansetron) of from 4 mg to 24 mg, domperidone in an amount of from 10 mg to 30 mg; metoclopramide monohydrochloride monohydrate in an amount (in metoclopramide) of from 10 mg to 30 mg; aprepitant, in an amount of from 40 mg to 375 mg; and (d) solifenacin succinate in an amount of from 10 mg to 30 mg, advantageously from 15 mg to 25 mg, preferably of 15 mg, in admixture with a pharmaceutical carrier.

According to a tenth embodiment, the invention provides a pharmaceutical combination comprising (a/d) a fixed-dose combination essentially consisting of a pharmaceutical composition in dosage unit form comprising (a) a NMDA-antagonist selected from the group consisting of memantine or a pharmaceutically acceptable salt thereof, in amount that is equivalent to from 5 mg to 30 mg of memantine hydrochloride; and (d) a nsPAChA selected from the group consisting of solifenacin and pharmaceutically acceptable salts thereof, in an amount that is equivalent to from 10 mg to 30 mg of solifenacin succinate;

in admixture with a pharmaceutical carrier or vehicle; and (b/c) a fixed-dose combination essentially consisting of a pharmaceutical composition in dosage unit form comprising (b) a naAEA; and (c) a ChEI selected from the group consisting of donepezil and pharmaceutically acceptable salts thereof, in an amount that is equivalent to from 10 mg to 92 mg, preferably from 20 mg to 92 mg, normally from 10 mg to 70 mg, preferably from 20 mg to 70 mg of donepezil hydrochloride,
in admixture with a pharmaceutical carrier or vehicle.

An advantageous aspect of this tenth embodiment provides a combination essentially consisting of
(a/d) a fixed-dose combination essentially consisting of a pharmaceutical composition in dosage unit form comprising
(a) memantine or a pharmaceutically acceptable salt thereof, in amount that is equivalent to from 7 mg to 28 mg of memantine hydrochloride; and
(d) solifenacin or a pharmaceutically acceptable salt thereof, in an amount that is equivalent to from 10 mg to 30 mg, advantageously from 15 mg to 25 mg, preferably 15 mg of solifenacin succinate,
in admixture with a pharmaceutical carrier or vehicle; and
(b/c) a fixed-dose combination essentially consisting of a pharmaceutical composition in dosage unit form comprising
(b) a pharmaceutical composition in dosage unit form comprising a naAEA selected from the group consisting of alosetron and pharmaceutically acceptable salts and solvates thereof, in particular the hydrochloride, in an amount (in alosetron) of from 0.25 mg to 6 mg; azasetron and pharmaceutically acceptable salts and solvates thereof, in particular the hydrochloride, in an amount (in azasetron) of from 5 mg to 60 mg; dolasetron and pharmaceutically acceptable salts and solvates thereof, in particular the mesylate, in an amount (in dolasetron) of from 25 mg to 600 mg; granisetron and pharmaceutically acceptable salts and solvates thereof, in particular the hydrochloride, in an amount (in granisetron) of from 0.5 mg to 6 mg; ondansetron and pharmaceutically acceptable salts and solvates thereof, in particular the hydrochloride dihydrate, in an amount (in ondansetron) of from 2 mg to 64 mg; palonosetron and pharmaceutically acceptable salts and solvated thereof, in particular its hydrochloride, in an amount (in palonosetron) of from 0.25 mg to 3 mg; ramosetron and pharmaceutically acceptable salts and solvates thereof, in particular its hydrochloride, in an amount (in ramosetron) of from 0.0125 mg to 0.3 mg; tropisetron and pharmaceutically acceptable salts and solvates thereof, in particular the hydrochloride, in an amount of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine and pharmaceutically acceptable salts and solvates thereof, in particular the hydrochloride, in an amount (in chlorpromazine) of from 12.5 mg to 600 mg; prochlorperazine and pharmaceutically acceptable salts and solvates thereof, in particular the dimaleate, in an amount (in prochlorperazine) of from 2.5 mg to 30 mg; metoclopramide and pharmaceutically acceptable salts and solvates thereof, in particular the monohydrochloride monohydrate, in an amount (in metoclopramide) of from 5 mg to 60 mg; bromopride and pharmaceutically acceptable salts and solvates, in particular the monohydrochloride and the dihydrochloride monohydrate, in an amount (in bromopride) of from 5 mg to 60 mg; clebopride and pharmaceutically acceptable salts and solvates thereof, in particular the hydrogen malate and the hydrochloride monohydrate, in an amount (in clebopride) of from 0.25 mg to 3 mg; levosulpiride, in an amount of from 12.5 mg to 600 mg; alizapride and pharmaceutically acceptable salts thereof, in particular the hydrochloride, in an amount (in alizapride) of from 25 mg to 300 mg; trimethobenzamide and pharmaceutically acceptable salts thereof such as the monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine and pharmaceutically acceptable salts and solvates thereof, in particular the hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg, in admixture with a pharmaceutical carrier or vehicle; and
(c) donepezil or a pharmaceutically acceptable salts thereof, in an amount that is equivalent to from 10 mg to 92 mg, preferably from 20 mg to 92 mg, normally from 10 mg to 70 mg, preferably from 20 mg to 70 mg of donepezil hydrochloride, in a pharmaceutical composition in admixture with a pharmaceutical carrier or vehicle.

Preferably, in the Component ((b/c) fixed-dose combination the NMDA-antagonist Component (a) is memantine hydrochloride and the naAEA Component (b) is selected from the group consisting of alosetron hydrochloride, in an amount (in alosetron) of from 0.25 mg to 6 mg; azasetron hydrochloride, in an amount (in azasetron) of from 5 mg to 60 mg; dolasetron mesylate, in an amount (in dolasetron) of from 25 mg to 600 mg; granisetron hydrochloride, in an amount (in granisetron) of from 0.5 mg to 6 mg; ondansetron hydrochloride dihydrate, in an amount (in ondansetron) of from 2 mg to 64 mg; palonosetron hydrochloride, in an amount (in palonosetron) of from 0.25 mg to 3 mg; ramosetron hydrochloride, in an amount (in ramosetron) of from 0.0125 mg to 0.3 mg, tropisetron hydrochloride, in an amount (in tropisetron) of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine hydrochloride, in an amount (in chlorpromazine) of from 12.5 mg to 600 mg; prochlorperazine dimaleate, in an amount (in prochlorperazine) of from 2.5 mg to 30 mg; metoclopramide monohydrochloride monohydrate, in an amount (in metoclopramide) of from 5 mg to 60 mg; bromopride monohydrochloride or dihydrochloride monohydrate, in an amount (in bromopride) of from 5 mg to 60 mg; clebopride hydrogen malate or hydrochloride monohydrate, in an amount (in clebopride) of from 0.25 mg to 3 mg; levosulpiride, in an amount of from 12.5 mg to 600 mg; alizapride hydrochloride, in an amount (in alizapride) of from 25 mg to 300 mg; trimethobenzamide monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg.

The Component (c/d), consisting of a pharmaceutical composition comprising the ChEI donepezil and the nsPAChA solifenacin, is illustrated in the aforementioned WO 2009/120277 (see also U.S. Pat. No. 9,044,472), the disclosures of which are incorporated herein in their entirety by reference. According to a third advantageous aspect of this tenth embodiment, said Component (c/d) is a pharmaceutically composition in dosage unit form comprising solifenacin succinate, in an amount of from 10 mg to 30 mg and donepezil hydrochloride, in an amount of from 10 mg to 92 mg, preferably from 20 mg to 92 mg, normally from 10 mg to 70 mg, preferably from 20 mg to 70 mg, in admixture with a pharmaceutical carrier or vehicle.

According to an eleventh embodiment, the invention provides a pharmaceutical combination comprising or essentially consisting of
(a) a pharmaceutical composition in dosage unit form comprising memantine or a pharmaceutically acceptable salt thereof, in an amount corresponding to from 5 mg to 30 mg of memantine hydrochloride; and
(b/c/d) a fixed-dose combination consisting of a pharmaceutical composition in dosage unit form comprising
(b) a naAEA;
(c) donepezil or a pharmaceutically acceptable salt thereof, in an amount that is equivalent to from 10 mg to 92 mg, preferably from 20 mg to 92 mg, normally from 10 mg to 70 mg, preferably from 20 mg to 70 mg of donepezil hydrochloride; and
(d) solifenacin or a pharmaceutically acceptable salt thereof, in an amount that is equivalent to from 10 mg to 30 mg, advantageously fro 15 mg to 25 mg, preferably of 15 mg of solifenacin succinate,
in admixture with a pharmaceutical carrier or vehicle.

An advantageous aspect of this eleventh embodiment of the present invention provides the above (a)-(b/c/d) combination, wherein
said Component (a) is a pharmaceutical composition comprising memantine hydrochloride in an amount of from 7 mg to 28 mg in a IR- or ER-formulation; and
said Component (b/c/d) is a pharmaceutical composition comprising
(b) a naAEA selected from the group consisting of alosetron hydrochloride, in an amount (in alosetron) of from 0.25 mg to 6 mg; azasetron hydrochloride, in an amount (in azasetron) of from 5 mg to 60 mg; dolasetron mesylate, in an amount (in dolasetron) of from 25 mg to 600 mg; granisetron hydrochloride, in an amount (in granisetron) of from 0.5 mg to 6 mg; ondansetron hydrochloride dihydrate, in an amount (in ondansetron) of from 2 mg to 64 mg; palonosetron hydrochloride, in an amount (in palonosetron) of from 0.25 mg to 3 mg; ramosetron hydrochloride, in an amount (in ramosetron) of from 0.0125 mg to 0.3 mg; tropisetron hydrochloride, in an amount of from 2.5 mg to 30 mg; domperidone, in an amount of from 5 mg to 60 mg; haloperidol, in an amount of from 0.5 mg to 60 mg; chlorpromazine hydrochloride, in an amount (in chlorpromazine) of from 12.5 mg to 600 mg; prochlorperazine dimaleate, in an amount (in prochlorperazine) of from 2.5 mg to 30 mg; metoclopramide monohydrochloride monohydrate, in an amount (in metoclopramide) of from 5 mg to 60 mg; bromopride monohydrochloride or bromopride dihydrochloride monohydrate, in an amount (in bromopride) of from 5 mg to 60 mg; clebopride hydrogen malate or clebopride hydrochloride monohydrate, in an amount (in clebopride) of from 0.25 mg to 3 mg; levosulpiride, in an amount of from 12.5 mg to 600 mg; alizapride hydrochloride, in an amount (in alizapride) of from 25 mg to 300 mg; trimethobenzamide monohydrochloride, in an amount (in trimethobenzamide) of from 50 mg to 600 mg; meclizine, in an amount of from 6.25 mg to 300 mg; promethazine hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg;
(c) donepezil hydrochloride in an amount of from 10 mg to 92 mg, preferably from 20 mg to 92 mg, normally from 10 mg to 70 mg, preferably from 20 mg to 70 mg; and
(d) solifenacin succinate in an amount of from 10 mg to 30 mg, advantageously from 15 mg to 25 mg. preferably of 15 mg,
in admixture with a pharmaceutical carrier or vehicle.

A second advantageous aspect of this eleventh embodiment of the present invention provides the above (a)-(b/c/d) combination, wherein said Component (a) is memantine hydrochloride in a pharmaceutical composition comprising memantine or a pharmaceutically acceptable salt thereof, in an amount of from 7 mg to 28 mg in a ER-formulation, such as the ER-capsules of the brand drug known as Namenda® XR.

According to a twelfth embodiment, the invention provides a pharmaceutical combination comprising or essentially consisting of
(b) a pharmaceutical composition in dosage unit form comprising a naAEA; and
(a/c/d) a fixed-dose combination consisting of a pharmaceutical composition in dosage unit form comprising
(a) memantine or a pharmaceutically acceptable salt thereof, in an amount corresponding to from 5 mg to 30 mg of memantine hydrochloride;
(c) donepezil or a pharmaceutically acceptable salt thereof, in an amount that is equivalent to from 10 mg to 92 mg, preferably from 20 mg to 92 mg, normally from 10 mg to 70 mg, preferably from 20 mg to 70 mg of donepezil hydrochloride; and
(d) solifenacin or a pharmaceutically acceptable salt thereof, in an amount that is equivalent to from 10 mg to 30 mg, advantageously from 15 mg to 25 mg, preferably of 15 mg of solifenacin succinate,
in admixture with a pharmaceutical carrier or vehicle.

A first aspect of this twelfth embodiment of the present invention provides the above (b)-(a/c/d) combination, wherein
said Component (b) is a naAEA selected from the group consisting of alosetron and pharmaceutically acceptable salts and solvates thereof, in particular the hydrochloride, in an amount (in alosetron) of from 0.25 mg to 6 mg; azasetron and pharmaceutically acceptable salts and solvates thereof, in particular the hydrochloride, in an amount (in azasetron) of from 5 mg to 60 mg; dolasetron and pharmaceutically acceptable salts and solvates thereof, in particular the mesylate, in an amount (in dolasetron) of from 25 mg to 600 mg; granisetron and pharmaceutically acceptable salts and solvates thereof, in particular the hydrochloride, in an amount (in granisetron) of from 0.5 mg to 6 mg; ondansetron and pharmaceutically acceptable salts and solvates thereof, in particular the hydrochloride dihydrate, in an amount (in ondansetron) of from 2 mg to 64 mg; palonosetron and pharmaceutically acceptable salts and solvated thereof, in particular its hydrochloride, in an amount (in palonosetron) of from 0.25 mg to 3 mg; ramosetron and pharmaceutically acceptable salts and solvates thereof, in particular its hydrochloride, in an amount (in ramosetron) of from 0.0125 mg to 0.3 mg; tropisetron and pharmaceutically acceptable salts and solvates thereof, in particular the hydrochloride, in an amount of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine and pharmaceutically acceptable salts and solvates thereof, in particular the hydrochloride, in an amount (in chlorpromazine) of from 12.5 mg to 600 mg; prochlorperazine and pharmaceutically acceptable salts and solvates thereof, in particular the dimaleate, in an amount (in prochlorperazine) of from 2.5 mg to 30 mg; metoclopramide and pharmaceutically acceptable salts and solvates thereof, in particular the monohydrochloride monohydrate, in an amount (in metoclopramide) of from 5 mg to 60 mg; bromopride and pharmaceutically acceptable salts and solvates, in particular the monohydrochloride and the dihydrochloride monohydrate, in an amount (in bromopride) of from 5 mg to 60 mg; clebopride and pharmaceutically acceptable salts and solvates thereof, in particular the hydrogen malate and the hydrochloride monohydrate, in an amount (in clebopride) of from 0.25 mg to 3 mg; levosulpiride, in an amount of from 12.5 mg to 600 mg; alizapride and pharmaceutically acceptable salts thereof, in particular the hydrochloride, in an amount (in alizapride) of from 25 mg to 300 mg; trimethobenzamide and pharmaceutically acceptable salts thereof such as the monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine and pharmaceutically acceptable salts and solvates thereof, in particular the hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg; and, in the fixed-dose combination Component (a/c/d)

said Component (a) is memantine hydrochloride, in an amount of from 7 mg to 28 mg;

said Component (c) is donepezil hydrochloride, in an amount of from 10 mg to 92 mg, normally from 10 mg to 70 mg; and said Component (d) is solifenacin succinate, in an amount of from 10 mg to 30 mg, advantageously from 15 mg to 25 mg preferably of 15 mg.

A second advantageous aspect of this twelfth embodiment of the present invention provides the above (b)-(a/b/d) combination essentially consisting of (b) a fixed-dose combination consisting of a pharmaceutical composition in dosage unit form comprising palonosetron hydrochloride, in an amount (in palonosetron) of 0.5 mg, and netupitant, in an amount of 300 mg, in admixture with a pharmaceutical carrier or vehicle; and (a/c/d) a pharmaceutical composition in dosage unit form comprising (a) memantine hydrochloride, in an amount of from 7 mg to 28 mg;

(c) donepezil hydrochloride, in an amount of from 10 mg to 92 mg; and (d) solifenacin succinate, in an amount of from 10 mg to 30 mg, in admixture with a pharmaceutical carrier or vehicle.

The above fixed-dose combination Component (b) may be the palonosetron/netupitant brand drug known as Akynzeo®.

According to a thirteenth embodiment, the invention provides a pharmaceutical combination comprising or essentially consisting of (c) a pharmaceutical composition in dosage unit form comprising donepezil or a pharmaceutically acceptable salt thereof, in an amount that is equivalent to from 10 mg to 92 mg, preferably from 20 mg to 92 mg, normally from 10 mg to 70 mg, preferably from 20 mg to 70 mg of donepezil hydrochloride; and;

(a/b/d) a fixed-dose combination consisting of a pharmaceutical composition in dosage unit form comprising (a) memantine or a pharmaceutically acceptable salt thereof, in an amount corresponding to from 5 mg to 30 mg of memantine hydrochloride;

(b) a naAEA; and (d) solifenacin or a pharmaceutically acceptable salt thereof, in an amount that is equivalent to from 10 mg to 30 mg of solifenacin succinate, in admixture with a pharmaceutical carrier or vehicle.

An advantageous aspect of this thirteenth embodiment of the present invention provides the above (c)-(a/b/d) combination, wherein said Component (c) is a pharmaceutical composition comprising donepezil hydrochloride in an amount of from 10 mg to 92 mg; and said Component (a/b/d) is a pharmaceutical composition in dosage unit form comprising (a) memantine hydrochloride in an amount of from 5 mg to 30 mg;

(b) a naAEA selected from the group consisting of alosetron hydrochloride, in an amount (in alosetron) of from 0.25 mg to 6 mg; azasetron hydrochloride, in an amount (in azasetron) of from 5 mg to 60 mg; dolasetron mesylate, in an amount (in dolasetron) of from 25 mg to 600 mg; granisetron hydrochloride, in an amount (in granisetron) of from 0.5 mg to 6 mg; ondansetron hydrochloride dihydrate, in an amount (in ondansetron) of from 2 mg to 64 mg; palonosetron hydrochloride, in an amount (in palonosetron) of from 0.25 mg to 3 mg; ramosetron hydrochloride, in an amount (in ramosetron) of from 0.0125 mg to 0.3 mg; tropisetron hydrochloride, in an amount of from 2.5 mg to 30 mg; domperidone, in an amount of from 5 mg to 60 mg; haloperidol, in an amount of from 0.5 mg to 60 mg; chlorpromazine hydrochloride, in an amount (in chlorpromazine) of from 12.5 mg to 600 mg; prochlorperazine dimaleate, in an amount (in prochlorperazine) of from 2.5 mg to 30 mg; metoclopramide monohydrochloride monohydrate, in an amount (in metoclopramide) of from 5 mg to 60 mg; bromopride monohydrochloride or bromopride dihydrochloride monohydrate, in an amount (in bromopride) of from 5 mg to 60 mg; clebopride hydrogen malate or clebopride hydrochloride monohydrate, in an amount (in clebopride) of from 0.25 mg to 3 mg; levosulpiride, in an amount of from 12.5 mg to 600 mg; alizapride hydrochloride, in an amount (in alizapride) of from 25 mg to 300 mg; trimethobenzamide monohydrochloride, in an amount (in trimethobenzamide) of from 50 mg to 600 mg; meclizine (also called meclozine), in an amount of from 6.25 mg to 300 mg; promethazine hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 900 mg; rolapitant, in an amount of from 30 mg to 360 mg; and casopitant, in an amount of from 25 mg to 300 mg; and (d) solifenacin succinate in an amount of from 10 mg to 30 mg, in admixture with a pharmaceutical carrier or vehicle.

According to a fourteenth embodiment, the invention provides a pharmaceutical combination comprising or essentially consisting of (d) a pharmaceutical composition in dosage unit form comprising solifenacin or a pharmaceutically acceptable salt thereof, in an amount that is equivalent to from 10 mg to 30 mg, advantageously from 15 mg to 25 mg, preferably of 15 mg of solifenacin succinate, in admixture with a pharmaceutical carrier or vehicle; and (a/b/c) a fixed-dose combination consisting of a pharmaceutical composition in dosage unit form comprising (a) memantine or a pharmaceutically acceptable salt thereof, in an amount corresponding to from 5 mg to 30 mg of memantine hydrochloride;

(b) a naAEA; and (c) donepezil or a pharmaceutically acceptable salt thereof, in an amount that is equivalent to from 10 mg to 92 mg of donepezil hydrochloride, in admixture with a pharmaceutical carrier or vehicle.

A second advantageous aspect of this fourteenth embodiment of the present invention provides the above (d)-(a/b/c) combination, wherein said Component (d) in the (a/b/c) fixed-dose combination is a naAEA selected from the group consisting of alosetron and pharmaceutically acceptable salts and solvates thereof, in particular the hydrochloride, in an amount (in alosetron) of from 0.25 mg to 6 mg; azasetron and pharmaceutically acceptable salts and solvates thereof, in particular the hydrochloride, in an amount (in azasetron) of from 5 mg to 60 mg; dolasetron and pharmaceutically acceptable salts and solvates thereof, in particular the mesylate, in an amount (in dolasetron) of from 25 mg to 600 mg; granisetron and pharmaceutically acceptable salts and solvates thereof, in particular the hydrochloride, in an amount (in granisetron) of from 0.5 mg to 6 mg; ondansetron and pharmaceutically acceptable salts and solvates thereof, in particular the hydrochloride dihydrate, in an amount (in ondansetron) of from 2 mg to 64 mg; palonosetron and pharmaceutically acceptable salts and solvated thereof, in particular its hydrochloride, in an amount (in palonosetron) of from 0.25 mg to 3 mg; ramosetron and pharmaceutically acceptable salts and solvates thereof, in particular its hydrochloride, in an amount (in ramosetron) of from 0.0125 mg to 0.3 mg; tropisetron and pharmaceutically acceptable salts and solvates thereof, in particular the hydrochloride, in an amount of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine and pharmaceutically acceptable salts and solvates thereof, in particular the hydrochloride, in an amount (in chlorpromazine) of from 12.5 mg to 600 mg; prochlorperazine and pharmaceutically acceptable salts and solvates thereof, in particular the dimaleate, in an amount (in prochlorperazine) of from 2.5 mg to 30 mg; metoclopramide and pharmaceutically acceptable salts and solvates thereof, in particular the monohydrochloride monohydrate, in an amount (in metoclopramide) of from 5 mg to 60 mg; bromopride and pharmaceutically acceptable salts and solvates, in particular the monohydrochloride and the dihydrochloride monohydrate, in an amount (in bromopride) of from 5 mg to 60 mg; clebopride and pharmaceutically acceptable salts and solvates thereof, in particular the hydrogen malate and the hydrochloride monohydrate, in an amount (in clebopride) of from 0.25 mg to 3 mg; levosulpiride, in an amount of from 12.5 mg to 600 mg; alizapride and pharmaceutically acceptable salts thereof, in particular the hydrochloride, in an amount (in alizapride) of from 25 mg to 300 mg; trimethobenzamide and pharmaceutically acceptable salts thereof such as the monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine and pharmaceutically acceptable salts and solvates thereof, in particular the hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg, in admixture with a pharmaceutical carrier or vehicle.

A third advantageous aspect of this fourteenth embodiment, of the present invention provides the above (d)-(a/b/c) combination essentially consisting of (d) a pharmaceutical composition in dosage unit form comprising solifenacin succinate, in an amount of from 10 mg to 30 mg, advantageously from 15 mg to 25 mg, preferably of 15 mg, in admixture with a pharmaceutical carrier or vehicle; and (a/b/c) a fixed-dose combination consisting of a pharmaceutical composition in dosage unit form comprising (a) memantine hydrochloride, in an amount of from 5 mg to 30 mg;

(b) a naAEA selected from the group consisting of alosetron hydrochloride, in an amount (in alosetron) of from 0.25 mg to 6 mg; azasetron hydrochloride, in an amount (in azasetron) of from 5 mg to 60 mg; dolasetron mesylate, in an amount (in dolasetron) of from 25 mg to 600 mg; granisetron hydrochloride, in an amount (in granisetron) of from 0.5 mg to 6 mg; ondansetron hydrochloride dihydrate, in an amount (in ondansetron) of from 2 mg to 64 mg; palonosetron hydrochloride, in an amount (in palonosetron) of from 0.25 mg to 3 mg; ramosetron hydrochloride, in an amount (in ramosetron) of from 0.0125 mg to 0.3 mg; tropisetron hydrochloride, in an amount of from 2.5 mg to 30 mg; domperidone, in an amount of from 5 mg to 60 mg; haloperidol, in an amount of from 0.5 mg to 60 mg; chlorpromazine hydrochloride, in an amount (in chlorpromazine) of from 12.5 mg to 600 mg; prochlorperazine dimaleate, in an amount (in prochlorperazine) of from 2.5 mg to 30 mg; metoclopramide monohydrochloride monohydrate, in an amount (in metoclopramide) of from 5 mg to 60 mg; bromopride monohydrochloride or bromopride dihydrochloride monohydrate, in an amount (in bromopride) of from 5 mg to 60 mg; clebopride hydrogen malate or clebopride hydrochloride monohydrate, in an amount (in clebopride) of from 0.25 mg to 3 mg; levosulpiride, in an amount of from 12.5 mg to 600 mg; alizapride hydrochloride, in an amount (in alizapride) of from 25 mg to 300 mg; trimethobenzamide monohydrochloride, in an amount (in trimethobenzamide) of from 50 mg to 600 mg; in an amount of from 6.25 mg to 300 mg; promethazine hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg; and (c) donepezil hydrochloride, in an amount of from 10 mg to 92 mg, preferably from 20 mg to 92 mg, normally from 10 mg to 70 mg, preferably from 20 mg to 70 mg, in admixture with a pharmaceutical carrier or vehicle.

A third advantageous aspect of this fourteenth embodiment of the present invention provides the above (d)-(a/b/c) combination, wherein said Component (a/b/c) essentially consisting of a pharmaceutical composition in dosage unit form comprising (a) memantine hydrochloride, in an amount of from 7 mg to 28 mg;

(b) solifenacin succinate, in an amount of from 10 mg to 30 mg; and (c) donepezil hydrochloride, in an amount of from 10 mg to 92 mg, in admixture with a pharmaceutical carrier or vehicle.

A fourth advantageous aspect of this fourteenth embodiment of the present invention provides a (d)-(a/b/c) combination, essentially consisting of (d) a pharmaceutical composition in dosage unit form comprising solifenacin succinate in an amount of from 10 mg to 30 mg, advantageously from 15 mg to 25 mg, preferably of 15 mg; and (a/b/c) a fixed-dose combination consisting of a pharmaceutical composition in dosage unit form comprising (a) memantine hydrochloride, in an amount of from 7 mg to 28 mg;

(b) aprepitant, in an amount of 40 mg; and (c) donepezil hydrochloride in an amount of from 10 mg to 70 mg, in admixture with a pharmaceutical carrier or vehicle.

All the aforementioned pharmaceutical compositions, comprising Component (a), Component (b), Component (c), Component (d) or mixtures thereof in fixed-dose combinations, are preferably in dosage unit form wherein each of the active ingredients or mixtures thereof formulated in admixture with a pharmaceutical carrier.

The pharmaceutical carrier or vehicles and vehicles are those commonly used for the preparation of compositions for oral, buccal and parenteral, in particular transdermal, administration. Oral forms such as tablets, soft or hard gelatin capsules, powders or granulates in sachets and suitably measured oral solutions or suspensions as well as patches for transdermal administration are particularly appropriate unit forms.

In said unit form, memantine Component (a), preferably memantine hydrochloride, the naAEA Component (b) donepezil Component (c), especially donepezil hydrochloride, and solifenacin Component (d), especially solifenacin succinate, are mixed, together or separately, according to known technologies, in admixture with a pharmaceutical carriers or vehicles, in pharmaceutical compositions according to the above fourteen embodiments.

Carrier or vehicles for IR tablets include for example starches, cellulose and derivatives thereof; lubricants such as talc, stearic acid or magnesium stearate; diluents such as talc, powdered cellulose, lactose, starches such as maize or corn starch, mannitol, sorbitol; disaggregating agents such as microcrystalline cellulose or crospovidone; lubricants such as polyethylene glycol or magnesium stearate; ligands such as methylcellulose, sodium carboxymethylcellulose, alginic acid, alginates; sweeteners, such as suchrose, dextrose, mannitol, saccharin; or flavoring agents such as natural or synthetic oils.

Carriers or vehicles for orally disintegrating tablets include for example lubricants, aggregating, sweetening, flavoring or disaggregating agents as well as agents improving the buccal mucosa absorption of Component (a) and/or Component (b) and/or Component (d) such as sorbitol, mannitol, lactose and cellulose.

Carriers or vehicles for liquid, normally aqueous, suspensions or solutions include for example antioxidants, such as sodium metabisulfite or sodium sulfite, thickening agents, such as microcrystalline cellulose, hydroxypropylcellulose, carboxymethylcellulose or polyvinylpyrrolidone, presevatives such as methyl paraben, ethyl paraben, tetra-sodium ethylenediaminotetracetate (sodium edentate), sodium benzoate or an alkaline salt of sorbic acid, as well as flavoring and sweetening agents.

The sweeteners contained in the orally disintegrating tablets and the liquid suspensions or solutions may be natural, optional reduced sugars such as sucrose, dextrose, xylitol, mannitol or sorbitol, or synthetic product such as sodium saccharine or aspartame.

The flavoring agents are pharmaceutically acceptable flavors and tastes of synthetic and natural oils, the latter extracted from plants, leaves, flowers, fruits and their combinations, such as cinnamon, peppermint, anise and citron leaves, bitter almond, citrus fruits, in particular orange and/or lemon, linden and grapefruit oils. Also chocolate, vanilla or eucalyptus flavor and essences of fruit, in particular apple, pear, peach, strawberry, cherry, apricot, orange, lemon and grapes may be advantageously used.

According to an embodiment, memantine Component (a) and the naAEA Component (b) are advantageously combined in a fixed dose combination for the simultaneous administration of the two Components, as disclosed herein above as the fifth embodiment and the tenth embodiment of the invention. This fixed dose combination is for use for the treatment of a patient suffering from of a hypocholinergic disorder such as Alzheimer type dementia, in combination with donepezil Component (c) and solifenacin Component (d), concurrently or separately administered to said patient in need of said treatment.

For oral use, memantine Component (a) and the naAEA Component (b) are in compositions in admixture with pharmaceutical excipients in known formulations wherein said Components are mixed together or separated, for example in two tablets introduced in a capsule, or in a two-compartment capsule or in a multilayer (dilayer) tablet wherein the two components, for example memantine hydrochloride and ondansetron hydrochloride dihydrate are both in IR form, or wherein the memantine pharmaceutically acceptable salt, especially the hydrochloride, is in ER-form, and the naAEA, for example aprepitant, is in IR-form, according to the technologies disclosed for example in U.S. Pat. No. 7,303, 761 or 8,802,143, the disclosures of which are incorporated herein in their entirety for reference.

Component (a) and Component (b) may also be present in form of one of their complexes with a cyclodextrin, for example α-cyclodextrin, β-cyclodextrin, γ-cyclodextrin, 2-hydroxypropyl-β-cyclodextrin or methyl-β-cyclodextrin.

Component (a) and Component (b) may also be formulated in the form of microcapsules, optionally with one or more carriers or vehicles or additives.

For oral administration, Component (a) and Component (b), together or separately, are formulated by mixing the active ingredient with conventional pharmaceutical acceptable carriers or vehicles enabling said active ingredients to be formulated in tablets, dragees, orally disintegrating tablets, capsules, liquid solutions or suspensions, syrups and the like.

The composition according to the present invention may be in form of a capsule containing two tablets as described herein above, one of them comprising Component (a) and the other comprising Component (b).

The (a/b) fixed-dose combination may also be formulated in tablets in which one or both of the two components is in controlled-release form, for example as a dispersion of said component in hydroxypropyl-methyl-cellulose or in a film-coated microgranule.

For example, memantine, preferably memantine hydrochloride in an ER-formulation and in an amount of 7 mg or 28 mg, is in the core, and aprepitant, in IR-formulation and in an amount of from 40 mg, is in the outer layer in a bilayer tablet in which, both the core and the outer layer may be coated with a film.

In said fixed dose combination, the retardant material of said first layer and the immediate release carrier second layer are two elements selected in order to allow respectively an extended (or sustained) release delivery of the memantine pharmaceutically acceptable salts, normally the hydrochloride, and to provide the solifenacin pharmaceutically acceptable salt, normally the succinate, in admixture with a pharmaceutical carrier for immediate release, for example according to the technologies described in U.S. Pat. No. 7,303,761 or in U.S. Pat. No. 8,802,143, the disclosures of which are incorporated herein in their entirety by reference.

Carriers or vehicles and vehicles for ER tablets include retardant materials such as is acrylic and methacrylic acid polymers and copolymers; cellulose derivatives such as hydroxypropylmethylcellulose, hydroxyethylcellulose, hydroxypropylethylcellulose, hydroxypropylcellulose, methylcellulose, ethylcellulose, or sodium carboxymethylcellulose; gums; waxes; glycerides or aliphatic alcohols or a mixture thereof.

The memantine/naAEA fixed-dose combination according to the present invention may be also formulated in a bi-layer tablet, the first layer containing for example memantine hydrochloride in an amount of 10 mg in admixture with a pharmaceutical carrier in IR-formulation and the second one containing ondansetron hydrochloride dihydrate, in an amount, in ondansetron, of 8 mg, in admixture with a pharmaceutical carrier in IR formulation. A third layer, free of active substances, consisting of a pharmaceutical carrier could be inserted between said first and said second layer.

An advantageous composition according to this embodiment consists of

Layer A, comprising from 5 mg to 10 mg of memantine hydrochloride Component (a) in admixture with a pharmaceutical carrier or vehicle in a IR formulation; and Layer B, comprising ondansetron hydrochloride dihydrate Component (b) in an amount (in ondansetron) of from 4 mg to 12 mg, in admixture with a pharmaceutical carrier or vehicle in an IR-formulation, said composition being destined to be administered twice per day, for example in combination with a pharmaceutical composition comprising solifenacin succinate Component (b) in an amount of from 10 mg to 30 mg, in admixture with a pharmaceutical carrier; and with a pharmaceutical composition comprising donepezil hydrochloride Component (c) in an amount of from 20 mg to 92 mg, in admixture with a pharmaceutical carrier or vehicle, both destined to be administered once per day.

According to another embodiment, the invention provides the herein above illustrated memantine/naAEA combination comprising (e) memantine or a pharmaceutically acceptable salt thereof; and
(b) a naAEA, for use for treating a patient suffering from Alzheimer type dementia in further combination with (c) donepezil or a pharmaceutically acceptable salt thereof in an amount that is equivalent to from 10 mg to 92 mg, preferably from 20 mg to 92 mg, normally from 10 mg to 70 mg, preferably from 20 mg to 70 mg of donepezil hydrochloride, as a single dose; and (d) solifenacin or a pharmaceutically acceptable salt thereof.

In particular, according to this embodiment, the invention provides a pharmaceutical combination essentially consisting of (a) a pharmaceutical composition in dosage unit form comprising memantine or a pharmaceutically acceptable salt thereof, in an amount that is equivalent to from 5 mg to 30 mg of memantine hydrochloride, in admixture with a pharmaceutical carrier or vehicle; and (b) a pharmaceutical composition in dosage unit form comprising a naAEA in admixture with a pharmaceutical carrier or vehicle, for use for the treatment of a patient suffering from Alzheimer type dementia in further combination with (c) a pharmaceutical composition in dosage unit form comprising donepezil or a pharmaceutically acceptable salt thereof in an amount that is equivalent to from 20 mg to 161 mg preferably from 20 mg to 92 mg, or from 25 mg to 92 mg, normally from 20 mg to 70 mg or from 25 mg to 70 mg of donepezil hydrochloride, in admixture with a pharmaceutical carrier or vehicle; and (d) a pharmaceutical composition in dosage unit form comprising solifenacin or a pharmaceutically acceptable salt thereof in an amount that is equivalent to from 10 mg to 30 mg of solifenacin succinate, in admixture with a pharmaceutical carrier or vehicle.

Normally, the naAEA active ingredient of Component (b) is selected from the group consisting of (b1) 5HT3-antagonists; (b2) DA-antagonists; (b3) H1-antagonists; (b4) cannabinoids; (b5) NK1-antagonists.

Among the above (b1)-(b5) naAEAs, a naAEA selected from the group consisting of alosetron and pharmaceutically acceptable salts and solvates thereof, in particular the hydrochloride, in an amount (in alosetron) of from 0.25 mg to 6 mg; azasetron and pharmaceutically acceptable salts and solvates thereof, in particular the hydrochloride, in an amount (in azasetron) of from 5 mg to 60 mg; dolasetron and pharmaceutically acceptable salts and solvates thereof, in particular the mesylate, in an amount (in dolasetron) of from 25 mg to 600 mg; granisetron and pharmaceutically acceptable salts and solvates thereof, in particular the hydrochloride, in an amount (in granisetron) of from 0.5 mg to 6 mg; ondansetron and pharmaceutically acceptable salts and solvates thereof, in particular the hydrochloride dihydrate, in an amount (in ondansetron) of from 2 mg to 64 mg; palonosetron and pharmaceutically acceptable salts and solvated thereof, in particular its hydrochloride, in an amount (in palonosetron) of from 0.25 mg to 3 mg; ramosetron and pharmaceutically acceptable salts and solvates thereof, in particular its hydrochloride, in an amount (in ramosetron) of from 0.0125 mg to 0.3 mg; tropisetron and pharmaceutically acceptable salts and solvates thereof, in particular the hydrochloride, in an amount of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine and pharmaceutically acceptable salts and solvates thereof, in particular the hydrochloride, in an amount (in chlorpromazine) of from 12.5 mg to 600 mg; prochlorperazine and pharmaceutically acceptable salts and solvates thereof, in particular the dimaleate, in an amount (in prochlorperazine) of from 2.5 mg to 30 mg; metoclopramide and pharmaceutically acceptable salts and solvates thereof, in particular the monohydrochloride monohydrate, in an amount (in metoclopramide) of from 5 mg to 60 mg; bromopride and pharmaceutically acceptable salts and solvates, in particular the monohydrochloride and the dihydrochloride monohydrate, in an amount (in bromopride) of from 5 mg to 60 mg; clebopride and pharmaceutically acceptable salts and solvates thereof, in particular the hydrogen malate and the hydrochloride monohydrate, in an amount (in clebopride) of from 0.25 mg to 3 mg; levosulpiride, in an amount of from 12.5 mg to 600 mg; alizapride and pharmaceutically acceptable salts thereof, in particular the hydrochloride, in an amount (in alizapride) of from 25 mg to 300 mg; trimethobenzamide and pharmaceutically acceptable salts thereof such as the monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine and pharmaceutically acceptable salts and solvates thereof, in particular the hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg is particularly advantageous.

According to a preferred embodiment, memantine or a pharmaceutically acceptable salt thereof and the naAEA are in a fixed-dose combination as illustrated herein above, Said fixed-dose (a/b) combination essentially consists of a pharmaceutical composition, preferably in dosage unit form, comprising said memantine or pharmaceutically acceptable salt thereof, in an amount that is equivalent to from 5 mg to 30 mg; and said naAEA is selected from the group consisting of (b1) 5HT3-antagonists; (b2) DA-antagonists; (b3) H1-antagonists; (b4) cannabinoids; (b5) NK1-antagonists.

Among the above (b1)-(b5) naAEA, a naAEA selected from the group consisting of alosetron and pharmaceutically acceptable salts and solvates thereof, in particular the hydrochloride, in an amount (in alosetron) of from 0.25 mg to 6 mg; azasetron and pharmaceutically acceptable salts and solvates thereof, in particular the hydrochloride, in an amount (in azasetron) of from 5 mg to 60 mg; dolasetron and pharmaceutically acceptable salts and solvates thereof, in particular the mesylate, in an amount (in dolasetron) of from 25 mg to 600 mg; granisetron and pharmaceutically acceptable salts and solvates thereof, in particular the hydrochloride, in an amount (in granisetron) of from 0.5 mg to 6 mg; ondansetron and pharmaceutically acceptable salts and solvates thereof, in particular the hydrochloride dihydrate, in an amount (in ondansetron) of from 2 mg to 64 mg; palonosetron and pharmaceutically acceptable salts and solvated thereof, in particular its hydrochloride, in an amount (in palonosetron) of from 0.25 mg to 3 mg; ramosetron and pharmaceutically acceptable salts and solvates thereof, in particular its hydrochloride, in an amount (in ramosetron) of from 0.0125 mg to 0.3 mg; tropisetron and pharmaceutically acceptable salts and solvates thereof, in particular the hydrochloride, in an amount of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine and pharmaceutically acceptable salts and solvates thereof, in particular the hydrochloride, in an amount (in chlorpromazine) of from 12.5 mg to 600 mg; prochlorperazine and pharmaceutically acceptable salts and solvates thereof, in particular the dimaleate, in an amount (in prochlorperazine) of from 2.5 mg to 30 mg; metoclopramide and pharmaceutically acceptable salts and solvates thereof, in particular the monohydrochloride monohydrate, in an amount (in metoclopramide) of from 5 mg to 60 mg; bromopride and pharmaceutically acceptable salts and solvates, in particular the monohydrochloride and the dihydrochloride monohydrate, in an amount (in bromopride) of from 5 mg to 60 mg; clebopride and pharmaceutically acceptable salts and solvates thereof, in particular the hydrogen malate and the hydrochloride monohydrate, in an amount (in clebopride) of from 0.25 mg to 3 mg; levosulpiride, in an amount of from 12.5 mg to 600 mg; alizapride and pharmaceutically acceptable salts thereof, in particular the hydrochloride, in an amount (in alizapride) of from 25 mg to 300 mg; trimethobenzamide and pharmaceutically acceptable salts thereof such as the monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine and pharmaceutically acceptable salts and solvates thereof, in particular the hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg.

This fixed-dose combination is destined to the treatment of a patient suffering from Alzheimer type dementia in further combination with donepezil Component (c) and solifenacin Component (d).

Preferably, donepezil hydrochloride and solifenacin succinate are formulated in a new composition comprising said active ingredients in admixture with a pharmaceutical carrier. Thus, the invention also provides a solifenacin/donepezil fixed-dose combination consisting of a pharmaceutical composition in dosage unit form, comprising from 10 mg to 30 mg, preferably 15 mg, of solifenacin succinate and from 10 mg to 92 mg, normally from 10 mg to 70 mg, preferably from 20 mg to 70 mg, of donepezil hydrochloride, in admixture with a pharmaceutical carrier or vehicle Specific donepezil/solifenacin compositions comprise 15 mg of solifenacin succinate and donepezil hydrochloride in an amount of from 10 mg to 50 mg, preferably of 10 mg, 15 mg, 20 mg, 25 mg, 30 mg 35 mg or 40 mg wherein said solifenacin succinate and donepezil hydrochloride do not interact each other.

In particular the pharmaceutical carrier comprises a diluent such as talc, powdered cellulose, lactose; a disaggregating agents such as microcrystalline cellulose, crospovidone or a starch, for example maize or corn starch; a lubricant such as magnesium or calcium stearate; and a binder, such as methyl cellulose, ethyl cellulose or hydroxypropyl methyl cellulose.

Preferably, the pharmaceutical unit form comprising the preferred composition according to the present invention is a coated tablet containing donepezil hydrochloride, in an amount of from 10 mg to 50 mg, preferably from 10 mg to 40 mg, and solifenacin succinate, in an amount of 15 mg, as active ingredients, in the core, in admixture with a pharmaceutical carrier as defined above.

In particular, in the solifenacin/donepezil fixed dose combination essentially consists of solifenacin succinate, in an amount of from 5.5% to 6.5%, donepezil hydrochloride, in an amount of from 4% to 20%; a diluent, in a amount of from 60% to 80%, a disaggregating agent, in a amount of from 6.8% to 7.5%; and a binder, in an amount of from 1.9% to 2.5% the total weight of the core. The coating normally is a non-enteric, fast-dissolving layer that covers the core according to known technologies. Normally, it is constituted by a cellulose derivative such as methyl hydroxyethyl cellulose or hydroxypropyl methyl cellulose, a glycerol ester such as diacetin or triacetin and a pigment such as titanium dioxide.

The Kits

The present invention also provides a kit or package containing a combination as described herein, accompanied by instructions for use. In particular, a kit of the present invention is a kit comprising a combination of medicaments for the treatment of Alzheimer type dementia.

According to the present invention the kit allows for the maximal functional capacity and safety during the treatment of a patient with a combination wherein the components may be administered concurrently or sequentially.

Memantine Component (a), the naAEA Component (b), donepezil Component (c) and solifenacin Component (d) may be present in the kit all in IR form or Component (a) is in ER form and the Components (b), (c) and (d) are each in IR form, each in admixture with a pharmaceutical carrier in a pharmaceutical composition formulated as illustrated herein above, according to known technologies.

Memantine Component (a), solifenacin Component (b) and donepezil Component (c) may be present in the kit all in IR form or Component (a) is in ER form and at the Components (b) and (c) are each in IR form, each in admixture with a pharmaceutical carrier in a pharmaceutical composition formulated as illustrated herein above, according to known technologies.

The pharmaceutical compositions may be packaged in any manner suitable for administration to a patient suffering from a hypocholinergic disorder of the CNS such as Alzheimer type dementia, Lewy body disease dementia or Parkinson's disease dementia, and the packaging is manufactured according to known technologies and completed with instructions for use clearly showing to the patient or to the caregiver how to take each of the units forms to be administered.

More particularly, according to a first embodiment, the kit of the present invention comprises
(a) a pharmaceutical composition in ER dosage unit form comprising or consisting essentially of a therapeutically effective amount of memantine or a pharmaceutically acceptable salt thereof, preferably its hydrochloride, in admixture with a pharmaceutical carrier or vehicle;
(b) a pharmaceutical composition in dosage unit form comprising or consisting essentially of a therapeutically effective amount of a naAEA, in admixture with a pharmaceutical carrier or vehicle;
(c) a pharmaceutical composition in IR dosage unit form comprising or consisting essentially of a therapeutically effective amount of donepezil or a pharmaceutically acceptable salt thereof, in admixture with a pharmaceutical carrier or vehicle; and
(d) a pharmaceutical composition in IR dosage unit form comprising or consisting essentially of a therapeutically effective amount of solifenacin or a pharmaceutically acceptable salt thereof, in admixture with a pharmaceutical carrier or vehicle,
for concurrent, sequential or separate administration.

More particularly, according to a further first embodiment, the kit of the present invention comprises
(a) a pharmaceutical composition in ER dosage unit form comprising or consisting essentially of a therapeutically effective amount of memantine or a pharmaceutically acceptable salt thereof, preferably its hydrochloride, in admixture with a pharmaceutical carrier or vehicle;
(b) a pharmaceutical composition in IR dosage unit form comprising or consisting essentially of a therapeutically effective amount of solifenacin or a pharmaceutically acceptable salt thereof, in admixture with a pharmaceutical carrier or vehicle; and
(c) a pharmaceutical composition in IR dosage unit form comprising or consisting essentially of a therapeutically effective amount of donepezil or a pharmaceutically acceptable salt thereof, in admixture with a pharmaceutical carrier or vehicle,
for concurrent, sequential or separate administration.

According to a second embodiment, the invention provides a kit comprising
(a) a pharmaceutical composition in dosage unit form comprising or consisting essentially of memantine or a pharmaceutically acceptable salt thereof, preferably its hydrochloride, in admixture with a pharmaceutical carrier or vehicle in an IR or ER form;
(b) a naAEA; and
(c/d) a fixed-dose combination that is a pharmaceutical composition comprising or consisting essentially of
(c) donepezil or a pharmaceutically acceptable salt, preferably its hydrochloride, in IR-form; and
(d) solifenacin or a pharmaceutically acceptable salt, preferably its succinate,
in admixture with a pharmaceutical carrier or vehicle.

For example, a kit according to this second embodiment may comprise:
(a) a pharmaceutical composition in dosage unit form comprising or consisting essentially of a memantine pharmaceutically acceptable salt, preferably the hydrochloride in an amount of from 7 mg to 28 mg in admixture with a pharmaceutical carrier or vehicle in an IR or ER form, in admixture with a pharmaceutical carrier or vehicle;
(b) a pharmaceutical composition comprising a naAEA selected from the group consisting of alosetron and pharmaceutically acceptable salts and solvates thereof, in particular the hydrochloride, in an amount (in alosetron) of from 0.25 mg to 6 mg; azasetron and pharmaceutically acceptable salts and solvates thereof, in particular the hydrochloride, in an amount (in azasetron) of from 5 mg to 60 mg; dolasetron and pharmaceutically acceptable salts and solvates thereof, in particular the mesylate, in an amount (in dolasetron) of from 25 mg to 600 mg; granisetron and pharmaceutically acceptable salts and solvates thereof, in particular the hydrochloride, in an amount (in granisetron) of from 0.5 mg to 6 mg; ondansetron and pharmaceutically acceptable salts and solvates thereof, in particular the hydrochloride dihydrate, in an amount (in ondansetron) of from 2 mg to 64 mg; palonosetron and pharmaceutically acceptable salts and solvated thereof, in particular its hydrochloride, in an amount (in palonosetron) of from 0.25 mg to 3 mg; ramosetron and pharmaceutically acceptable salts and solvates thereof, in particular its hydrochloride, in an amount (in ramosetron) of from 0.0125 mg to 0.3 mg; tropisetron and pharmaceutically acceptable salts and solvates thereof, in particular the hydrochloride, in an amount of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine and pharmaceutically acceptable salts and solvates thereof, in particular the hydrochloride, in an amount (in chlorpromazine) of from 12.5 mg to 600 mg; prochlorperazine and pharmaceutically acceptable salts and solvates thereof, in particular the dimaleate, in an amount (in prochlorperazine) of from 2.5 mg to 30 mg; metoclopramide and pharmaceutically acceptable salts and solvates thereof, in particular the monohydrochloride monohydrate, in an amount (in metoclopramide) of from 5 mg to 60 mg; bromopride and pharmaceutically acceptable salts and solvates, in particular the monohydrochloride and the dihydrochloride monohydrate, in an amount (in bromopride) of from 5 mg to 60 mg; clebopride and pharmaceutically acceptable salts and solvates thereof, in particular the hydrogen malate and the hydrochloride monohydrate, in an amount (in clebopride) of from 0.25 mg to 3 mg; levosulpiride, in an amount of from 12.5 mg to 600 mg; alizapride and pharmaceutically acceptable salts thereof, in particular the hydrochloride, in an amount (in alizapride) of from 25 mg to 300 mg; trimethobenzamide and pharmaceutically acceptable salts thereof such as the monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine and pharmaceutically acceptable salts and solvates thereof, in particular the hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg,
in admixture with a pharmaceutical carrier or vehicle; and
(c/d) a fixed-dose combination that is a pharmaceutical composition comprising or consisting essentially of
(c) donepezil hydrochloride in an amount of from 10 mg to 92 mg, preferably from 20 mg to 92 mg, normally from 10 mg to 70 mg, preferably from 20 mg to 70 mg; and
(d) solifenacin succinate in an amount of from 10 mg to 30 mg, advantageously from 15 mg to 25 mg, preferably of 15 mg;
in admixture with a pharmaceutical carrier or vehicle in an IR form.

According to a further second embodiment, the invention provides a kit comprising
(a) a pharmaceutical composition in dosage unit form comprising or consisting essentially of memantine or a pharmaceutically acceptable salt thereof, preferably its hydrochloride, in admixture with a pharmaceutical carrier or vehicle in an IR or ER form; and
(b/c) a fixed-dose combination that is a pharmaceutical composition comprising or consisting essentially of
(b) solifenacin or a pharmaceutically acceptable salt, preferably its succinate; and
(c) donepezil or a pharmaceutically acceptable salt, preferably its hydrochloride,
in admixture with a pharmaceutical carrier or vehicle, in IR-form.

This kit has the advantage of allowing an improvement in the treatment of a patient suffering from Alzheimer type dementia. In fact, in the case of the prescription of IR-memantine that must be taken two times/day, the kit of the present invention allows the administration of a composition (b/c) comprising solifenacin and donepezil that are administered once a day, thus rendering the treatment easier for the patient or for the caregiver.

For example, a kit according to this second embodiment may comprise:
(a) a pharmaceutical composition in dosage unit form comprising or consisting essentially of a memantine pharmaceutically acceptable salt, preferably the hydrochloride in an amount of from 7 mg to 28 mg in admixture with a pharmaceutical carrier or vehicle in an IR or ER form,
in admixture with a pharmaceutical carrier or vehicle; and
(b/c) a fixed-dose combination that is a pharmaceutical composition comprising or consisting essentially of
(b) a solifenacin pharmaceutically acceptable salt, preferably the succinate thereof in an amount of from 10 mg to 30 mg, advantageously from 15 mg to 25 mg, preferably of 15 mg; and
(c) a donepezil pharmaceutically acceptable salt, preferably the hydrochloride thereof in an amount of from 10 mg to 92 mg, preferably from 20 mg to 92 mg, normally from 10 mg to 70 mg, preferably from 20 mg to 70 mg;
in admixture with a pharmaceutical carrier or vehicle in an IR form.

An advantageous kit of this second embodiment comprises:
(a) a pharmaceutical composition in dosage unit form comprising or consisting essentially of memantine hydrochloride, in an amount of from 7 mg to 28 mg in admixture with a pharmaceutical carrier or vehicle in ER form
in admixture with a pharmaceutical carrier; and
(b/c) a fixed-dose combination that is a pharmaceutical composition comprising or consisting essentially of
(b) solifenacin succinate, in an amount of from 15 mg to 30 mg; and
(c) donepezil hydrochloride, in an amount of from 40 mg to 92 mg, normally from 40 mg to 70 mg,
in admixture with a pharmaceutical carrier or vehicle, in IR-form.

Another advantageous kit of this second embodiment comprises:
(a) a pharmaceutical composition in dosage unit form comprising or consisting essentially of memantine hydrochloride, in an amount of from 7 mg to 28 mg in admixture with a pharmaceutical carrier or vehicle in ER form
in admixture with a pharmaceutical carrier;
(b) a pharmaceutical composition in dosage unit form comprising a naAEA selected from the group consisting of alosetron hydrochloride, in an amount (in alosetron) of from 0.25 mg to 6 mg; azasetron hydrochloride, in an amount (in azasetron) of from 5 mg to 60 mg; dolasetron mesylate, in an amount (in dolasetron) of from 25 mg to 600 mg; granisetron hydrochloride, in an amount (in granisetron) of from 0.5 mg to 6 mg; ondansetron hydrochloride dihydrate, in an amount (in ondansetron) of from 2 mg to 64 mg; palonosetron hydrochloride, in an amount (in palonosetron) of from 0.25 mg to 3 mg; ramosetron hydrochloride, in an amount (in ramosetron) of from 0.0125 mg to 0.3 mg; tropisetron hydrochloride, in an amount of from 2.5 mg to 30 mg; domperidone, in an amount of from 5 mg to 60 mg; haloperidol, in an amount of from 0.5 mg to 60 mg; chlorpromazine hydrochloride, in an amount (in chlorpromazine) of from 12.5 mg to 600 mg; prochlorperazine dimaleate, in an amount (in prochlorperazine) of from 2.5 mg to 30 mg; metoclopramide monohydrochloride monohydrate, in an amount (in metoclopramide) of from 5 mg to 60 mg; bromopride monohydrochloride or bromopride dihydrochloride monohydrate, in an amount (in bromopride) of from 5 mg to 60 mg; clebopride hydrogen malate or clebopride hydrochloride monohydrate, in an amount (in clebopride) of from 0.25 mg to 3 mg; levosulpiride, in an amount of from 12.5 mg to 600 mg; alizapride hydrochloride, in an amount (in alizapride) of from 25 mg to 300 mg; trimethobenzamide monohydrochloride, in an amount (in trimethobenzamide) of from 50 mg to 600 mg; in an amount of from 6.25 mg to 300 mg; promethazine hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg, in admixture with a pharmaceutical carrier or vehicle; and (c/d) a fixed-dose combination that is a pharmaceutical composition comprising or consisting essentially of (c) donepezil hydrochloride, in an amount of from 10 mg to 50 mg, normally from 10 mg to 40 mg; and (d) solifenacin succinate, in an amount of from 15 mg to 30 mg, in admixture with a pharmaceutical carrier or vehicle, in IR-form.

An advantageous kit of this second embodiment comprises a pharmaceutical combination essentially consisting of:

(a) a pharmaceutical composition in dosage unit form comprising or consisting essentially of memantine hydrochloride, in an amount of from 7 mg to 28 mg in admixture with a pharmaceutical carrier or vehicle in ER form in admixture with a pharmaceutical carrier; and (b/c) a fixed-dose combination that is a pharmaceutical composition comprising or consisting essentially of (b) solifenacin succinate, in an amount of 15 mg; and (c) donepezil hydrochloride, in an amount of from 10 mg to 50 mg, normally from 10 mg to 40 mg, in admixture with a pharmaceutical carrier or vehicle, in IR-form.

This kit may contain the combination disclosed as the third embodiment of the above "The Combinations" section.

According to a third embodiment, the invention provides a kit comprising (a/b) a novel fixed-dose combination that is a pharmaceutical composition in dosage unit form comprising or consisting essentially of (a) memantine or a pharmaceutically acceptable salt thereof; and (b) solifenacin or a pharmaceutically acceptable salt thereof, in admixture with a pharmaceutical carrier or vehicle; and (c) a pharmaceutical composition in dosage unit form comprising or consisting essentially of a nsPAChA in admixture with a pharmaceutical carrier.

According to a third embodiment, the invention provides a kit comprising:

(a/d) a fixed-dose combination that is a pharmaceutical composition comprising or consisting essentially of (a) memantine or a pharmaceutically acceptable salt thereof, in an amount that is equivalent to from 5 mg to 30 mg of memantine hydrochloride, said salt being preferably the hydrochloride; and (d) solifenacin or a pharmaceutically acceptable salt thereof, in an amount that is equivalent to from 10 mg to 30 mg of solifenacin succinate, said salt being preferably the succinate;

in admixture with a pharmaceutical carrier or vehicle;

(b) a pharmaceutical composition in comprising a naAEA selected from the group consisting of alosetron and pharmaceutically acceptable salts and solvates thereof, in particular the hydrochloride, in an amount (in alosetron) of from 0.25 mg to 6 mg; azasetron and pharmaceutically acceptable salts and solvates thereof, in particular the hydrochloride, in an amount (in azasetron) of from 5 mg to 60 mg; dolasetron and pharmaceutically acceptable salts and solvates thereof, in particular the mesylate, in an amount (in dolasetron) of from 25 mg to 600 mg; granisetron and pharmaceutically acceptable salts and solvates thereof, in particular the hydrochloride, in an amount (in granisetron) of from 0.5 mg to 6 mg; ondansetron and pharmaceutically acceptable salts and solvates thereof, in particular the hydrochloride dihydrate, in an amount (in ondansetron) of from 2 mg to 64 mg; palonosetron and pharmaceutically acceptable salts and solvated thereof, in particular its hydrochloride, in an amount (in palonosetron) of from 0.25 mg to 3 mg; ramosetron and pharmaceutically acceptable salts and solvates thereof, in particular its hydrochloride, in an amount (in ramosetron) of from 0.0125 mg to 0.3 mg; tropisetron and pharmaceutically acceptable salts and solvates thereof, in particular the hydrochloride, in an amount of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine and pharmaceutically acceptable salts and solvates thereof, in particular the hydrochloride, in an amount (in chlorpromazine) of from 12.5 mg to 600 mg; prochlorperazine and pharmaceutically acceptable salts and solvates thereof, in particular the dimaleate, in an amount (in prochlorperazine) of from 2.5 mg to 30 mg; metoclopramide and pharmaceutically acceptable salts and solvates thereof, in particular the monohydrochloride monohydrate, in an amount (in metoclopramide) of from 5 mg to 60 mg; bromopride and pharmaceutically acceptable salts and solvates, in particular the monohydrochloride and the dihydrochloride monohydrate, in an amount (in bromopride) of from 5 mg to 60 mg; clebopride and pharmaceutically acceptable salts and solvates thereof, in particular the hydrogen malate and the hydrochloride monohydrate, in an amount (in clebopride) of from 0.25 mg to 3 mg; levosulpiride, in an amount of from 12.5 mg to 600 mg; alizapride and pharmaceutically acceptable salts thereof, in particular the hydrochloride, in an amount (in alizapride) of from 25 mg to 300 mg; trimethobenzamide and pharmaceutically acceptable salts thereof such as the monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine and pharmaceutically acceptable salts and solvates thereof, in particular the hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg, in admixture with a pharmaceutical carrier or vehicle; and (c) a pharmaceutical composition in dosage unit form comprising or consisting essentially of donepezil or a pharmaceutically acceptable salt thereof, in an amount that is equivalent to from 10 mg to 92 mg, preferably from 20 mg to 92 mg, normally from 10 mg to 70 mg, preferably from 20 mg to 70 mg of donepezil hydrochloride, said salt being preferably the hydrochloride, in admixture with a pharmaceutical carrier or vehicle, in IR-form.

An advantageous kit according to this third embodiment provides a kit comprising:

(a/b) a fixed-dose combination that is a novel pharmaceutical composition comprising or consisting essentially of
  (a) memantine or a pharmaceutically acceptable salt thereof, in an amount that is equivalent to from 5 mg to 30 mg of memantine hydrochloride, said salt being preferably the hydrochloride; and
  (b) solifenacin or a pharmaceutically acceptable salt thereof, in an amount that is equivalent to from 10 mg to 30 mg of solifenacin succinate, said salt being preferably the succinate;

in admixture with a pharmaceutical carrier or vehicle; and (c) a pharmaceutical composition in dosage unit form comprising or consisting essentially of donepezil or a pharmaceutically acceptable salt thereof, in an amount that is equivalent to from 20 mg to 92 mg of donepezil hydrochloride, said salt being preferably the hydrochloride, in admixture with a pharmaceutical carrier or vehicle, in IR-form.

In a preferred kit according to this third embodiment, the Component (a/b) comprises memantine hydrochloride, in an amount of from 7 mg to 28 mg and solifenacin succinate, in an amount of from 15 mg to 30 mg; and The Component (c) comprises donepezil hydrochloride in an amount of from 40 mg to 92 mg, normally from 40 mg to 70 mg.

The fixed-dose combination (a/b) is exhaustively illustrated herein above.

In a preferred kit according to this third embodiment, the pharmaceutical composition Component (a/d) comprises memantine hydrochloride, in an amount of from 7 mg to 28 mg and solifenacin succinate, in an amount of 15 mg to 30 mg preferably of 15 mg; the pharmaceutical composition Component (b) comprises a naAEA selected from the group consisting of ondansetron hydrochloride dihydrate, in an amount (in ondansetron) of from 4 mg to 32 mg, domperidone, in an amount of from 10 mg to 30 mg; metoclopramide monohydrochloride monohydrate, in an amount of from 10 mg to 30 mg and aprepitant, in an amount of 40 mg; and the pharmaceutical composition Component (c) comprises donepezil hydrochloride in an amount of from 10 mg to 70 mg or from 40 mg to 70 mg. In said compositions, the active ingredients are in admixture with a pharmaceutical carrier or vehicle.

An advantageous kit according to this third embodiment provides a kit comprising:

(a/b) a fixed-dose combination that is a novel pharmaceutical composition comprising or consisting essentially of
  (a) memantine or a pharmaceutically acceptable salt thereof, in an amount that is equivalent to from 5 mg to 30 mg of memantine hydrochloride, said salt being preferably the hydrochloride; and
  (b) solifenacin or a pharmaceutically acceptable salt thereof, in an amount that is equivalent to from 10 mg to 30 mg, advantageously from 15 mg to 25 mg, of solifenacin succinate, said salt being preferably the succinate;

in admixture with a pharmaceutical carrier or vehicle; and (c) a pharmaceutical composition in dosage unit form comprising or consisting essentially of donepezil or a pharmaceutically acceptable salt thereof, in an amount that is equivalent to from 10 mg to 92 mg, advantageously from 20 mg to 92 mg of donepezil hydrochloride, said salt being preferably the hydrochloride, in admixture with a pharmaceutical carrier or vehicle, in IR-form.

In a preferred kit according to this third embodiment, the pharmaceutical composition Component (a/b) comprises memantine hydrochloride, in an amount of from 7 mg to 28 mg and solifenacin succinate, in an amount of from 15 mg to 30 mg, preferably of 15 mg; and the pharmaceutical composition Component (c) comprises donepezil hydrochloride in an amount of from 10 mg to 92 mg, preferably from 20 mg to 92 mg, normally from 10 mg to 70 mg, preferably from 20 mg to 70 mg or from 40 mg to 70 mg. In said compositions, the active ingredients are in admixture with a pharmaceutical carrier or vehicle.

The fixed-dose combination (a/b) is exhaustively illustrated herein above.

According to a fourth embodiment, the invention provides a kit comprising (a/c) a fixed-dose combination that is a pharmaceutical composition comprising or consisting essentially of
  (a) memantine or a pharmaceutically acceptable salt thereof; and
  (c) donepezil or a pharmaceutically acceptable salt thereof, in admixture with a pharmaceutical carrier or vehicle; and (b) a pharmaceutical composition in dosage unit form comprising or consisting essentially of solifenacin or a pharmaceutically acceptable salt thereof in admixture with a pharmaceutical carrier.

According to a fourth embodiment, the invention provides a kit comprising (a/c) a fixed-dose combination that is a pharmaceutical composition comprising or consisting essentially of
  (a) memantine or a pharmaceutically acceptable salt thereof; and
  (c) donepezil or a pharmaceutically acceptable salt thereof, in admixture with a pharmaceutical carrier or vehicle; and (b) a pharmaceutical composition in comprising a naAEA selected from the group consisting of alosetron and pharmaceutically acceptable salts and solvates thereof, in particular the hydrochloride, in an amount (in alosetron) of from 0.25 mg to 6 mg; azasetron and pharmaceutically acceptable salts and solvates thereof, in particular the hydrochloride, in an amount (in azasetron) of from 5 mg to 60 mg; dolasetron and pharmaceutically acceptable salts and solvates thereof, in particular the mesylate, in an amount (in dolasetron) of from 25 mg to 600 mg; granisetron and pharmaceutically acceptable salts and solvates thereof, in particular the hydrochloride, in an amount (in granisetron) of from 0.5 mg to 6 mg; ondansetron and pharmaceutically acceptable salts and solvates thereof, in particular the hydrochloride dihydrate, in an amount (in ondansetron) of from 2 mg to 64 mg; palonosetron and pharmaceutically acceptable salts and solvated thereof, in particular its hydrochloride, in an amount (in palonosetron) of from 0.25 mg to 3 mg; ramosetron and pharmaceutically acceptable salts and solvates thereof, in particular its hydrochloride, in an amount (in ramosetron) of from 0.0125 mg to 0.3 mg; tropisetron and pharmaceutically acceptable salts and solvates thereof, in particular the hydrochloride, in an amount of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine and pharmaceutically acceptable salts and solvates thereof, in particular the hydrochloride, in an amount (in chlorpromazine) of from 12.5 mg to 600 mg; prochlorperazine and pharmaceutically acceptable salts and solvates thereof, in particular the dimaleate, in an amount (in prochlorperazine) of from 2.5 mg to 30 mg; metoclopramide and pharmaceutically acceptable salts and solvates thereof, in particular the monohydrochloride monohydrate, in an amount (in metoclopramide) of from 5 mg to 60 mg; bromopride and pharmaceutically acceptable salts and solvates, in particular the monohydrochloride and the dihydrochloride monohydrate, in an amount (in bromopride) of from 5 mg to 60 mg; clebopride and pharmaceutically acceptable salts and solvates thereof, in particular the hydrogen malate and the hydrochloride monohydrate, in an amount (in clebopride) of from 0.25 mg to 3 mg; levosulpiride, in an amount of from 12.5 mg to 600 mg; alizapride and pharmaceutically acceptable salts thereof, in particular the hydrochloride, in an amount (in alizapride) of from 25 mg to 300 mg; trimethobenzamide and pharmaceutically acceptable salts thereof such as the monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine and pharmaceutically acceptable salts and solvates thereof, in particular the hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg, in admixture with a pharmaceutical carrier or vehicle; and (d) a pharmaceutical composition in dosage unit form comprising or consisting essentially of solifenacin or a pharmaceutically acceptable salt thereof in admixture with a pharmaceutical carrier.

This fourth embodiment provides an advantageous kit comprising:

(a/c) a fixed-dose combination that is a pharmaceutical composition comprising or consisting essentially of (a/c) a novel fixed-dose combination that is a pharmaceutical composition comprising or consisting essentially of (a) a memantine or a pharmaceutically acceptable salt thereof, preferably the hydrochloride thereof in an amount of from 5 mg to 30 mg; and (c) donepezil or a pharmaceutically acceptable salt thereof, preferably the hydrochloride thereof in an amount of from 20 mg to 92 mg, in admixture with a pharmaceutical carrier or vehicle; and (b) a pharmaceutical composition in dosage unit form comprising or consisting essentially of solifenacin or a pharmaceutically acceptable salt thereof, preferably the succinate thereof in an amount of from 10 mg to 30 mg, in admixture with a pharmaceutical carrier or vehicle.

This fourth embodiment provides an advantageous kit comprising:

(a/c) a fixed-dose combination that is a pharmaceutical composition comprising or consisting essentially of (a) a memantine or a pharmaceutically acceptable salt thereof, preferably the hydrochloride thereof in an amount of from 5 mg to 30 mg; and (c) donepezil or a pharmaceutically acceptable salt thereof, preferably the hydrochloride thereof in an amount of from 10 mg to 92 mg, preferably from 20 mg to 92 mg, normally from 10 mg to 70 mg, preferably from 20 mg to 70 mg, in admixture with a pharmaceutical carrier or vehicle;

(b) a pharmaceutical composition in dosage unit form comprising or consisting essentially of a naAEA selected from the group consisting of alosetron and pharmaceutically acceptable salts and solvates thereof, in particular the hydrochloride, in an amount (in alosetron) of from 0.25 mg to 6 mg; azasetron and pharmaceutically acceptable salts and solvates thereof, in particular the hydrochloride, in an amount (in azasetron) of from 5 mg to 60 mg; dolasetron and pharmaceutically acceptable salts and solvates thereof, in particular the mesylate, in an amount (in dolasetron) of from 25 mg to 600 mg; granisetron and pharmaceutically acceptable salts and solvates thereof, in particular the hydrochloride, in an amount (in granisetron) of from 0.5 mg to 6 mg; ondansetron and pharmaceutically acceptable salts and solvates thereof, in particular the hydrochloride dihydrate, in an amount (in ondansetron) of from 2 mg to 64 mg; palonosetron and pharmaceutically acceptable salts and solvated thereof, in particular its hydrochloride, in an amount (in palonosetron) of from 0.25 mg to 3 mg; ramosetron and pharmaceutically acceptable salts and solvates thereof, in particular its hydrochloride, in an amount (in ramosetron) of from 0.0125 mg to 0.3 mg; tropisetron and pharmaceutically acceptable salts and solvates thereof, in particular the hydrochloride, in an amount of from 2.5 mg to 30 mg; domperidone and pharmaceutically acceptable salts and solvates thereof, in an amount (in domperidone) of from 5 mg to 60 mg; haloperidol, in an amount of from 0.5 mg to 60 mg; chlorpromazine and pharmaceutically acceptable salts and solvates thereof, in particular the hydrochloride, in an amount (in chlorpromazine) of from 12.5 mg to 600 mg; prochlorperazine and pharmaceutically acceptable salts and solvates thereof, in particular the dimaleate, in an amount (in prochlorperazine) of from 2.5 mg to 30 mg; metoclopramide and pharmaceutically acceptable salts and solvates thereof, in particular the monohydrochloride monohydrate, in an amount (in metoclopramide) of from 5 mg to 60 mg; bromopride and pharmaceutically acceptable salts and solvates, in particular the monohydrochloride and the dihydrochloride monohydrate, in an amount (in bromopride) of from 5 mg to 60 mg; clebopride and pharmaceutically acceptable salts and solvates thereof, in particular the hydrogen malate and the hydrochloride monohydrate, in an amount (in clebopride) of from 0.25 mg to 3 mg; levosulpiride, in an amount of from 12.5 mg to 600 mg; alizapride and pharmaceutically acceptable salts thereof, in particular the hydrochloride, in an amount (in alizapride) of from 25 mg to 300 mg; trimethobenzamide and pharmaceutically acceptable salts thereof such as the monohydrochloride, in an amount (in trimethobenzamide) of from 50 mg to 600 mg; meclizine (also called meclozine) and pharmaceutically acceptable salts and solvates thereof, in an amount (in meclizine) of from 6.25 mg to 300 mg; promethazine and pharmaceutically acceptable salts and solvates thereof, in particular the hydrochloride, in an amount (in promethazine) of from 12.5 mg to 150 mg; dronabinol in an amount of from 1.25 mg to 60 mg; nabilone, in an amount of from 0.5 mg to 6 mg; aprepitant, in an amount of from 20 mg to 750 mg; netupitant, in an amount of from 150 mg to 1800 mg; rolapitant, in an amount of from 30 mg to 360 mg; and casopitant, in an amount of from 25 mg to 300 mg, in admixture with a pharmaceutical carrier or vehicle; and (d) a pharmaceutical composition in dosage unit form comprising or consisting essentially of solifenacin or a pharmaceutically acceptable salt thereof, preferably the succinate thereof in an amount of from 10 mg to 30 mg, advantageously from 15 mg to 25 mg, preferably of 15 mg, in admixture with a pharmaceutical carrier or vehicle.

In a preferred kit according to this fourth embodiment, the pharmaceutical composition Component (a/c) comprises memantine hydrochloride, in an amount of from 7 mg to 28 mg; and donepezil hydrochloride, in an amount of from 10 mg to 70 mg, normally from 40 mg to 70 mg; the pharmaceutical composition Component (b) is a fixed dose combination consisting of a pharmaceutical composition comprising netupitant in an amount of 300 mg and palonosetron hydrochloride in an amount, in palonosetron of 0.5 mg; and the pharmaceutical composition Component (d) comprises solifenacin succinate, in an amount of from 10 mg to 30 mg, advantageously from 15 mg to 25 mg, preferably of 15 mg. in said pharmaceutical compositions, the active ingredient are in admixture with a pharmaceutical carrie or vehicle. In particular, Component (b) may be the brand palonosetron/netupitant fixed-dose combination known as Akynzeo®.

According to a fourth embodiment, the invention provides a kit comprising (a/c) a fixed-dose combination that is a pharmaceutical composition comprising or consisting essentially of
  (a) memantine or a pharmaceutically acceptable salt thereof; and
  (c) donepezil or a pharmaceutically acceptable salt thereof,
in admixture with a pharmaceutical carrier or vehicle; and (b) a pharmaceutical composition in dosage unit form comprising or consisting essentially of solifenacin or a pharmaceutically acceptable salt thereof in admixture with a pharmaceutical carrier.

This fourth embodiment provides an advantageous kit comprising:

(a/c) a fixed-dose combination that is a pharmaceutical composition comprising or consisting essentially of
(a) a memantine or a pharmaceutically acceptable salt thereof, preferably the hydrochloride thereof in an amount of from 5 mg to 30 mg; and
(c) donepezil or a pharmaceutically acceptable salt thereof, preferably the hydrochloride thereof in an amount of from 10 mg to 92 mg, preferably from 20 mg to 92 mg, normally from 10 mg to 70 mg, preferably from 20 mg to 70 mg, advantageously from 20 mg to 92 mg, in admixture with a pharmaceutical carrier or vehicle; and (b) a pharmaceutical composition in dosage unit form comprising or consisting essentially of solifenacin or a pharmaceutically acceptable salt thereof, preferably the succinate thereof in an amount of from 10 mg to 30 mg, advantageously from 15 mg to 25 mg, preferably of 15 mg, in admixture with a pharmaceutical carrier or vehicle.

In a preferred kit according to this fourth embodiment, the pharmaceutical composition Component (a/c) comprises memantine hydrochloride, in an amount of from 7 mg to 28 mg; and donepezil hydrochloride, in an amount of from 20 mg to 70 mg or from 40 mg to 70 mg; and the pharmaceutical composition Component (b) comprises solifenacin succinate, in an amount of from 15 mg to 25 mg.

In a preferred kit according to this embodiment, the Component (a/c) comprises memantine hydrochloride, in an amount of from 7 mg to 28 mg; and donepezil hydrochloride, in an amount of from 40 mg to 92 mg, normally from 40 mg to 70 mg; and the Component (b) is solifenacin succinate, in an amount of from 15 mg to 30 mg.

The aforementioned kits may help the physician, the relatives and the caregiver to render the supply of the medicaments to the patient more comfortable.

The pathologic conditions treated with the compositions and kits of the present invention include, but are not limited to, Alzheimer's disease, Parkinson's disease dementia, Lewy body dementia and other disorders of human cognitive and neurobehavioral function that are treated, in part, by pharmaceuticals intended to augment brain acetylcholine-mediated neurotransmission.

As set forth above, the fact that the combinations and kits of the present invention allow a better response to the memantine therapy of Alzheimer type dementia in respect to the response obtained with memantine alone, results from a surprising finding in a limited but indicative clinical investigation in patients with moderate dementia, among whom some ones were under treatment with memantine.

The above combined memantine/solifenacin/donepezil treatment involves greater and longer efficacy and less adverse effects by allowing the safe and tolerable administration of therapeutically effective, high-doses of donepezil. In particular, the treatment with donepezil according to the present invention is safe and effective, also in combination with other pharmaceuticals, in treating patients in need of an acetylcholine esterase inhibition, in particular dementias of the Alzheimer type on a normally once daily basis.

The presence of an antiemetic agent in the combinations of the present invention assures a safe administration of high and even very high doses of donepezil.

The Method

As indicated above, the present invention also proposes a method for the treatment of Alzheimer type dementia, which comprises treating a patient in need of said treatment with an effective amount of a N-methyl-D-aspartate receptor antagonist selected from the group consisting of memantine and pharmaceutical acceptable salts thereof [Component (a)], and with an effective amount of a non-selective peripheral anticholinergic agent selected from the group consisting of solifenacin and pharmaceutically acceptable salts thereof [Component (b)], in combination with a cholinesterase inhibitor selected from the group consisting of donepezil and pharmaceutically acceptable salts thereof [Component (c)]. Said donepezil or pharmaceutical acceptable salt is administered at a daily dose that is equivalent to from 10 mg to 92 mg, preferably from 20 mg to 92 mg, normally from 10 mg to 70 mg, preferably from 20 mg to 70 mg of donepezil hydrochloride. Thanks to the solifenacin/memantine synergism, said donepezil amount may advantageously be of from 20 mg to 70 mg or from 40 mg to 70 mg, as a single dose, with substantially improved therapeutic response.

In general, said Component (a) is memantine or a pharmaceutically acceptable salt thereof, at a daily dose that is equivalent to from 5 mg to 30 mg of memantine hydrochloride, and said Component (b) is solifenacin or a pharmaceutically acceptable salt thereof, at a daily dose that is equivalent to from 10 mg to 30 mg, advantageously from 15 mg to 25 mg, preferably of 15 mg of solifenacin succinate.

Advantageously, said Component (a) is memantine or a pharmaceutically acceptable salt thereof, in a pharmaceutical composition comprising said memantine or pharmaceutically acceptable salt thereof in an amount that is equivalent to from 5 mg to 30 mg of memantine hydrochloride, in admixture with a pharmaceutical carrier or vehicle; said Component (b) is solifenacin or a pharmaceutically acceptable salt thereof, in a pharmaceutical composition comprising said solifenacin or pharmaceutically acceptable salt thereof in an amount that is equivalent to from 10 mg to 30 mg, advantageously from 15 mg to 25 mg, preferably of 15 mg of solifenacin succinate; and said Component (c) is donepezil or a pharmaceutically acceptable salt thereof, in a pharmaceutical composition comprising said donepezil or pharmaceutically acceptable salt thereof in an amount that is equivalent to 10 mg to 92 mg, preferably from 20 mg to 92 mg, normally from 10 mg to 70 mg, preferably from 20 mg to 70 mg of donepezil hydrochloride. Due to the solifenacin/memantine synergism, said donepezil amount may advantageously be of from 40 mg to 70 mg.

According to an embodiment, said Component (a) is memantine hydrochloride, in a pharmaceutical composition comprising said memantine hydrochloride in an amount of from 7 mg to 28 mg, in admixture with a pharmaceutical carrier in an extended-release formulation; and said Component (b) is solifenacin succinate, in a pharmaceutical composition comprising said solifenacin succinate in an amount of from 10 mg to 30 mg, advantageously from 15 mg to 25 mg, preferably of 15 mg, in admixture with a pharmaceutical carrier or vehicle in an immediate-release formulation.

According to another embodiment, said Component (a) is memantine hydrochloride, in a pharmaceutical composition comprising said memantine hydrochloride in an amount of from 5 mg to 10 mg, in admixture with a pharmaceutical carrier in an immediate-release formulation; and said Component (b) is solifenacin succinate, in a pharmaceutical composition comprising said solifenacin succinate in an amount of from 10 mg to 30 mg, advantageously from 15 mg to 25 mg, preferably of 15 mg, in admixture with a pharmaceutical carrier or vehicle in an immediate-release formulation.

According to another embodiment, said Component (a) is memantine hydrochloride, in a pharmaceutical composition comprising said memantine hydrochloride in an amount of from 5 mg to 10 mg, in admixture with a pharmaceutical carrier in an immediate-release formulation; said Component (b) is solifenacin succinate, in a pharmaceutical composition comprising said solifenacin succinate in an amount of from 10 mg to 30 mg, advantageously from 15 mg to 25 mg, preferably of 15 mg, in admixture with a pharmaceutical carrier or vehicle in an immediate release formulation; and said Component (c) is donepezil hydrochloride, in a pharmaceutical composition comprising said donepezil hydrochloride, in an amount of from 10 mg to 70 mg, advantageously from 10 mg to 50 mg, preferably from 10 mg to 40 mg, in admixture with a pharmaceutical carrier or vehicle.

According to a preferred embodiment, the method of the present invention is carried out by using said Component (a) and said Component (b) in a fixed-dose combination consisting of a pharmaceutical composition comprising memantine or a pharmaceutically acceptable salt thereof [Component (a)], in an amount that is equivalent to from 5 mg to 30 mg, preferably from 7 mg to 28 mg, of memantine hydrochloride, and solifenacin or a pharmaceutically acceptable salt thereof [Component (b)], in an amount that is equivalent to from 5 mg to 30 mg, advantageously of from 15 mg to 25 mg, preferably of 15 mg, of solifenacin succinate, in admixture with a pharmaceutical carrier or vehicle.

As set forth above, the above method allows for a greater response to the memantine therapy of Alzheimer type dementia as compared to the response obtained with memantine alone. The method is based on a surprising finding in a limited but indicative clinical investigation in patients with moderate Alzheimer-type dementia, 58% of whom were treated with memantine.

The above combined memantine/solifenacin treatment involves greater and longer efficacy and less adverse effects by allowing the safe and tolerable administration of therapeutically effective, high-doses of donepezil. In particular, the treatment with donepezil according to the present invention is safe and effective, also in combination with other pharmaceuticals, in treating patients in need of an acetylcholine esterase inhibitor, in particular dementias of the Alzheimer type on a normally once daily basis.

The aforementioned kits may help the physician, the relatives and the caregiver to render the supply of the medicaments to the patient more comfortable.

The pathologic conditions treated with the compositions and kits of the present invention include, but are not limited to, Alzheimer's disease, Parkinson's disease dementia, Lewy body dementia and other disorders of human cognitive and neurobehavioral function that are treated, in part, by pharmaceuticals intended to augment brain acetylcholine-mediated neurotransmission.

The therapeutic efficacy is measured by the degree to which cognitive and other neurobehavioral disabilities associated with dementias of the Alzheimer type, as documented by the use of standard scales, are reduced.

The following examples illustrate the invention.

EXAMPLE 1

Patients with moderate Alzheimer's disease were enrolled in a clinical trial to examine the efficacy of high doses of donepezil (enabled by the concomitant administration of solifenacin) with or without memantine. The dose of solifenacin was fixed throughout the trial at 15 mg/day. The dose of donepezil was titrated up to 40 mg per day, or to highest tolerated dose, whichever came first. To be enrolled, patients had to have been treated with donepezil 10 mg per day for at least 12 weeks. Concomitant use of memantine was allowed, provided patients were treated with a stable dose of memantine for at least 8 weeks prior to enrollment, and providing the dose of memantine remained stable throughout the trial.

A total of 26 evaluable patients were enrolled in the study, 11 males and 15 females, mean age 74+8 years, and mean weight 74+18 kg. A total of 15 patients were on concomitant memantine upon study entry and remained on the same dose of memantine throughout the study.

Patients received increasing doses of donepezil together with a fixed dose of solifenacin (15 mg per day). A total of 22 patients reached and maintained the 40 mg/day dose of donepezil; 3 patients in the donepezil+memantine group (20%) and 2 patients in the donepezil without memantine group (18%) were not able to tolerate maximum allowed dose of 40 mg/day of donepezil. Thus, there was no difference in the percentage of patients on memantine and patients off memantine in their ability to tolerate high doses of donepezil.

Patients were tested on the ADAS-cog at study entry, when they reached Maximum Tolerated Dose (MTD) of donepezil, and 4 weeks after reaching MTD.

Response on the ADAS-cog was defined versus baseline as either no change or improvement. Four weeks after reaching their MTD, 73% of patients on memantine and only 60% of patients not receiving concomitant memantine were judged to be responders. These results show that unexpectedly, patients who were concomitantly treated with memantine had greater improvement with high doses of donepezil than patients receiving high doses of donepezil without concomitant memantine.

Since improvement was judged versus baseline, at a time when patients were either on or off memantine and remained that way for the duration of the trial, one would have expected any further increase in efficacy to be attributable only to the higher doses of donepezil. There should therefore have been no difference in improvement between high dose donepezil with memantine or without memantine. Yet, patients who were concomitantly treated with memantine had greater improvement with high doses of donepezil than patients receiving high doses of donepezil without concomitant memantine.

EXAMPLE 2

As a further approach to the result of the clinical trial of Example 1, after discarding the two best and the two worst responses to treatment of the patients with and without memantine, it was observed as follows.

No Memantine Co-Treatment:

Case 1. An 88 year old woman with a baseline MMSE score of 20 declined cognitively by 1.33 ADAS-cog points.

Case 2. An 80 year old woman with a baseline MMSE score of 18 declined by 3.65 points.

Case 3. A 57 year old man with a baseline MMSE score of 20 declined by 4.33 points.

Case 4. A 74 year old woman with a baseline MMSE score of 19 declined by 3.67 points Memantine Co-treated:

Case 1. A 63 year old man with a baseline MMSE score of 12 improved by −5.66 points.

Case 2. An 87 woman with a baseline MMSE score of 16 improved by −7.33 points at her maximum tolerated dose of 25 mg/day donepezil.

Case 3. An 81 man with a baseline MMSE score of 20 improved by −8.67 points.

Case 4. A 75 year old woman with a baseline MMSE score of 17 improved by −4.34 points.

The substantially greater cognitive benefit occurring with high dose (median 40 mg/day) donepezil treatment (administered with solifenacin 15 mg/day) in those also receiving standard dose memantine, compared with those who did not receive memantine, surprisingly attained statistical significance:

−6.5±0.95 versus 3.3±0.66, respectively; $p<0.05$).

The observed effect size in moderately severe AD patients is of conspicuous clinical significance.

EXAMPLE 3

Tablet containing 28 mg of memantine hydrochloride, formulated with a pharmaceutical carrier in ER-formulation, and tablets containing 10 mg of solifenacin succinate, formulated with a pharmaceutical carrier in IR-formulation, are distributed in capsules as described in GB 1,204,580, such that unit dosage forms each containing 28 mg of memantine hydrochloride in ER-formulation and 15 mg of solifenacin succinate in IR-formulation are prepared.

In the same manner, unit dosage forms each containing 28 mg of memantine hydrochloride formulated in admixture with a pharmaceutical carrier in an ER-formulation, tablets containing 15 mg of solifenacin succinate formulated with a pharmaceutical carrier in IR-formulation are prepared.

The invention claimed is:

1. A pharmaceutical combination comprising, as Components,
    (a) memantine or a pharmaceutically acceptable salt thereof; and
    (b) solifenacin or a pharmaceutically acceptable salt thereof.

2. The combination of claim 1, wherein said memantine or a pharmaceutically acceptable salt thereof is in a pharmaceutical composition in dosage unit form, in an amount that is equivalent to from 5 mg to 30 mg of memantine hydrochloride, in admixture with a pharmaceutical carrier; and said solifenacin or pharmaceutically acceptable salt thereof is in a pharmaceutical composition in dosage unit form, in an amount that is equivalent to from 10 mg to 30 mg of solifenacin succinate, in admixture with a pharmaceutical carrier.

3. The combination of claim 1, wherein said combination is a fixed-dose combination essentially consisting of a pharmaceutical composition comprising
    (a) memantine or a pharmaceutically acceptable salt thereof, in an amount that is equivalent to from 5 mg to 30 mg of memantine hydrochloride; and
    (b) solifenacin or a pharmaceutical acceptable salt thereof, in an amount that is equivalent to from 10 mg to 30 mg of solifenacin succinate,
    in admixture with a pharmaceutical carrier or vehicle.

4. A pharmaceutical combination comprising
    (a) memantine or a pharmaceutically acceptable salt thereof; and
    (b) solifenacin or a pharmaceutically acceptable salt thereof,
    for use for treating Alzheimer type dementia in further combination with donepezil or a pharmaceutically acceptable salt thereof.

5. The combination of claim 4 wherein, in said combination, memantine or pharmaceutically acceptable salt is in a pharmaceutical composition comprising said memantine or pharmaceutically acceptable salt thereof in an amount that is equivalent to from 5 mg to 30 mg of memantine hydrochloride, in admixture with a pharmaceutical carrier or vehicle; and said solifenacin or pharmaceutically acceptable salt thereof is in a pharmaceutical composition comprising said solifenacin or pharmaceutically acceptable salt thereof, in an amount that is equivalent to from 10 mg to 30 mg of solifenacin succinate, in admixture with a pharmaceutical carrier or vehicle.

6. The combination of claim 4, wherein said memantine or pharmaceutically acceptable salt thereof and said solifenacin or pharmaceutically acceptable salt thereof are in a fixed-dose combination essentially consisting of a pharmaceutical composition comprising said memantine or pharmaceutically acceptable salt thereof, in an amount that is equivalent to from 5 mg to 30 mg; and said solifenacin or pharmaceutically acceptable salt, in an amount that is equivalent to from 10 to 30 mg, in admixture with a pharmaceutical carrier or vehicle.

7. A pharmaceutical composition in dosage unit form, which comprises (a) memantine hydrochloride, in an amount of from 5 mg to 30 mg; and (b) solifenacin succinate, in an amount of from 10 mg to 30 mg, in admixture with a pharmaceutical carrier or vehicle.

8. A pharmaceutical unit form comprising (a) memantine hydrochloride, in a pharmaceutical composition comprising said memantine hydrochloride in an amount of from 5 mg to 30 mg, in admixture with a pharmaceutical carrier in extended-release formulation; and (b) solifenacin succinate, in a pharmaceutical composition comprising said solifenacin succinate in an amount of from 10 mg to 30 mg, in admixture with a pharmaceutical carrier or vehicle in an immediate release formulation.

* * * * *